US012559476B2

(12) United States Patent
Kanazawa et al.

(10) Patent No.: US 12,559,476 B2
(45) Date of Patent: Feb. 24, 2026

(54) COMPOUND AND LABELED BIOLOGICAL SUBSTANCE USING THE SAME

(71) Applicant: FUJIFILM Corporation, Tokyo (JP)

(72) Inventors: Yoshinori Kanazawa, Kanagawa (JP); Ryo Fujiwara, Kanagawa (JP); Kenji Shirokane, Kanagawa (JP); Kousuke Watanabe, Kanagawa (JP); Yuki Arai, Kanagawa (JP); Kazuoki Komiyama, Kanagawa (JP); Hiroaki Tanaka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 555 days.

(21) Appl. No.: 18/048,426

(22) Filed: Oct. 20, 2022

(65) Prior Publication Data

US 2023/0219932 A1 Jul. 13, 2023

Related U.S. Application Data

(63) Continuation of application No. PCT/JP2021/016361, filed on Apr. 22, 2021.

(30) Foreign Application Priority Data

Apr. 24, 2020 (JP) ................................ 2020-077176
Jul. 30, 2020 (JP) ................................ 2020-129753

(51) Int. Cl.
*C07D 403/00* (2006.01)
*C07D 403/08* (2006.01)
*C07D 471/04* (2006.01)

(52) U.S. Cl.
CPC ......... *C07D 403/08* (2013.01); *C07D 471/04* (2013.01)

(58) Field of Classification Search
CPC .................................................. C07D 403/08
USPC ........................................................ 548/465
See application file for complete search history.

(56) References Cited

U.S. PATENT DOCUMENTS 8,088,552 B2 * 1/2012 Ozaki .................. B41C 1/1008 430/287.1
9,023,611 B2 5/2015 Frangioni et al.
9,097,667 B2 8/2015 Mao et al.
9,687,567 B2 6/2017 Frangioni et al.
9,791,450 B2 10/2017 Mao et al.
10,000,467 B2 6/2018 Hermanson et al.
10,201,621 B2 2/2019 Frangioni et al.
10,478,512 B2 11/2019 Frangioni et al.
10,696,653 B2 6/2020 Hermanson et al.
2003/0113755 A1 6/2003 Nishigaki et al.
2006/0239922 A1 10/2006 Cooper et al.
2009/0305410 A1 12/2009 Mao et al.
2010/0249385 A1 9/2010 Cooper et al.
2012/0156140 A1 6/2012 Hermanson et al.
2012/0329068 A1 * 12/2012 Mao .................... G01N 33/533 435/7.1
2013/0230466 A1 9/2013 Hermanson et al.
2014/0072515 A9 3/2014 Hermanson et al.
2014/0255312 A1 9/2014 Hermanson et al.
2018/0156810 A1 6/2018 Mao et al.

FOREIGN PATENT DOCUMENTS

CN 104395306 3/2015
EP 2325263 5/2011
JP 2003034696 2/2003
JP 2008538382 10/2008
JP 2011506673 3/2011
(Continued)

OTHER PUBLICATIONS

"Office Action of China Counterpart Application", issued on Sep. 14, 2024, with English translation thereof, p. 1-p. 13.
"International Search Report (Form PCT/ISA/210) of PCT/JP2021/016361," mailed on Jul. 20, 2021, with English translation thereof, pp. 1-7.
"Written Opinion of the International Searching Authority (Form PCT/ISA/237)" of PCT/JP2021/016361, mailed on Jul. 20, 2021, with English translation thereof, pp. 1-6.
"Office Action of China Counterpart Application", issued on May 16, 2024, with English translation thereof, p. 1-p. 16.
"Search Report of Europe Counterpart Application", issued on Oct. 30, 2023, p. 1-p. 13.
(Continued)

*Primary Examiner* — Andrew D Kosar
*Assistant Examiner* — Emily R. Berkeley
(74) *Attorney, Agent, or Firm* — JCIPRNET

(57) ABSTRACT

A compound of Formula (1) and a labeled biological substance having the compound.

General Formula (1)

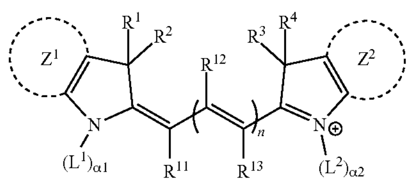

$Z^1$ and $Z^2$ represent a specific 6-membered ring, and at least one of $Z^1$ or $Z^2$ is a benzene ring having a specific substituent at an ortho position with respect to a nitrogen atom to which $L^1$ or $L^2$ is bonded, or a specific nitrogen-containing 6-membered ring in which a ring-constituting atom located at the ortho position is a nitrogen atom. The compound has at least one structure represented by $—(CH_2—CH_2—O)_m—R^{21}$ on a heterocyclic ring, and has at least one substituent capable of being bonded to a carboxy group or a biological substance at a specific position, and in a case where at least one of $Z^1$ or $Z^2$ is the specific nitrogen-containing 6-membered ring, the specific substituents may be bonded to each other to form a ring.

11 Claims, No Drawings

(56) References Cited

FOREIGN PATENT DOCUMENTS

| | | |
|---|---|---|
| JP | 2012517436 | 8/2012 |
| WO | 0102374 | 1/2001 |
| WO | 2009078970 | 6/2009 |
| WO | 2010091243 | 8/2010 |
| WO | 2012054749 | 4/2012 |
| WO | 2012129128 | 9/2012 |
| WO | 2013130761 | 9/2013 |
| WO | 2019161159 | 8/2019 |

OTHER PUBLICATIONS

Dong-Hao Li et al., "Sterically Shielded Heptamethine Cyanine Dyes for Bioconjugation and High Performance Near-Infrared Fluorescence Imaging," Angewandte Chemie International Edition, vol. 59, May 2020, pp. 12154-12161.
"Office Action of China Counterpart Application", issued on Nov. 28, 2024, with English translation thereof, p. 1-p. 19.
"Office Action of China Counterpart Application", issued on Nov. 11, 2023, with English translation thereof, p. 1-p. 13.

* cited by examiner

COMPOUND AND LABELED BIOLOGICAL SUBSTANCE USING THE SAME

CROSS-REFERENCE TO RELATED APPLICATIONS

This application is a Continuation of PCT International Application No. PCT/JP2021/016361 filed on Apr. 22, 2021, which claims priority under 35 U.S.C. § 119 (a) to Japanese Patent Application No. 2020-077176 filed in Japan on Apr. 24, 2020, and Japanese Patent Application No. 2020-129753 filed in Japan on Jul. 30, 2020. Each of the above applications is hereby expressly incorporated by reference, in its entirety, into the present application.

BACKGROUND OF THE INVENTION

1. Field of the Invention

The present invention relates to a compound and a labeled biological substance using the compound.

2. Description of the Related Art

In order to observe in vivo changes in response to various stimuli (diseases, environmental changes, and the like), fluorescently labeled biological substances obtained by labeling a biological molecule (an antibody or the like) having a binding property to a target substance to be detected, with a fluorescent compound (a dye), are often used.

For example, also in Western blotting (hereinafter, also abbreviated as WB) that detects a specific protein from a protein mixture, a fluorescence method in which the presence or absence or the abundance of the specific protein is detected using a fluorescently labeled antibody having a binding property to this protein.

In addition, in bioimaging technology for analyzing the dynamics and functions of biological molecules, cells, tissues, and the like in a living body, in vivo fluorescence imaging in which a specific portion of a living body visualized by fluorescence labeling is observed is used as one of the techniques for the living body observation.

A cyanine dye is known as a fluorescent dye that is used for fluorescence labeling. However, in a case where a cyanine dye is used for fluorescence labeling, interactions such as self-association between the dyes after labeling easily occur, and the fluorescence quantum yield tends to decrease.

As a technique for coping with this problem, for example, WO2009/078970A and WO2013/130761A describe a cyanine dye into which a water-soluble polyethylene glycol (PEG) group has been introduced. According to WO2009/078970A and WO2013/130761A, the cyanine dyes described in the WO2009/078970A and WO2013/130761A are said to exhibit a high fluorescence intensity as compared with the cyanine dyes in the related art by suppressing self-association between the dyes after labeling, due to the PEG group contained in the dyes.

SUMMARY OF THE INVENTION

However, from the studies by the inventors of the present invention, it was found that in the fluorescent labeling using the cyanine dyes described in WO2009/078970A and WO2013/130761A, the binding property of the cyanine dye to a biological molecule such as an antibody is low. As a result, it was found that the fluorescence intensity obtained in a case of using a dye having the same equivalent as the cyanine dye in the related art is low, and thus a sufficient fluorescence intensity cannot be obtained.

An object of the present invention is to provide a compound that has a good binding property to a biological substance and exhibits an excellent fluorescence intensity of a labeled biological substance to be obtained. In addition, another object of the present invention is to provide a labeled biological substance obtained by bonding the compound to a biological substance.

That is, the above objects of the present invention have been achieved by the following means.

[1] A compound represented by General Formula (1),

General Formula (1)

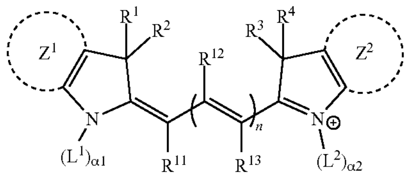

in the formula, $R^1$ to $R^4$ represent an alkyl group which may have a substituent, an aryl group, a heteroaryl group, or $-(CH_2-CH_2-O)_m-R^{21}$, where m is 1 to 10 and $R^{21}$ represents an alkyl group which may have a substituent, $R^{11}$ to $R^{13}$ represent a hydrogen atom, an alkyl group, an aryl group, a heteroaryl group, an alkoxy group, an aryloxy group, an alkylthio group, an arylthio group, an amino group, or a halogen atom, where adjacent groups may be bonded to each other to form a 5-membered or 6-membered ring, n is an integer of 1 to 3, $L^1$ and $L^2$ represent an alkyl group which may have a substituent or $-(CH_2-CH_2-O)_m-R^{21}$, where $R^{21}$ and m are respectively synonymous with $R^{21}$ and m described above, α1 and α2 are 0 or 1, a ring $Z^1$ and a ring $Z^2$ represent a 6-membered ring formed of a ring-constituting atom selected from a carbon atom and a nitrogen atom, may have a substituent, and may form a fused ring, provided that at least one of the ring $Z^1$ or the ring $Z^2$ is a benzene ring represented by General Formula (Zα) or a nitrogen-containing 6-membered ring satisfying the following definition (Zβ), General Formula (Zα)

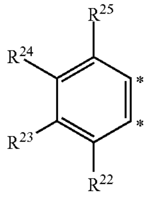

in the formula, $R^{22}$ represents an alkyl group, an alkoxy group, a sulfo group, a sulfonamide group, a nitro group, or a halogen atom, $R^{23}$ to $R^{25}$ represent a hydrogen atom, an alkyl group, an alkoxy group, an aryl group, a sulfo group, a sulfonamide group, a nitro group, or a halogen atom, where adjacent groups may be bonded to each other to form a fused ring, a structure represented by General Formula (Zα) is bonded, at a position of *, to a heterocyclic ring containing a nitrogen atom in General Formula (1) so that $R^{22}$ is at an ortho position with respect to the nitrogen atom to which $L^1$ or $L^2$ is bonded, the definition (Zβ): a nitrogen-containing 6-membered ring in which a ring-constituting atom located at an ortho position with respect to a nitrogen atom to which $L^1$ or $L^2$ is bonded is a nitrogen atom, the ring-constituting nitrogen atom located at the ortho position may be substituted with a substituent, at least one of $R^1$ to $R^4$, $L^1$, or $L^2$ contains a structure represented by $-(CH_2-CH_2-O)_m-R^{21}$, where $R^{21}$ and m are respectively synonymous with $R^{21}$ and m described above, at least one of the substituents contained in $L^1$ and $L^2$ and possessed by the ring-constituting nitrogen atom located at the ortho position includes a substituent capable of being bonded to a carboxy group or a biological substance, and in a case where at least one of $Z^1$ or $Z^2$ is the nitrogen-containing 6-membered ring satisfying the definition (Zβ), two of the substituents contained in $L^1$, $L^2$, and $R^1$ to $R^4$ and possessed by the ring-constituting nitrogen atom located at the ortho position may be bonded to each other to form a ring containing a methine chain having a repetition number of 2n+3, provided that the compound represented by Formula (1) is a neutral compound.

[2] The compound according to [1], in which the compound is represented by any one of General Formulae (2-1) to (2-3), General Formula (2-1)

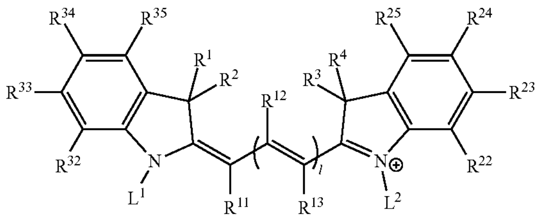

General Formula (2-2)

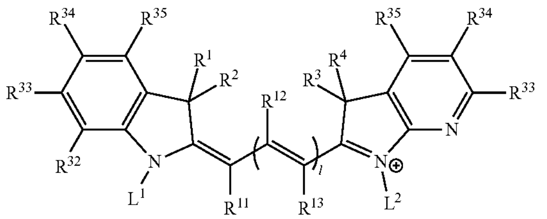

-continued

General Formula (2-3)

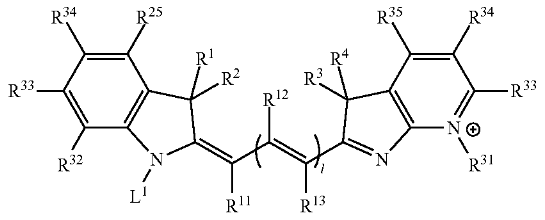

in the formulae, $R^{31}$ represents an alkyl group which may have a substituent or $-(CH_2-CH_2-O)_m-R^{21}$, $R^{32}$ to $R^{35}$ represent a hydrogen atom, an alkyl group, an alkoxy group, an aryl group, a sulfo group, a sulfonamide group, a nitro group, or a halogen atom, where adjacent groups may be bonded to each other to form a fused ring, $R^1$ to $R^4$, $R^{11}$ to $R^{13}$, $L^1$, $L^2$, $R^{21}$ to $R^{25}$, and m are respectively synonymous with $R^1$ to $R^4$, $R^{11}$ to $R^{13}$, $L^1$, $L^2$, $R^{21}$ to $R^{25}$, and m described above, 1 represents 2 or 3, and at least one of $L^1$, $L^2$, or $R^{31}$ contains a substituent capable of being bonded to a carboxy group or a biological substance, provided that the compound represented by any one of Formulae (2-1) to (2-3) is a neutral compound.

[3] The compound according to [1] or [2], in which at least one of $R^1$ or $R^2$ described above and at least one of $R^3$ or $R^4$ described above includes a structure represented by $-(CH_2-CH_2-O)_m-$, where m is 1 to 10.

[4] The compound according to any one of [1] to [3], in which at least one of the substituents contained in $L^1$ and $L^2$ and possessed by the ring-constituting nitrogen atom located at the ortho position in the definition (Zβ) or $R^{31}$ includes a substituent capable of being bonded to a carboxy group or a biological substance, and a structure represented by $-(CH_2-CH_2-O)_m$, where m is 1 to 10.

[5] The compound according to any one of [1] to [4], in which at least one of $R^{11}$ to $R^{13}$ described above is an aryloxy group or an arylthio group.

[6] The compound according to [1], in which the compound is represented by any one of General Formulae (5-1) to (5-4), General Formula (5-1)

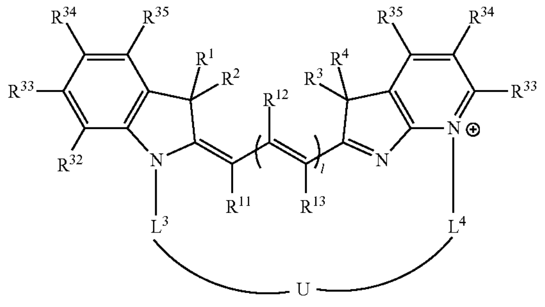

-continued

General Formula (5-2)

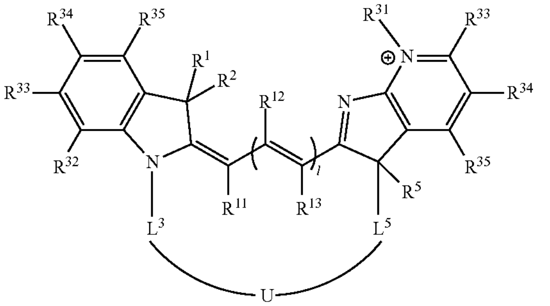

General Formula (5-3)

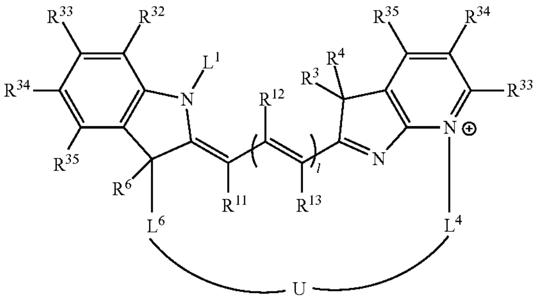

General Formula (5-4)

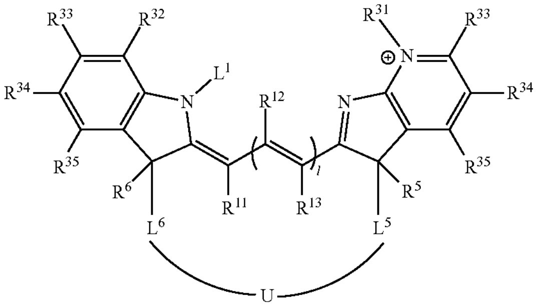

in the formulae, $R^1$ to $R^6$ represent an alkyl group which may have a substituent, an aryl group, a heteroaryl group, or $—(CH_2—CH_2—O)_m—R^{21}$, $R^{31}$ represents an alkyl group which may have a substituent or $—(CH_2—CH_2—O)_m—R^{21}$, $R^{32}$ to $R^{35}$ represent a hydrogen atom, an alkyl group, an alkoxy group, an aryl group, a sulfo group, a sulfonamide group, a nitro group, or a halogen atom, where adjacent groups may be bonded to each other to form a fused ring, 1 represents 2 or 3, and $L^3$ to $L^6$ represent an alkylene group or $—(CH_2—CH_2—O)_m$-alkylene-* where * represents a bonding position to U, a linking group U represents a divalent linking group having a total number of atoms of 1 to 100, $R^{11}$ to $R^{13}$, $R^{21}$, $L^1$, and m are respectively synonymous with $R^{11}$ to $R^{13}$, $R^{21}$, $L^1$, and m described above, at least one of $R^1$ to $R^6$, $L^1$, $R^{31}$, or $L^3$ to $L^6$ includes a structure represented by $—(CH_2—CH_2—O)_m—$, where m is synonymous with m described above, and at least one of $L^1$, $R^{31}$, $L^3$ to $L^6$, or the linking group U contains a substituent capable of being bonded to a carboxy group or a biological substance, provided that the compound represented by any one of Formulae (5-1) to (5-4) is a neutral compound.

[7] The compound according to [6], in which in the linking group U, a connecting portion to $L^3$ to $L^6$ is an —O— group, an $—NR^{50}—$ group, a —COO— group, a $—CONR^{50}—$ group, or an $—SO_2NR^{50}—$ group, provided that $R^{50}$ is a hydrogen atom or an alkyl group.

[8] The compound according to [6] or [7], in which at least one of $R^1$ or $R^2$ and at least one of $R^3$ or $R^4$ includes a structure represented by $—(CH_2—CH_2—O)_m$, where m is 1 to 10.

[9] The compound according to any one of [6] to [8], in which all of $L^3$ to $L^6$ described above contains a structure represented by $—(CH_2—CH_2—O)_m—$, where m is 1 to 10.

[10] The compound according to any one of [6] to [9], in which the linking group U is a divalent linking group having a substituent capable of being bonded to a carboxy group or a biological substance.

[11]A labeled biological substance that is obtained by bonding the compound according to any one of [1] to [10] to a biological substance.

[12] The labeled biological substance according to [11], in which the biological substance is any one of a protein, an amino acid, a nucleic acid, a sugar chain, or a phospholipid.

The compound according to an aspect of the present invention exhibits a good binding property to a biological substance, and thus an obtained labeled biological substance exhibits an excellent fluorescence intensity. In addition, the labeled biological substance according to an aspect of the present invention exhibits an excellent fluorescence intensity.

DESCRIPTION OF THE PREFERRED EMBODIMENTS

In the present invention, in a case where there is a plurality of substituents or linking groups represented by a specific symbol or Formula (hereinafter, referred to as substituents or the like), or in a case where a plurality of substituents or the like are regulated at the same time, the substituents or the like may be the same or different from each other, unless otherwise specified. The same applies to the regulation of the number of substituents or the like. Further, in a case where a plurality of substituents or the like come close to each other (particularly in a case where they are adjacent to each other), they may be linked to each other to form a ring, unless otherwise specified. Further, unless otherwise specified, rings such as an alicyclic ring, an aromatic ring, and a heterocyclic ring may be fused to form a fused ring.

In the present specification, in a case where the E type and the Z type of the double bond are present in the molecule, any one of the E type or the Z type, or a mixture thereof may be used unless otherwise specified. In addition, in a case where a compound has diastereomers and enantiomers, any one of the diastereomers or the enantiomers may be used, or a mixture thereof may be used unless otherwise specified.

In the present invention, the representation of a compound or substituent is meant to include not only the compound itself but also a salt thereof, and an ion thereof. For example, the carboxy group, the sulfo group, and the phosphono group ($—P(=O)(OH)_2$) may have an ionic structure by a hydrogen atom being dissociated therefrom, or they may have a salt structure. That is, in the present invention, the "carboxy group" is meant to include an ion or salt of a carboxylic acid, the "sulfo group" is meant to include an ion or salt of a sulfonic acid, and the "phosphono group" is meant to include an ion or salt of a phosphonic acid. The monovalent or polyvalent cation in forming the salt structure is not particularly limited, and examples thereof include an inorganic cation and an organic cation. Specific examples thereof include alkali metal cations such as $Na^+$, $Li^+$, and $K^+$, alkaline earth metal cations such as $Mg^{2+}$, $Ca^{2+}$, and $Ba^{2+}$ and organic ammonium cations such as a trialkylammonium cation and a tetraalkylammonium cation.

In a case of a salt structure, the kind of the salt may be one kind, two or more kinds thereof may be mixed, a salt-type group and a group having a free acid structure may be mixed in a compound, and a compound having a salt structure and a compound having a free acid structure compound may be mixed.

Any compound according to the embodiment of the present invention is a neutral compound. In the present invention, the fact that the compound is neutral means that the compound is electrically neutral. Specifically, the charge of the compound as a whole is adjusted to be 0 by a group having a charge or by a counterion in the compound. For example, in the compound represented by General Formula (1), the formal charge of the nitrogen atom to which $L^2$ is bonded is +1 except for a case of $\alpha2=0$. In order to be paired with this formal charge, a dissociable group such as a sulfo group in the compound has an ionic structure such as a sulfonate ion, and thus the compound according to the embodiment of the present invention is a compound having a charge of 0 as a whole. In a case of $\alpha2=0$, the formal charge of the nitrogen atom to which $L^2$ is bonded is 0.

It is noted that in the compound represented by General Formula (1), the formal charge of the nitrogen atom to which $L^1$ is bonded is 0 in a case of $\alpha1=1$. In a case of $\alpha1=0$, a conjugated structure, in which the bonding portion between the nitrogen atom to which $L^1$ is bonded and the ring $Z^1$ becomes a double bond instead of the double bond of the fused portion between the 5-membered ring containing the nitrogen atom to which $L^1$ is bonded in General Formula (1) and the ring $Z^1$, is adopted so that the formal charge of the nitrogen atom to which the $L^1$ is bonded is 0.

In each general formula defined in the present invention, the positive charge possessed by the compound is specified and indicated, for convenience, as a structure of a specific nitrogen atom. However, since the compound according to the embodiment of the present invention has a conjugated system, another atom other than the nitrogen atom actually may be capable of being positively charged, and thus any compound capable of adopting a structure represented by each general formula as one of the chemical structures is included in the compound represented by each general formula. This also applies to the negative charge.

In the present invention, in a heterocyclic ring which contains a nitrogen atom to which $L^1$ is bonded, as a ring-constituting atom, and in which the ring $Z^1$ is fused, in a case where the nitrogen atom to which $L^1$ is bonded is set as the 1-position and the carbon atom to which $R^1$ and $R^2$ are bonded is set as the 3-position, the ortho position with respect to the nitrogen atom to which $L^1$ is bonded means each of the 6-position in a case where the ring $Z^1$ is a 5-membered ring and the 7-position in a case where the ring $Z^1$ is a 6-membered ring. For example, in General Formulae (2-1) to (2-3), the substituent located at the ortho position with respect to the nitrogen atom to which $L^1$ is bonded is $R^{32}$. This also applies to the ortho position with respect to the nitrogen atom to which $L^2$ is bonded.

In addition, it is meant to include those in which a part of the structure is changed within the scope that does not impair the effects of the present invention. Furthermore, it is meant that a compound, which is not specified to be substituted or unsubstituted, may have any substituent within the scope that does not impair the effects of the present invention. The same applies to a substituent (for example, a group represented by "alkyl group", "methyl group", "methyl") and a linking group (for example, a group represented by "alkylene group", "methylene group", "methylene"). Among such substituents, a preferred substituent in the present invention is a substituent selected from a substituent group T described later.

In the present invention, in a case where the number of carbon atoms of a certain group is specified, this number of carbon atoms means the number of carbon atoms of the entire group thereof unless otherwise specified in the present invention or the present specification. That is, in a case where this group has a form of further having a substituent, it means the total number of carbon atoms, to which the number of carbon atoms of this substituent is included.

In addition, in the present invention, the numerical range represented by using "to" means a range including the numerical values before and after "to" as the lower limit value and the upper limit value, respectively.

The compound according to an embodiment of the present invention is represented by General Formula (1). Although the details of the reason why the compound according to the embodiment of the present invention exhibits a good binding property to a biological substance and an obtained labeled biological substance exhibits an excellent fluorescence intensity are not clear, they are conceived to be as follows.

As represented by General Formula (1), the compound according to the embodiment of the present invention has a polymethine chain having a heterocyclic ring which contains a nitrogen atom as a ring-constituting atom and in which a ring $Z^1$ or a ring $Z^2$ is fused at both terminals (in the present invention, the polymethine chain means a methine chain bonded by a conjugated double bond, which is a methine chain having 2n+3 carbon atoms constituting the methine chain, and is also referred to as a methine chain having a repetition number of 2n+3), and furthermore, the nitrogen atom of the heterocyclic ring in which the ring $Z^1$ is fused has a tertiary amine structure, and the nitrogen atom of the heterocyclic ring in which the ring $Z^2$ is fused has a quaternary ammonium structure, whereby the absorption due to charge transfer through the polymethine skeleton occurs. The compound according to the embodiment of the present invention as described above is classified into a compound referred to as a polymethine dye (broadly, a cyanine dye).

The compound according to the embodiment of the present invention has the above-described structure, and furthermore, in the above-described two heterocyclic rings, at least one of $R^1$ to $R^4$ bonded to the ring-constituting carbon atom at the 3-position or $L^1$ and $L^2$ substituted at the ring-constituting nitrogen atom has a structure including a polyethylene glycol (PEG) group represented by $-(CH_2-CH_2-O)_m-R^{21}$, where m is 1 to 10, and at least one of the substituents which can be contained in $L^1$ and $L^2$ and the ring $Z^1$ or ring $Z^2$ and are possessed by the ring-constituting nitrogen atom located at the ortho position in the definition ($Z\beta$) described later has a substituent capable of being bonded to a biological substance. As a result, in the compound having a PEG group having m of more than 10, the decrease in the binding property to a biological substance caused by the large excluded volume effect can be suppressed, and a good binding property to the biological substance can be exhibited.

In addition, the compound according to the embodiment of the present invention has, as at least one of the above-described ring $Z^1$ and ring $Z^2$, a benzene ring having a substituent at the ortho-position with respect to the nitrogen atom, where the benzene ring is represented by General Formula (Zα) described below, or a nitrogen-containing 6-membered ring which satisfies Z(β) described later and in which the ortho position with respect to the nitrogen atom is a position where a nitrogen atom is located. For this reason, the interaction between the compounds is suppressed by the stereoscopic effect of the substituent at the ortho-position with respect to the ring-constituting nitrogen atom of the heterocyclic ring bonded to the terminal of the polymethine chain and the hydrophilic effect obtained by the nitrogen atom located at the ortho-position, and as a result, it is conceived that a decrease in fluorescence intensity due to self-association of the compounds can be suppressed.

Depending on the length of the methine chain having a repetition number of 2n+3, the compounds according to the embodiment of the present invention respectively have an excitation absorption wavelength in the vicinity of 585 nm in a case of n=1, in the vicinity of 685 nm in a case of n=2, and in the vicinity of 785 nm in a case of n=3. As a result, these compounds represented by General Formula (1) can be used as compounds having a good binding property to a biological substance and an excellent fluorescence intensity in the fluorescence labeling using excitation light sources respectively having wave lengths in the vicinity of 600 nm, 700 nm, and 800 nm.

In multicolor WB, a plurality of emission colors are detected in the range from the visible range to the near infrared range. As a result, it is necessary to select wavelengths so that the absorption and emission waveforms of a plurality of dyes have a suitable wavelength relationship so that crosstalk does not occur due to mutual interference in a case where the dyes are excited to emit light. Ideally, it should be adjusted so that only one dye emits light at one excitation light and the other dyes do not emit light. From this point of view, two kinds of excitation light sources having wavelengths separated to some extent, for example, in the vicinity of 700 nm and in the vicinity of 800 nm, are used for light emission in the near infrared range of the multicolor WB.

As compared with the detection by visible light excitation, the fluorescence detection by near-infrared light excitation can suppress the autofluorescence of the membrane, that is, the background fluorescence, and thus it is easy to increase the signal to noise ratio (the S/N ratio) and it is possible to detect a target protein with high sensitivity. As a result, in recent years, there has been an increasing need for fluorescence detection WB using light emission in the near infrared range in the analytical research on the trace amount of proteins.

However, in the near infrared range, the fluorescence quantum yield of the fluorescent dye is generally low, and thus it is difficult to obtain a high signal amount. Among the compounds according to the embodiment of the present invention, the compound in which n=2 or 3 can be used as compound that exhibits a good binding property to a biological substance and an excellent fluorescence intensity even in the multicolor WB having the above-described two kinds of excitation light sources in the vicinity of 700 nm and in the vicinity of 800 nm, and in particular, it can exhibit a good binding property to a biological substance and an excellent fluorescence intensity even with respect to a request for observing and detecting proteins with higher sensitivity, as compared with the fluorescence labeling using cyanine dyes in the related art including the cyanine dyes described in WO2009/078970A and WO2013/130761A.

Hereinafter, the compound according to the embodiment of the present invention, which is represented by General Formula (1), will be described in detail.

<Compound Represented by General Formula (1)>

The compound according to the embodiment of the present invention, which is represented by General Formula (1), is as follows.

General Formula (1)

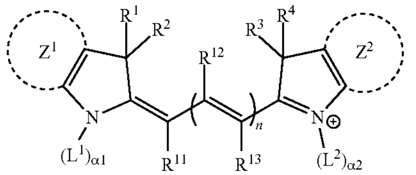

In the formula, $R^1$ to $R^4$ represent an alkyl group which may have a substituent, an aryl group, a heteroaryl group, or $-(CH_2-CH_2-O)_m-R^{21}$, where m is 1 to 10 and $R^{21}$ represents an alkyl group which may have a substituent.

$R^{11}$ to $R^{13}$ represent a hydrogen atom, an alkyl group, an aryl group, a heteroaryl group, an alkoxy group, an aryloxy group, an alkylthio group, an arylthio group, an amino group, or a halogen atom, where adjacent groups may be bonded to each other to form a 5-membered or 6-membered ring.

n is an integer of 1 to 3.

$L^1$ and $L^2$ represent an alkyl group which may have a substituent or $-(CH_2-CH_2-O)_m-R^{21}$, where $R^{21}$ and m are respectively synonymous with $R^{21}$ and m described above.

α1 and α2 are 0 or 1.

A ring $Z^1$ and a ring $Z^2$ represent a 6-membered ring formed of a ring-constituting atom selected from a carbon atom and a nitrogen atom, may have a substituent, and may form a fused ring. However, at least one of the ring $Z^1$ or the ring $Z^2$ is a benzene ring represented by General Formula (Zα) described later or a nitrogen-containing 6-membered ring satisfying the following definition (Zβ) described later.

At least one of $R^1$ to $R^4$, $L^1$, or $L^2$ contains a structure represented by $-(CH_2-CH_2-O)_m-R^{21}$, where $R^{21}$ and m are respectively synonymous with $R^{21}$ and m described above. However, as described later, in a case where two of the substituents contained in $L^1$, $L^2$, and $R^1$ to $R^4$ and possessed by the ring-constituting nitrogen atom located at the ortho position are bonded to each other, it suffices that at least one of $R^1$ to $R^4$, $L^1$, or $L^2$ includes a structure represented by $-(CH_2-CH_2-O)_m-$.

At least one of the substituents contained in $L^1$ and $L^2$ and possessed by the ring-constituting nitrogen atom located at the ortho position in the definition (Zβ) described later includes a substituent capable of being bonded to a carboxy group or a biological substance.

In a case where at least one of $Z^1$ or $Z^2$ is the nitrogen-containing 6-membered ring satisfying the definition (Zβ) described later, two of the substituents contained in $L^1$ and $L^2$ and possessed by the ring-constituting nitrogen atom located at the ortho position in the definition (Zβ) described later may be bonded to each other to form a ring containing a methine chain having a repetition number of 2n+3.

However, the compound represented by Formula (1) is a neutral compound.

Hereinafter, the substituent and the like in General Formula (1) will be described in detail.

(1) $R^1$ to $R^4$ $R^1$ to $R^4$ each independently represent an alkyl group which may have a substituent, an aryl group, a heteroaryl group, or $-(CH_2-CH_2-O)_m-R^{21}$. $R^1$ and $R^2$ may be linked to each other to form a ring, and $R^3$ and $R^4$ may be linked to each other to form a ring.

The alkyl group, the aryl group, and the heteroaryl group, which can be adopted as $R^1$ to $R^4$ are synonymous with the alkyl group, the aryl group, and the heteroaryl group in the substituent group T described later.

The unsubstituted alkyl group preferably has 1 to 6 carbon atoms, more preferably 1 to 4 carbon atoms, and still more preferably 1 or 2 carbon atoms.

The alkyl group moiety of the alkyl group having a substituent preferably has 1 to 10 carbon atoms, more preferably 1 to 8 carbon atoms, still more preferably 2 to 6 carbon atoms, and even still more preferably 3 to 5 carbon atoms. In addition, the number of atoms constituting the longest chain of the alkyl group having a substituent is preferably 3 to 35, more preferably 3 to 30, and still more preferably 3 to 25. However, as described later, in a case where two of the substituents contained in $L^1$ and $L^2$ and possessed by the ring-constituting nitrogen atom located at the ortho position in the definition (Zβ) described later are bonded to each other, the number of atoms constituting the portion corresponding to the longest chain of the alkyl group having a substituent is preferably 5 to 50, more preferably 5 to 40, and still more preferably 5 to 30, in the group composed of $L^3$ to $L^6$ and the linking group U.

In the present invention, the "number of carbon atoms of the alkyl group moiety of the alkyl group having a substituent" means the number of carbon atoms excluding the substituent moiety contained in the alkyl group.

In the present invention, the "number of atoms constituting the longest chain of the alkyl group having a substituent" means the number of atoms including the substituent moiety (that is, the number of atoms obtained by subtracting the number of atoms of the molecular chain that does not constitute the longest chain, from the number of total atoms). It is noted that in a case where a substituent having a dissociative hydrogen atom such as a sulfo group or a carboxy group constitutes the longest chain, the calculation is carried out including the hydrogen atom regardless of the presence or absence of dissociation. In addition, the number of atoms in the substituent moiety capable of being bonded to a biological substance described later is not included.

Examples of the substituent which may be contained in the alkyl group which can be adopted as $R^1$ to $R^4$ include an alkoxy group, a carboxy group, an alkoxycarbonyl group, a carboxy group, an aminocarbonyl group, an acylamino group, a sulfo group, a phosphono group, and $-(CH_2-CH_2-O)_m-R^{21}$, as well as a group consisting of a combination of these substituents. In addition, examples thereof include a substituent capable of being bonded to a biological substance described later. It is noted that the alkoxy group moiety in the alkoxy group, the carboxy group, the alkoxycarbonyl group, the acyloxy group, the aminocarbonyl group, the acylamino group, the sulfo group, and the phosphono group, as well as the group consisting of a combination of these substituents may have a substituent capable of being bonded to a biological substance described later.

The alkyl group having a substituent, which can be adopted as $R^1$ to $R^4$, is not particularly limited as long as it is the above-described alkyl group having a substituent. However, from the viewpoint of suppressing the interaction between molecules, it is preferably an alkyl group having $-(CH_2-CH_2-O)_m-R^{21}$ as a substituent. In this case, the alkyl group may be directly substituted with $-(CH_2-CH_2-O)_m-R^{21}$, or it may be substituted with a group consisting of a combination of a carbamoyl group and $-(CH_2-CH_2-O)_m-R^{21}$.

($-(CH_2-CH_2-O)_m-R^{21}$)

In $-(CH_2-CH_2-O)_m-R^{21}$ which can be adopted as $R^1$ to $R^4$, m is 1 to 10, and $R^{21}$ represents an alkyl group which may have a substituent.

m means an average repetition number (simply also referred to as a repetition number), and it is preferably 4 to 10 and more preferably 4 to 8.

The average repetition number can be calculated from the average integrated value obtained by subjecting a compound to $^1$H-NMR measurement. The average repetition number defined in the present invention means a number obtained by rounding off the first decimal place of the average repetition number calculated according to the above method.

As the alkyl group which may have a substituent, as $R^{21}$, the description for the alkyl group which may have a substituent, which can be adopted as $R^1$ to $R^4$, can be applied.

The $-(CH_2-CH_2-O)_m-R^{21}$ which can be adopted as $R^1$ to $R^4$ and $-(CH_2-CH_2-O)_m-R^{21}$ contained in $R^1$ to $R^4$ are preferably an alkyl group of $-(CH_2-CH_2-O)_m$-unsubstituted.

It is preferable that at least one of $R^1$ to $R^4$ includes a structure represented by $-(CH_2-CH_2-O)_m-$, and from the viewpoint of further improving the fluorescence intensity, it is more preferable at least one of $R^1$ or $R^2$ and at least one of $R^3$ or $R^4$ include a structure represented by $-(CH_2-CH_2-O)_m-$. The structure represented by $-(CH_2-CH_2-O)_m-$ is preferably directly bonded, as $-(CH_2-CH_2-O)_m-R^{21}$, to a heterocyclic ring directly bonded to the methine chain.

The m in $-(CH_2-CH_2-O)_m-$ described above is synonymous with the m in $-(CH_2-CH_2-O)_m-R^{21}$ described above.

Since the substituents of $R^1$ to $R^4$ protrude in a direction perpendicular to the cyanine dye skeleton (plane), it is presumed that in a case of including a structure represented by $-(CH_2-CH_2-O)_m-$ as this substituent, the fused ring portion is difficult to undergo the π-π interaction (the effect of suppressing the association is strengthened), and thus the decrease in the fluorescence intensity due to the association can be suppressed.

(2) $R^{11}$ to $R^{13}$ $R^{11}$ to $R^{13}$ each independently represent a hydrogen atom, an alkyl group, an aryl group, a heteroaryl group, an alkoxy group, an aryloxy group, an alkylthio group, an arylthio group, an amino group, or a halogen atom. Adjacent groups may be bonded to each other to form a 5-membered or 6-membered ring.

The alkyl group, the aryl group, the heteroaryl group, the alkoxy group, the aryloxy group, the alkylthio group, the arylthio group, the amino group, and the halogen atom, which can be adopted as $R^{11}$ to $R^{13}$ are respectively synonymous with the alkyl group, the aryl group, the heteroaryl group, the alkoxy group, the aryloxy group, the alkylthio group, the arylthio group, the amino group, and the halogen atom in the substituent group T described later, and the same applies to the preferred range thereof.

The alkyl group, the aryl group, the heteroaryl group, the alkoxy group, the aryloxy group, the alkylthio group, the arylthio group, and the amino group, which can be adopted as $R^{11}$ to $R^{13}$, may be each independently unsubstituted or may have a substituent.

Examples of the substituent which may be contained in the alkyl group, the aryl group, the heteroaryl group, the alkoxy group, the aryloxy group, the alkylthio group, the arylthio group, and the amino group, as $R^{11}$ to $R^{13}$, include the substituents in the substituent group T described later, and for example, an alkoxy group or a sulfo group is preferable.

Among $R^{11}$ to $R^{13}$, the 5-membered or 6-membered ring formed by bonding adjacent groups to each other may be either aromatic or aliphatic, and it is preferably aliphatic. In addition, it is preferable to form a 6-membered ring. The number of the above-described 5-membered or 6-membered rings in the compound is not particularly limited; however, it is preferably 1 or 2 and more preferably 1.

In a case of taking a case of n=3 as an example, preferred examples of the structure having a ring formed by bonding adjacent groups among $R^{11}$ to $R^{13}$ include the following structures. It is noted that in the following examples, $R^{11}$ to $R^{13}$ that do not form a ring structure are a hydrogen atom, and the ring structure is described as a structure that does not have a substituent, which are not limited thereto.

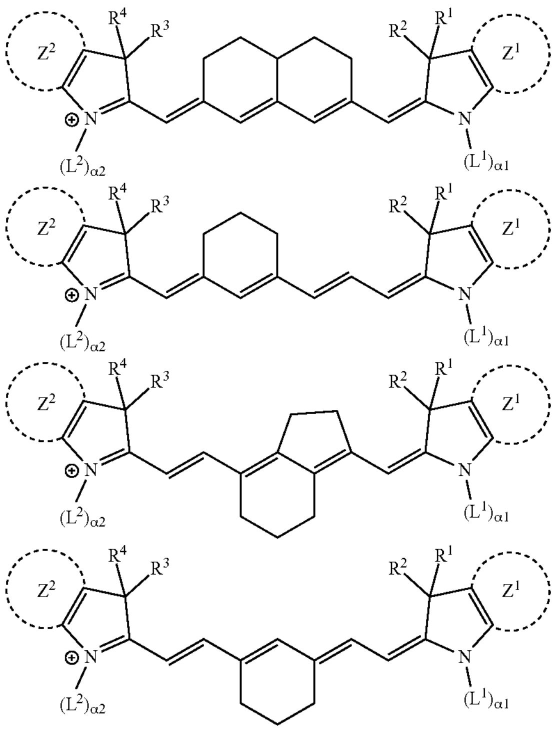

$R^{11}$ and $R^{13}$ possessed by the carbon atom bonded to the heterocyclic ring in which the ring $Z^2$ is fused is preferably a hydrogen atom.

$R^{12}$ and $R^{13}$ other than those described above are preferably a hydrogen atom, an alkyl group, an aryloxy group, or an arylthio group, and they are more preferably a hydrogen atom, an alkyl group, or an aryloxy group.

It is preferable that at least one of $R^{11}$ to $R^{13}$ is an aryloxy group or an arylthio group, and it is more preferable that at least one of $R^{12}$ or $R^{13}$ other than the $R^{13}$ possessed by the carbon atom bonded to the above-described indolenine ring is an aryloxy group or an arylthio group.

Among $R^{11}$ to $R^{13}$, $R^{11}$ and adjacent groups in $R^{12}$ and $R^{13}$ other than the $R^{13}$ possessed by the carbon atom bonded to the heterocyclic ring in which the ring $Z^2$ is fused are preferably bonded to each other to form a 5-membered or 6-membered ring and more preferably to form a 6-membered ring. In addition, it is preferable that the 5-membered or 6-membered ring is formed in a central portion of a bond connecting the heterocyclic ring in which the ring $Z^1$ is fused and the heterocyclic ring in which the ring $Z^2$ is fused. The ring formed at the central portion of the bond connecting the heterocyclic ring in which the ring $Z^1$ is fused and the heterocyclic ring in which the ring $Z^2$ is fused means a ring containing a carbon atom as a ring-constituting atom, in which the numbers of bonded atoms from the two heterocyclic rings are the same.

(3) $L^1$ and $L^2$ $L^1$ and $L^2$ each independently represent an alkyl group which may have a substituent or $-(CH_2-CH_2-O)_m-R^{21}$, where $R^{21}$ and m are respectively synonymous with $R^{21}$ and m described above.

Examples of the substituent which may be contained in the alkyl groups as $L^1$ and $L^2$ include an alkoxy group, a carboxy group, an alkoxycarbonyl group, an acyloxy group, a carbamoyl group, an acylamino group, a sulfo group, and a phosphono group, as well as a group consisting of a combination of these substituents. In addition, examples thereof include a substituent capable of being bonded to a biological substance described later. It is noted that the alkoxy group moiety in the alkoxy group, the carboxy group, the alkoxycarbonyl group, the acyloxy group, the aminocarbonyl group, the acylamino group, the sulfo group, and the phosphono group, as well as the group consisting of a combination of these substituents may have a substituent capable of being bonded to a biological substance described later.

The alkyl group which can be adopted as $L^1$ and $L^2$ is synonymous with an alkyl group in the substituent group T described later.

The unsubstituted alkyl group preferably has 1 to 6 carbon atoms, more preferably 1 to 4 carbon atoms, and still more preferably 1 to 3 carbon atoms.

The alkyl group moiety of the alkyl group having a substituent preferably has 1 to 10 carbon atoms, more preferably 1 to 8 carbon atoms, still more preferably 1 to 7 carbon atoms, even still more preferably 1 to 6 carbon atoms, and even still further preferably 1 to 5 carbon atoms. In addition, the number of atoms constituting the longest chain of the alkyl group having a substituent is preferably 3 to 14, more preferably 3 to 12, and still more preferably 3 to 10.

The alkyl group having a substituent, which can be adopted as $L^1$ and $L^2$, is preferably an alkyl group having, as a substituent, at least one of an alkoxy group, a carboxy group, a sulfo group, or a phosphono group, and more preferably an alkyl group having, as a substituent, at least one of a carboxy group or a sulfo group, from the viewpoint of further improving water solubility. Here, it may be an alkyl group having a substituent consisting of a combination of the above-described preferred substituents (the alkoxy group, the carboxy group, the sulfo group, and the phosphono group) and a group other than these substituents.

In addition, the form of the alkyl group having a substituent, which can be adopted by $R^1$ to $R^4$, can be also preferably applied.

As $-(CH_2-CH_2-O)_m-R^{21}$ which can be adopted as $L^1$ and $L^2$, the description for $-(CH_2-CH_2-O)_m-R^{21}$ in $R^1$ to $R^4$ can be preferably applied.

The $-(CH_2-CH_2-O)_m-R^{21}$ which can be adopted as $L^1$ and $L^2$ is preferably an alkyl group in which $R^{21}$ has, at the terminal, a substituent capable of being bonded to a carboxy group or a biological substance. In this case, the alkyl group may be directly substituted with a substituent capable of being bonded to a carboxy group or a biological substance, and it may be substituted with a group consisting of a combination of an alkoxycarbonyl group and a carboxy group or substituent capable of being bonded to a biological substance.

(4) Ring $Z^1$ and ring $Z^2$

A ring $Z^1$ and a ring $Z^2$ represent a 6-membered ring formed of a ring-constituting atom selected from a carbon atom and a nitrogen atom, may have a substituent, and may form a fused ring. From the viewpoint of further improving the fluorescence intensity, the ring $Z^1$ and the ring $Z^2$ are a monocyclic ring.

However, at least one of the ring $Z^1$ or the ring $Z^2$ is a benzene ring represented by General Formula (Zα) described later or a nitrogen-containing 6-membered ring satisfying the following definition (Zβ) described later.

The 6-membered ring formed of a ring-constituting atom selected from a carbon atom and a nitrogen atom, which can be adopted as the ring $Z^1$ and the ring $Z^2$ may be an aliphatic ring or an aromatic ring; however, it may be an aromatic ring.

Examples of the 6-membered ring include a hydrocarbon ring or a nitrogen-containing heterocyclic ring, and specific examples thereof include a benzene ring, a pyridine ring, a pyrimidine ring, a pyridazine ring, a pyrazine ring, and a 1,2,3- or 1,2,4-triazine ring, where a benzene ring or a pyridine ring is preferable. In addition, examples thereof also include an aliphatic ring having the same kind and position of the ring-constituting atom as these aromatic rings, depending on the method of describing the conjugated structure.

Examples of the substituent which may be contained in the 6-membered ring include a substituent in the substituent group T described later, where an alkyl group, an alkoxy group, an aryl group, a carboxy group, a sulfo group, a phosphono group, a sulfonamide group, a nitro group, or a halogen atom is preferable, and an alkyl group, a sulfo group, a sulfonamide group, a nitro group, or a halogen atom is more preferable.

From the viewpoint of improving water solubility and suppressing association, it is preferable that the ring $Z^1$ and the ring $Z^2$ each independently have one or more hydrophilic groups, and it is more preferable that they have at least one hydrophilic group per one ring constituting the ring $Z^1$ or the ring $Z^2$. For example, in a case where both the ring $Z^1$ and the ring $Z^2$ are naphthalene rings, it is meant to be more preferable that the number of rings constituting each of the ring $Z^1$ and the ring $Z^2$ is 2 and each of the ring $Z^1$ and the ring $Z^2$ has at least two hydrophilic groups. The upper limit value thereof is not particularly limited as long as it is allowed in terms of structure, and it can be appropriately adjusted in accordance with the number of hydrophilic groups in the compound as a whole, which will be described later.

The hydrophilic group is not particularly limited, and examples thereof include an alkoxy group having a substituent, a carboxy group, a sulfo group, and a phosphono group, where a sulfo group is preferable.

(A Benzene Ring Represented by General Formula (Zα))

General Formula (Zα)

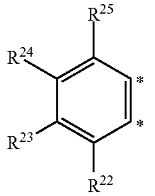

In the formula, $R^{22}$ represents an alkyl group, an alkoxy group, a sulfo group, a sulfonamide group, a nitro group, or a halogen atom.

$R^{23}$ to $R^{25}$ represent a hydrogen atom, an alkyl group, an alkoxy group, an aryl group, a sulfo group, a sulfonamide group, a nitro group, or a halogen atom, where adjacent groups may be bonded to each other to form a fused ring.

A structure represented by General Formula (Zα) is bonded, at a position of *, to a heterocyclic ring containing a nitrogen atom in General Formula (1) so that $R^{22}$ is at an ortho position with respect to the nitrogen atom to which $L^1$ or $L^2$ is bonded.

The alkyl group, the alkoxy group, the sulfo group, the sulfonamide group, the nitro group, and the halogen atom as $R^{22}$ are respectively synonymous with the alkyl group, the alkoxy group, the sulfo group, the sulfonamide group, the nitro group, and the halogen atom in the substituent group T described later.

The alkyl group, the alkoxy group, the sulfo group, the sulfonamide group, the nitro group, and the halogen atom as $R^{23}$ to $R^{25}$ are respectively synonymous with the alkyl group, the aryl group, the alkoxy group, the aryl group, the sulfo group, the sulfonamide group, the nitro group, and the halogen atom in the substituent group T described later.

The fused ring formed by bonding adjacent groups among $R^{23}$ to $R^{25}$ to each other is not particularly limited. However, preferred examples thereof include a benzene ring, and preferred examples of the ring $Z^1$ or the ring $Z^2$ include a naphthalene ring.

$R^{22}$ is preferably an alkyl group or a sulfo group.

$R^{23}$ to $R^{25}$ are preferably a hydrogen atom, a sulfo group, a nitro group, or a halogen atom, and they are more preferably a hydrogen atom, a sulfo group, or a halogen atom.

(Definition (Zβ))

The definition (Zβ): a nitrogen-containing 6-membered ring in which a ring-constituting atom located at an ortho position with respect to a nitrogen atom to which $L^1$ or $L^2$ is bonded is a nitrogen atom.

Examples of the nitrogen-containing 6-membered ring satisfying the above-described definition (Zβ) include a pyridine ring, a pyrimidine ring, a pyridazine ring, a pyrazine ring, and a 1,2,3- or 1,2,4-triazine ring, where a pyridine ring is preferable.

It is preferable that both the ring $Z^1$ and the ring $Z^2$ do not satisfy the definition (Zβ) at the same time.

The nitrogen-containing 6-membered ring satisfying the definition (Zβ) may have a substituent on the nitrogen atom which is a ring-constituting atom, including the ring-constituting nitrogen atom located at the ortho position with respect to the nitrogen atom to which $L^1$ or $L^2$ is bonded. Specific examples of the substituent which may be contained include the substituent which can be adopted as the above-described $R^{23}$ to $R^{25}$ or $L^1$, or $L^2$.

The nitrogen-containing 6-membered ring satisfying the definition (Zβ) may have a substituent on a ring-constituting atom other than the nitrogen atom, and specific examples thereof include the substituent which can be adopted as the above-described $R^{23}$ to $R^{25}$ or $L^1$, or $L^2$.

(5) n, α1, and α2 n is an integer of 1 to 3, and it is preferably 2 or 3.

α1 and α2 are 0 or 1. A case where α1 is 0 means that $L^1$ is not contained, and a case where α1 is 1 means that $L^1$ is contained. Similarly, a case where α2 is 0 means that $L^2$ is not contained, and a case where α2 is 1 means that $L^2$ is contained.

In a case where the ring $Z^1$ satisfies the above-described definition (Zβ), 0 is adopted as α1. In addition, in a case where the ring $Z^2$ satisfies the above-described definition (Zβ), 0 is adopted as α2.

At least one of the substituents contained in $L^1$ and $L^2$ and possessed by the ring-constituting nitrogen atom located at the ortho position in the above-described definition (Zβ) includes a substituent capable of being bonded to a carboxy group or a biological substance.

The compound represented by General Formula (1) can be bonded to a biological substance with the above-described carboxy group or a substituent capable of being bonded to a biological substance, whereby a targeted labeled biological substance can be obtained. It is noted that as a substituent capable of being bonded to a biological substance, a carboxy group can be easily derived by a conventional method.

In the present invention, the "substituent capable of being bonded to a biological substance" includes a substituent capable of being bonded to a biological substance, which is derived from a carboxy group.

As described above, since the compound represented by General Formula (1) is bonded to a biological substance with a substituent (specifically, a substituent contained in $L^1$ or $L^2$ or possessed by the ring-constituting nitrogen atom located at the ortho position in the definition (Zβ)) contained in a specific position in the cyanine skeleton structure, a labeled biological substance to be obtained is conceived to exhibit excellent fluorescence intensity, as described above.

It suffices that the number of groups having a substituent capable of being bonded to a carboxy group or a biological substance, among the substituents contained in $L^1$ and $L^2$ and possessed by the ring-constituting nitrogen atom located at the ortho position in the above-described definition (Zβ), is at least 1 or more in total, and the number thereof is preferably 1 to 3, more preferably 1 or 2, and still more preferably 1, from the viewpoint of the quantification of the substance to be detected.

From the viewpoint of further improving the fluorescence intensity, at least one of the substituents contained in $L^1$ and $L^2$ and possessed by the ring-constituting nitrogen atom located at the ortho position in the above-described definition (Zβ) preferably includes a substituent capable of being bonded to a carboxy group or a biological substance, and a structure represented by $-(CH_2-CH_2-O)_m-$, where m is 1 to 10. This is conceived to be because a proper hydrophilicity and a proper excluded volume effect are provided.

In addition, from the viewpoint of imparting sufficient hydrophilicity as the compound, the compound represented by General Formula (1) preferably has two or more hydrophilic groups, preferably has 2 to 8 hydrophilic groups, still more preferably has 2 to 6 hydrophilic groups, and particularly has 3 to 6 hydrophilic groups, as the compound as a whole.

As the hydrophilic group, the description for the hydrophilic group which can be adopted by the above-described ring $Z^1$ and ring $Z^2$ can be applied.

The position of the hydrophilic group is not particularly limited; however, examples of the group having the hydrophilic group include $R^{11}$ to $R^{13}$, the ring $Z^1$, the ring $Z^2$, $L^1$, and $L^2$.

In addition, in a case where at least one of $Z^1$ or $Z^2$ is the nitrogen-containing 6-membered ring satisfying the above-described definition (Zβ), at least two of the substituents (for example, $R^{31}$ of General Formula (2-3) described later) contained in $L^1$, $L^2$, and $R^1$ to $R^4$ and possessed by the ring-constituting nitrogen atom located at the ortho position in the above-described definition (Zβ) described later may be bonded to each other to form a ring containing a methine chain having a ring number of 2n+3 (a repetition number of 2l+3 in General Formulae (2-1) to (2-3) described later). Examples of the ring formed in this way include a structure represented by any one of General Formulae (5-1) to (5-4) described later. In a case where such a ring is formed, it is presumed that the fluorescence intensity can be further improved by suppressing the rotation (the rotation of the heterocyclic ring in which the ring $Z^1$ is fused and the rotation of the heterocyclic ring in which the ring $Z^2$ is fused).

<Compound Represented by any One of General Formulae (2-1) to (2-3)>

The compound represented by General Formula (1) according to the embodiment of the present invention is preferably represented by any of the following General Formulae (2-1) to (2-3).

General Formula (2-1)

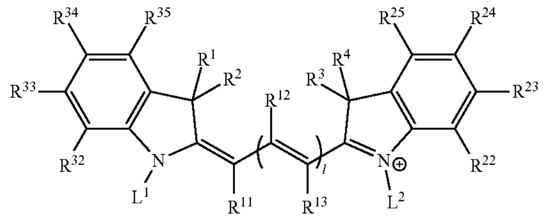

General Formula (2-2)

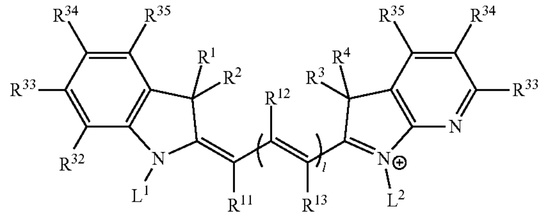

General Formula (2-3)

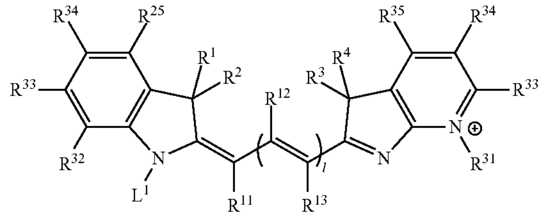

In the formulae, $R^{31}$ represents an alkyl group which may have a substituent or $-(CH_2-CH_2-O)_m-R^{21}$.

$R^{32}$ to $R^{35}$ represent a hydrogen atom, an alkyl group, an aryl group, a sulfo group, a sulfonamide group, a nitro group, or a halogen atom, where adjacent groups may be bonded to each other to form a fused ring.

$R^1$ to $R^4$, $R^{11}$ to $R^{13}$, $L^1$, $L^2$, and $R^{22}$ to $R^{25}$ are respectively synonymous with $R^1$ to $R^4$, $R^{11}$ to $R^{13}$, $L^1$, $L^2$, and $R^{22}$ to $R^{25}$ in General Formula (1), and the same applies to the preferred range thereof.

1 represents 2 or 3 where 1 is an integer.

Similar to the compound represented by General Formula (1), in the compound represented by any one of General Formulae (2-1) to (2-3) at least one of $L^1$, $L^2$, or $R^{31}$ contains a substituent capable of being bonded to a carboxy group or a biological substance.

However, it is not allowed that two of $L^1$, $L^2$, $R^1$ to $R^4$, and $R^{31}$ are bonded to each other to form a ring containing a methine chain having a repetition number of 2n+3.

However, the compound represented by any one of Formulae (2-1) to (2-3) is a neutral compound.

The alkyl group which may have a substituent, which can be adopted as $R^{31}$ and-$(CH_2—CH_2—O)_m—R^{21}$ are respectively synonymous with the alkyl group which may have a substituent, which can be adopted as $L^1$ or $L^2$, and-$(CH_2—CH_2—O)_m—R^{21}$.

The alkyl group, the aryl group, the sulfo group, the sulfonamide group, the nitro group, and the halogen atom, which can be adopted as $R^{32}$ to $R^{35}$, are respectively synonymous with the alkyl group, the aryl group, the sulfo group, the sulfonamide group, the nitro group, and the halogen atom, which can be adopted as $R^{23}$ to $R^{25}$ in General Formula (Zα).

<Compound Represented by any One of General Formulae (5-1) to (5-4)>

The compound represented by General Formula (1) according to the embodiment of the present invention is preferably represented by any of the following General Formulae (5-1) to (5-4).

General Formula (5-1)

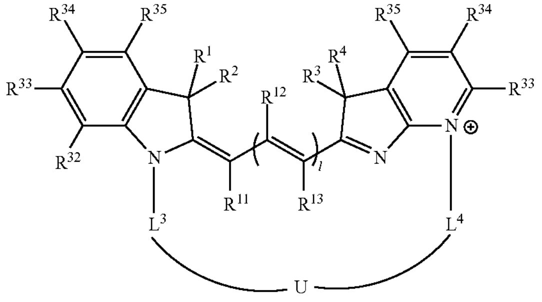

General Formula (5-2)

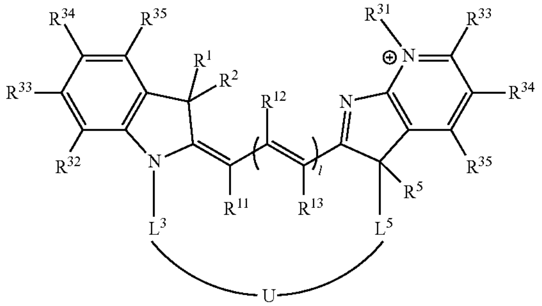

-continued

General Formula (5-3)

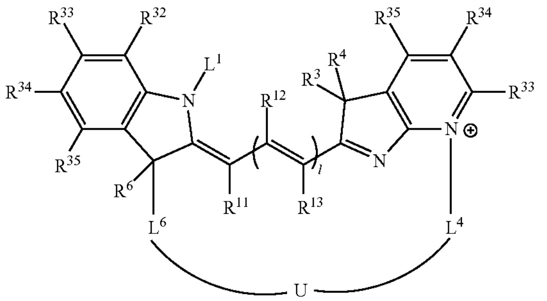

General Formula (5-4)

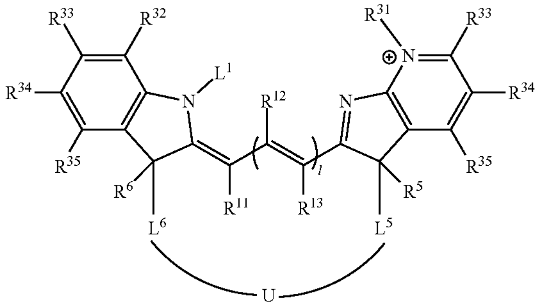

In the formulae, $R^1$ to $R^6$ represent an alkyl group which may have a substituent, an aryl group, a heteroaryl group, or $—(CH_2—CH_2—O)_m—R^{21}$.

$R^{31}$ is synonymous with $R^{31}$ in General Formulae (2-1) to (2-3), and the same applies to the preferred range thereof. That is, $R^{31}$ represents an alkyl group which may have a substituent or $—(CH_2—CH_2—O)_m—R^{21}$.

$R^{32}$ to $R^{35}$ are respectively synonymous with $R^{32}$ to $R^{35}$ in General Formulae (2-1) to (2-3), and the same applies to the preferred range thereof. That is, $R^{32}$ to $R^{35}$ represent a hydrogen atom, an alkyl group, an alkoxy group, an aryl group, a sulfo group, a sulfonamide group, a nitro group, or a halogen atom, where adjacent groups may be bonded to each other to form a fused ring.

1 represents 2 or 3 where 1 is an integer.

$L^3$ to $L^6$ represent an alkylene group or $—(CH_2—CH_2—O)_m$-alkylene-*. * represents a bonding position to U.

The linking group U represents a divalent linking group having the number of atoms of 1 to 100.

$R^{11}$ to $R^{13}$, $R^{21}$, $L^1$, and m are respectively synonymous with $R^{11}$ to $R^{13}$, $R^{21}$, $L^1$, and m in General Formula (1), and the same applies to the preferred range thereof unless otherwise specified.

At least one of $R^1$ to $R^6$, $L^1$, $R^{31}$, or $L^3$ to $L^6$ includes a structure represented by $—(CH_2—CH_2—O)_m—$, where m is synonymous with m described above.

at least one of $L^1$, $R^{31}$, $L^3$ to $L^6$, or the linking group U contains a substituent capable of being bonded to a carboxy group or a biological substance, However, the compound represented by any one of Formulae (5-1) to (5-4) is a neutral compound.

The alkylene group which can be adopted as $L^3$ corresponds to an alkylene group obtained by removing one hydrogen atom or one substituent from an alkyl group having a substituent which can be adopted as $L^1$ and $L^2$. The alkylene group which can be adopted as $L^4$ corresponds to an alkylene group obtained by removing one hydrogen atom or one substituent from an alkyl group which is a substituent, which may be contained on the ring-constituting nitrogen atom of the nitrogen-containing 6-membered ring satisfying the definition (Zβ). The alkylene group which can be adopted as $L^5$ and $L^6$ corresponds to an alkylene group obtained by removing one hydrogen atom or one substituent from an alkyl group having a substituent which can be adopted as $R^1$ to $R^4$.

As the number of carbon atoms of the alkylene group moiety of the alkylene group which can be adopted as $L^3$ to $L^6$, the description for the number of carbon atoms of the alkyl group moiety of the alkyl group having a substituent in $L^1$ and $L^2$ can be preferably applied.

The $-(CH_2-CH_2-O)_m$-alkylene-* which can be adopted as $L^3$ corresponds to $-(CH_2-CH_2-O)_m$-alkylene obtained by removing one hydrogen atom or one substituent from the alkyl group as $R^{21}$, among the $-(CH_2-CH_2-O)_m-R^{21}$ which can be adopted as $L^1$ and $L^2$ ($R^{21}$ represents an alkyl group having a substituent).

The $-(CH_2-CH_2-O)_m$-alkylene-* which can be adopted as $L^4$, corresponds to $-(CH_2-CH_2-O)_m$-alkylene obtained by removing one hydrogen atom or one substituent from the $-(CH_2)-CH_2-O)_m-R^{21}$ ($R^{21}$ represents an alkyl group having a substituent) which is a substituent which may be contained on the ring-constituting nitrogen atom of the nitrogen-containing 6-membered ring satisfying the definition (Zβ).

The $-(CH_2-CH_2-O)_m$-alkylene-* which can be adopted as $L^5$ and $L^6$ corresponds to $-(CH_2-CH_2-O)_m$-alkylene obtained by removing one hydrogen atom or one substituent from the $-(CH_2-CH_2-O)_m-R^{21}$ which can be adopted as $R^1$ to $R^4$ ($R^{21}$ represents an alkyl group having a substituent).

In the $-(CH_2-CH_2-O)_m$-alkylene-* which can be adopted as $L^3$ to $L^6$, m is preferably 1 to 10 and more preferably 1 to 8, and as the number of carbon atoms of the alkylene group moiety, the description for the number of carbon atoms of the alkyl group moiety of the alkyl group having a substituent in $R^1$ to $R^4$ can be preferably applied.

From the viewpoint of further improving the fluorescence intensity, all of $L^3$ to $L^6$ contained in the compound (that is, each of $L^3$ to $L^6$ contained in the compound) preferably include a structure represented by $-(CH_2-CH_2-O)_m-$. In a case of specifically making a description with respect to each general formula, it is preferable that the structure represented by $-(CH_2-CH_2-O)_m$ is included in $L^3$ and $L^5$ in General Formula (5-2), $L^4$ and $L^6$ in General Formula (5-3), and $L^5$ and $L^6$ in General Formula (5-4).

Further, in General Formulae (5-1) to (5-3), it is preferable that at least one of $R^1$ or $R^2$ and at least one of $R^3$ or $R^4$ includes a structure represented by $-(CH_2-CH_2-O)_m-$. In a case of specifically making a description with respect to each general formula, it is preferable that at least one of $R^1$ or $R^2$ and at least one of $R^3$ or $R^4$ in General Formula (5-1), at least one of $R^1$ or $R^2$ in General Formula (5-2), and at least one of $R^3$ or $R^4$ in General Formula (5-3) include a structure represented by $-(CH_2-CH_2-O)_m-$. m is synonymous with m in General Formula (1).

This means that it is preferable that both of the two heterocyclic rings located at both ends of the polymethine chain in General Formulae (5-1) to (5-3) satisfy the following condition I.

(Condition I)

In an $sp^3$ carbon atom that does not have a substituent that is bonded to the linking group U, among the $sp^3$ carbon atoms which are ring-constituting atoms of the heterocyclic ring, at least one substituent on the $sp^3$ carbon atom includes a structure represented by $-(CH_2-CH_2-O)_m-$.

The total number of atoms constituting the linking group U is 1 to 100, and it is preferably 10 to 90, more preferably 20 to 90, and still more preferably 30 to 80.

The linking group U is preferably a divalent linking group formed by bonding three or more selected from an alkylene group, $-O-$, $-NR^{50}-$, $-COO-$, $-CONR^{50}-$, and $-SO_2NR^{50}-$, where $R^{50}$ represents a hydrogen atom or an alkyl group.

The number of carbon atoms in the alkylene moiety of the alkylene group which can be adopted as the linking group U is preferably 1 to 10, more preferably 1 to 8, still more preferably 1 to 7, particularly preferably 1 to 6, and most preferably 1 to 5.

As the alkyl group which can be adopted as $R^{50}$, the description for the alkyl group as $R^1$ to $R^4$ can be preferably applied, where $R^{50}$ is preferably a hydrogen atom.

The number of the above-described alkylene group, $-O-$, $-NR^{50}-$, $-COO-$, $-CONR^{50}-$, and $-SO_2NR^{50}-$, constituting the linking group U, is preferably 3 to 11, more preferably 3 to 7, still more preferably 3 to 5, and particularly preferably 3.

In the linking group U, the connecting portion to $L^3$ to $L^6$ is preferably $-O-$, $-NR^{50}-$, $-COO-$, $-CONR^{50}-$, or $-SO_2NR^{50}-$. That is, the linking group U is preferably bonded to the alkylene groups of $L^3$ to $L^6$ through $-O-$, $-NR^{50}-$, $-COO-$, $-CONR^{50}-$, or $-SO_2NR^{50}-$, which constitutes the linking group U. In the linking group U, it is more preferable that connecting portions to $L^3$ to $L^6$ are $-O-$, $-NR^{50}-$, $-COO-$, $-CONR^{50}-$, or $-SO_2NR^{50}-$, and that the linking group U is a divalent linking group in which the connecting portions are bonded to each other through an alkylene group.

The linking group U is preferably a divalent linking group having a substituent capable of being bonded to a carboxy group or a biological substance. Examples of the site in the linking group U, where the substituent capable of being bonded to a carboxy group or a biological substance is located, include an alkylene group and an alkyl group as $R^{50}$, where an alkylene group is preferable.

In the linking group U, the substituent capable of being bonded to a carboxy group or a biological substance may be directly bonded to the alkylene group or the alkyl group as $R^{50}$, or it may be bonded through a linking group ZZZ.

Examples of the linking group ZZZ include an alkylene group, $-NR^{60}-$, $-COO-$, $-CONR^{60}-$, and-$(CH_2-CH_2-O)_m-$, as well as a group consisting of a combination of these substituents. The number of substituents to be combined is, for example, preferably 2 to 7 and more preferably 2 to 5.

Here, $R^{60}$ is a hydrogen atom or an alkyl group, and it is preferably a hydrogen atom. As the alkyl group which can be adopted as $R^{60}$, the description for the alkyl group in $R^{50}$ can be preferably applied. However, it is not allowed that the alkyl group which can be adopted as $R^{60}$ has a substituent capable of being bonded to a carboxy group or a biological substance.

m represents the repetition number, and it is preferably 1 to 10, more preferably 1 to 8, and still more preferably 1 to 4.

$R^{12}$ and $R^{13}$ other than the $R^{13}$ possessed by the carbon atom bonded to the heterocycle in which ring $Z^2$ is fused are preferably a hydrogen atom, an alkyl group, an aryloxy group, or an arylthio group, more preferably a hydrogen atom, an alkyl group, or an aryloxy group, and still more preferably a hydrogen atom.

Specific examples of the compound according to the embodiment of the present invention, which is represented by General Formula (1), will be shown; however, the present invention is not limited to these compounds. In the following specific examples, the sulfo group may adopt a salt structure in which a hydrogen atom is dissociated. In the following specific examples, $mPEG_4$ and $PEG_4$ respectively indicate the following structures, X represents a hydrogen atom, a chlorine atom, or a bromine atom, and Me represents a methyl group. However, $PEG_4$ is bonded to a nitrogen atom on the carbon atom side, or the ring-constituting atom of the heterocyclic ring in which the ring $Z^1$ or the ring $Z^2$ is fused.

$$mPEG = -(CH_2-CH_2-O)_4-Me$$

$$mPEG = -(CH_2-CH_2-O)_4-$$

-continued

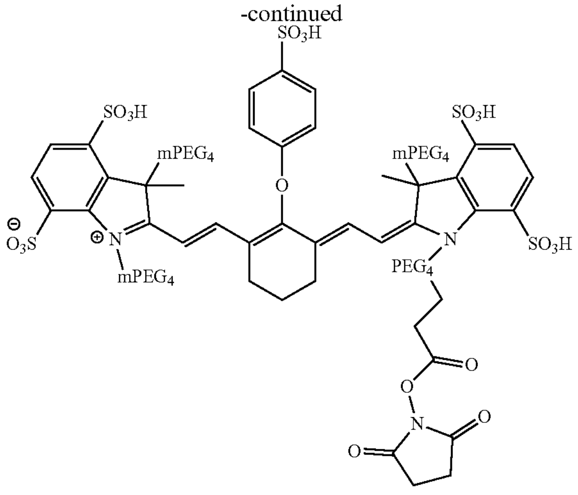

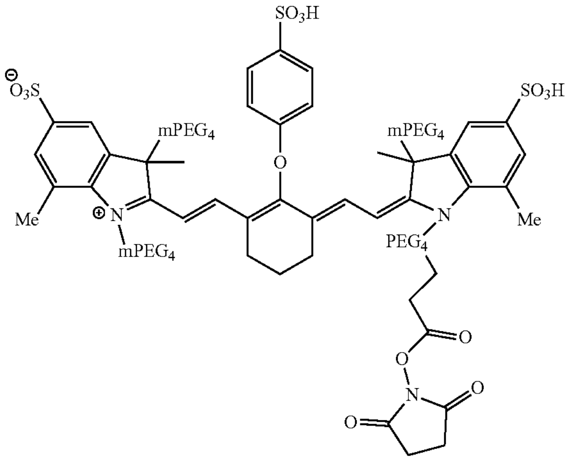

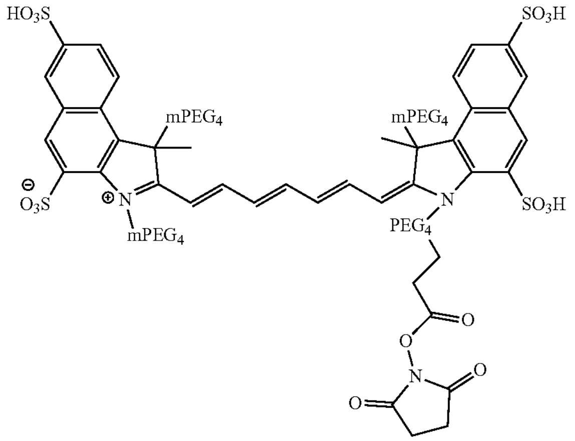

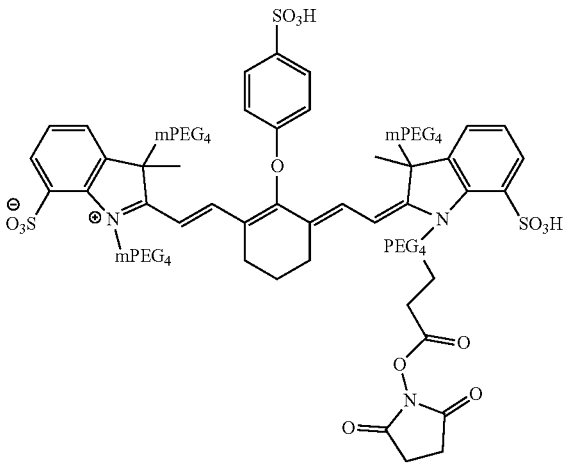

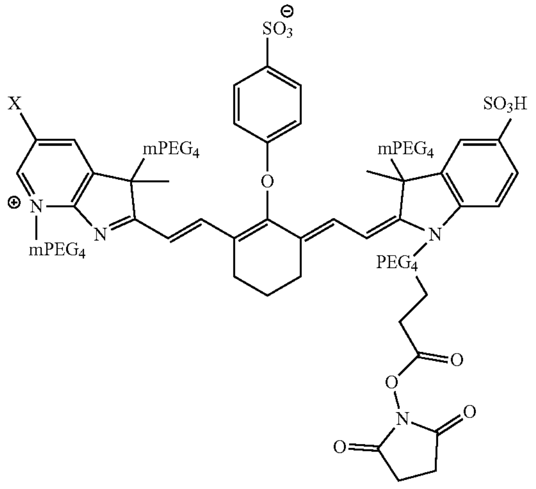

-continued
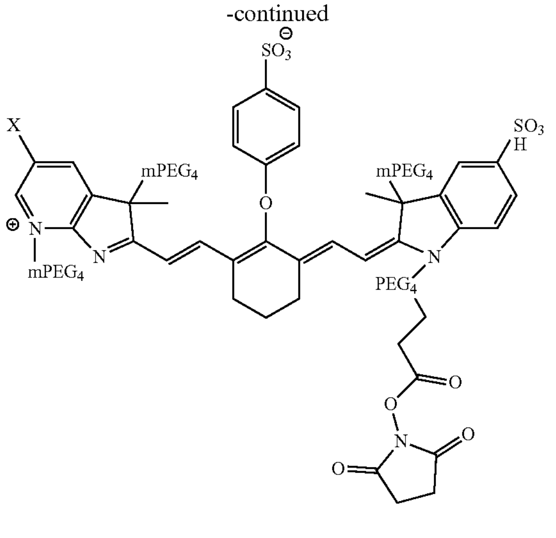
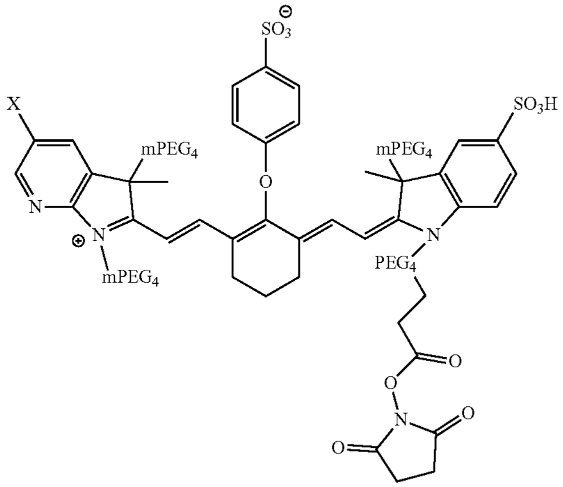
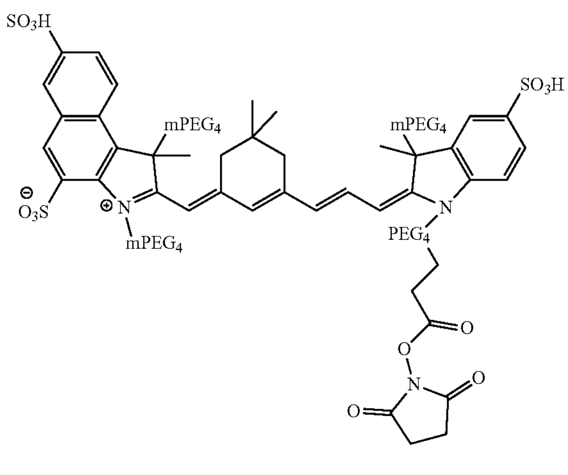
-continued
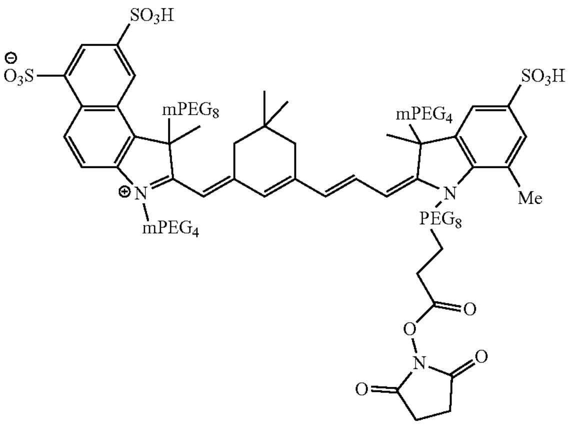
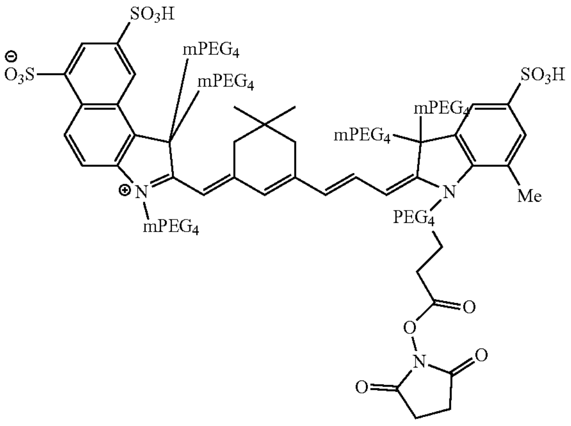
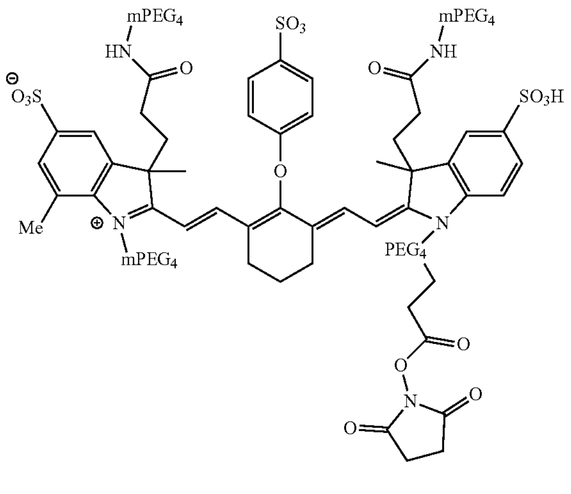

-continued
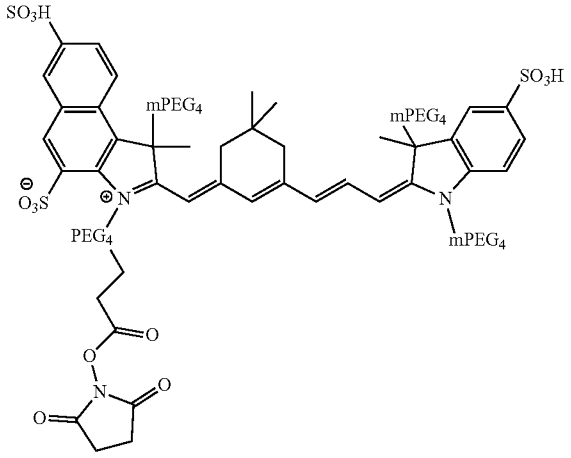
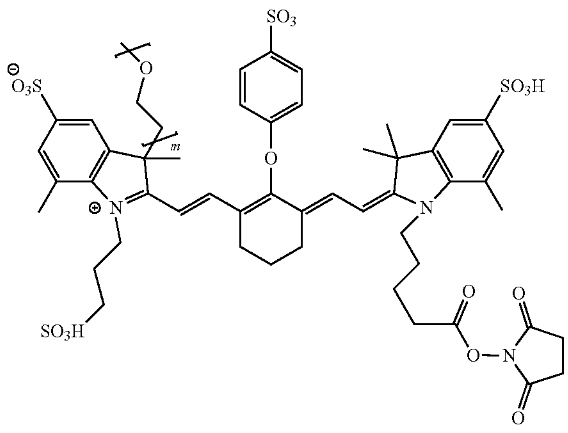
m = 8
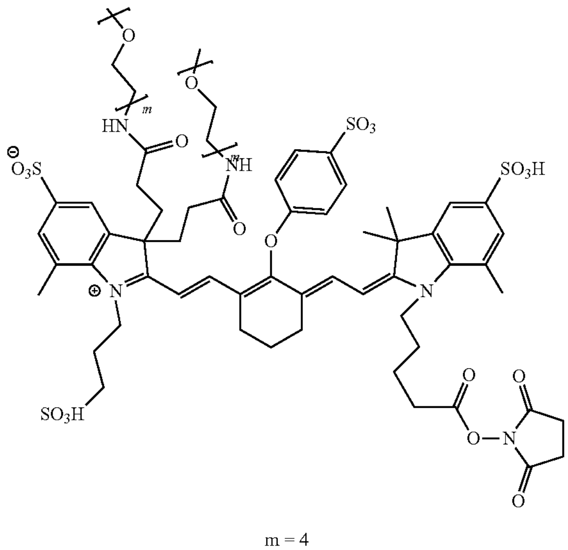
m = 4
-continued
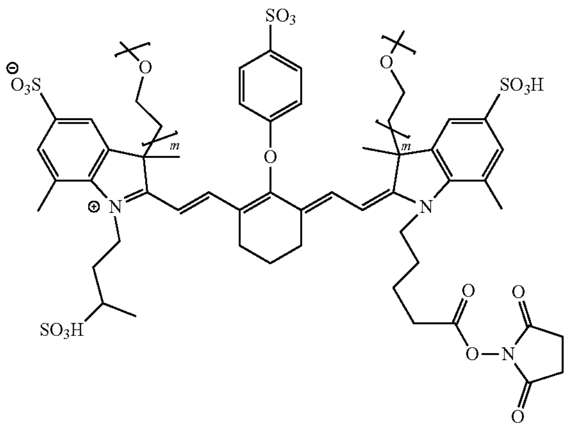
m = 4
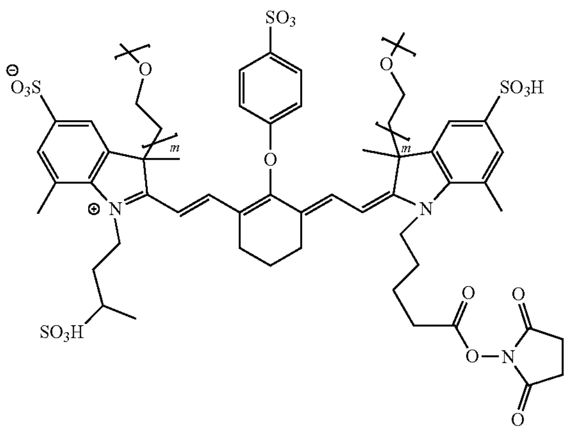
m = 10
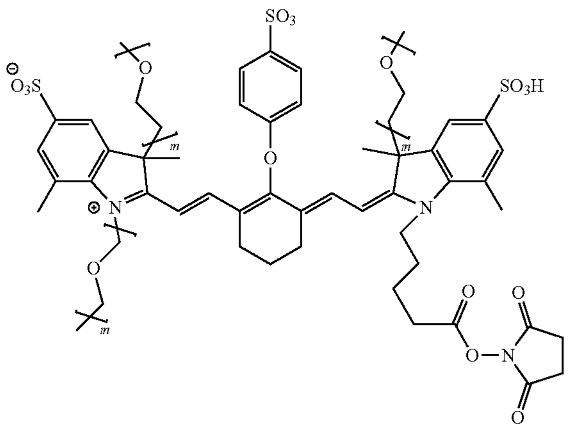
m = 4

-continued
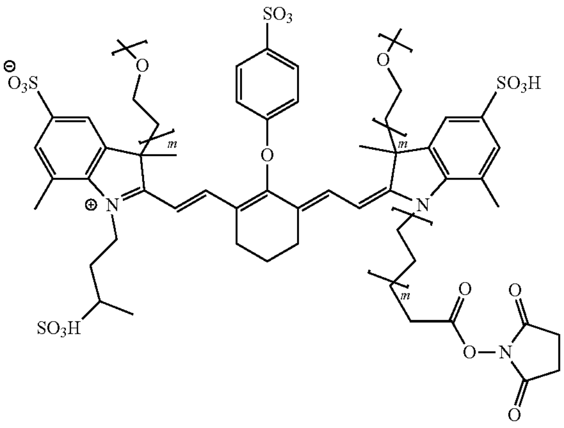
m = 4
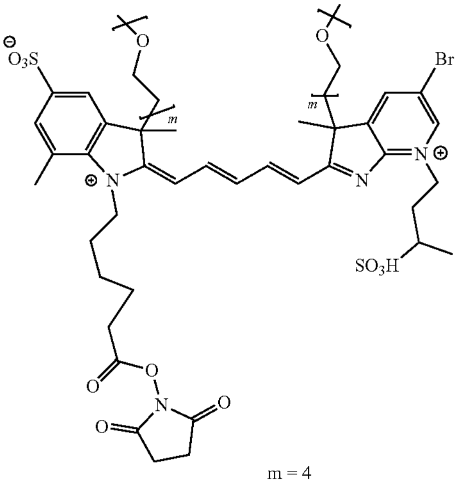
m = 4
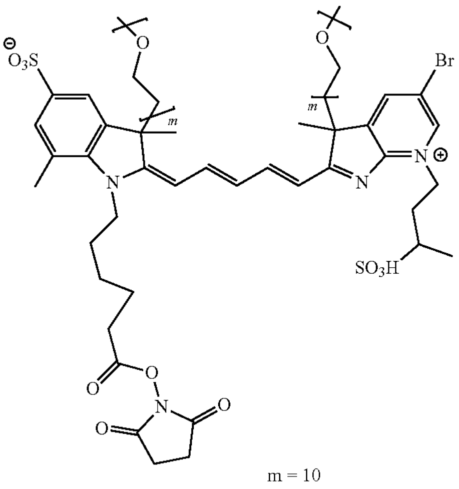
m = 10
-continued
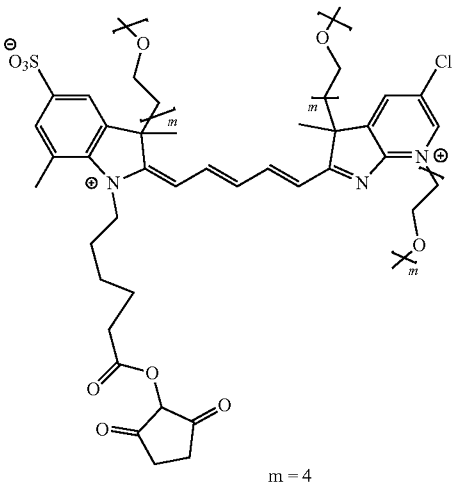
m = 4
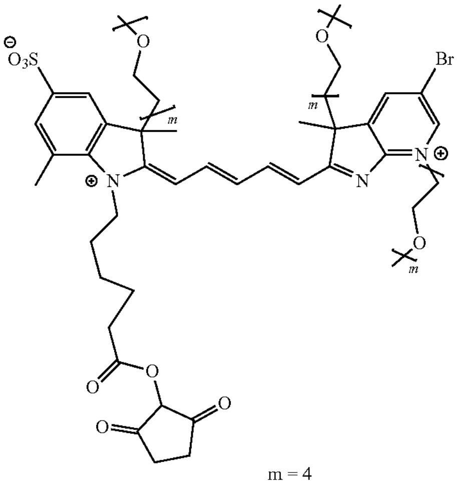
m = 4
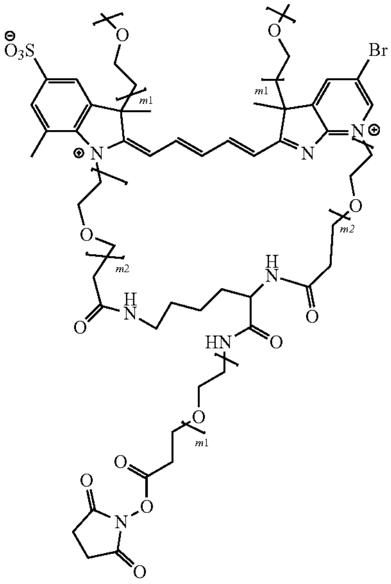
m1 = 4
m2 = 1

-continued
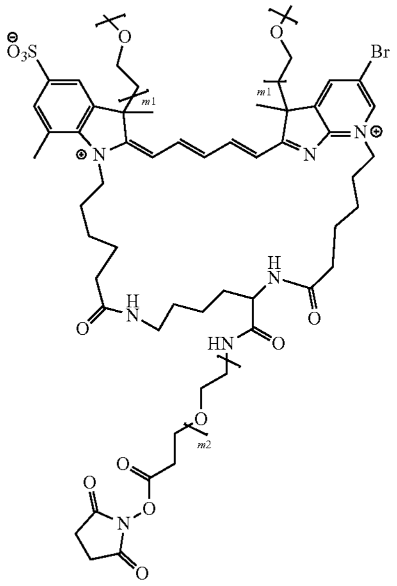
m1 = 4
m2 = 1
-continued
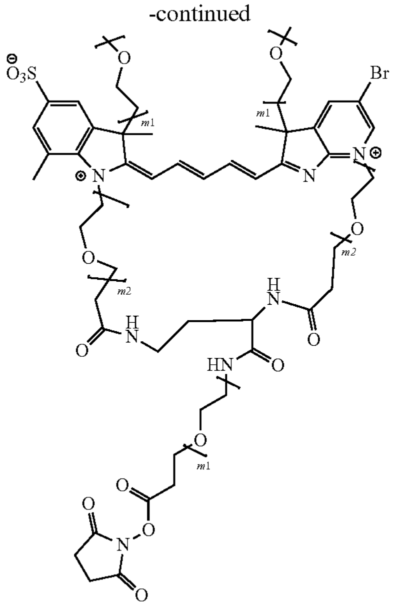
m1 = 4
m2 = 1
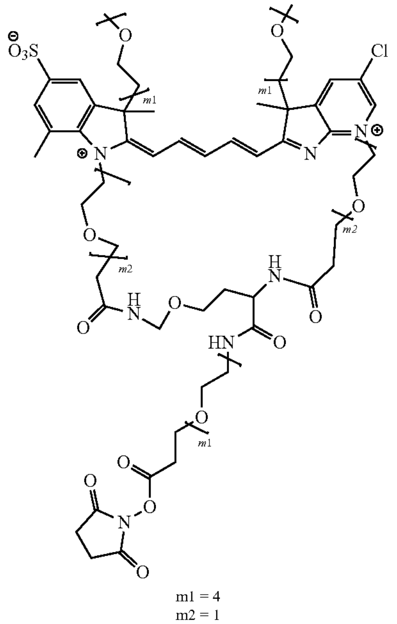
m1 = 4
m2 = 1
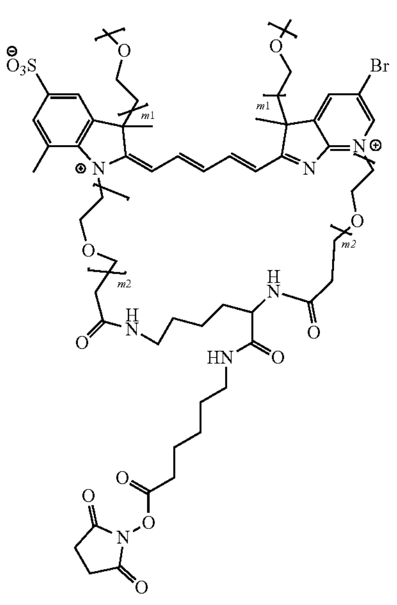
m1 = 4
m2 = 4

-continued

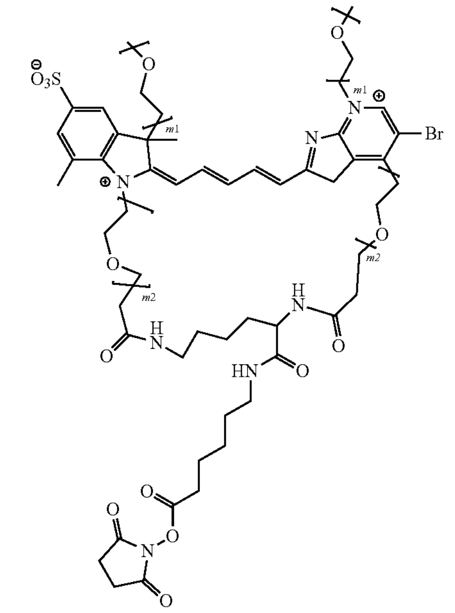

m1 = 4
m2 = 1

-continued

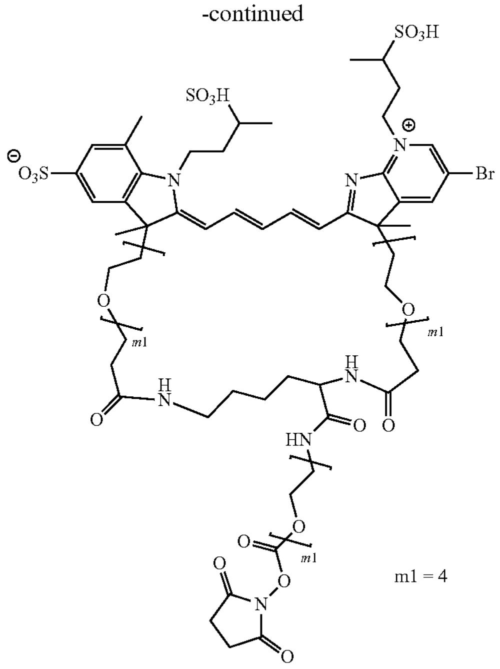

m1 = 4

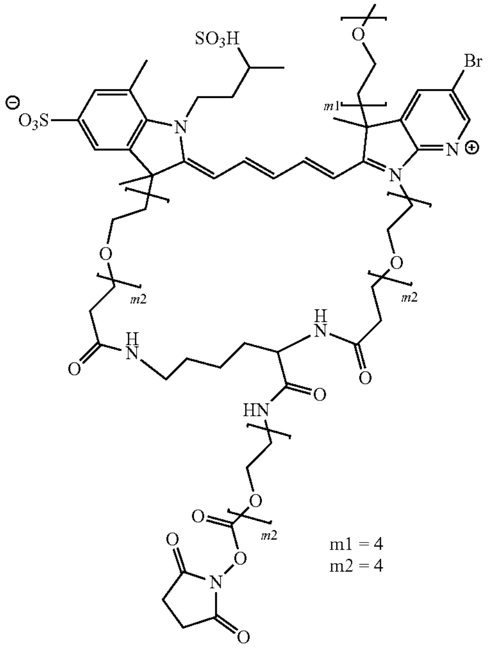

m1 = 4
m2 = 4

The compound according to the embodiment of the present invention, which is represented by General Formula (1), can be bonded to a biological substance such as a protein, a peptide, an amino acid, a nucleic acid, a sugar chain, or a lipid, with a substituent capable of being bonded to a biological substance, where the substituent is at least one of the substituents contained in $L^1$ and $L^2$ and possessed by the ring-constituting nitrogen atom located at the ortho position in the definition (Zβ).

The substituent capable of being bonded to a biological substance can be used without particular limitation as long as it is a group for acting (including adhering) or bonding to a biological substance, and examples thereof include the substituents described in WO2002/026891A. Among them, preferred examples thereof include an N-hydroxysuccinimide ester (NHS) structure, a succinimide structure, a maleimide structure, an azido group, an acetylene group, a peptide structure (a polyamino acid structure), a long-chain alkyl group (preferably having 12 to 30 carbon atoms), and a quaternary ammonium group.

Specific examples of the compound having at least a substituent capable of being bonded to a biological substance as at least any one of the substituents contained in $L^1$ and $L^2$ and possessed by the ring-constituting nitrogen atom located at the ortho position in the definition (Zβ), among the compounds according to the embodiment of the present invention represented by General Formula (1), include an exemplary compound in the labeled biological substance described later. Further, specific examples thereof also include a form of an exemplary compound of the compound according to the embodiment of the present invention represented by General Formula (1), in which a substituent capable of being bonded to a biological substance is contained and which is shown as an exemplary compound of the labeled biological substance described later. It is noted that the present invention is not limited to these compounds. For example, in the specific examples thereof, a group having a dissociative hydrogen atom such as a specific hydrophilic group Pi may adopt a salt structure by a hydrogen atom being dissociated therefrom.

The compound according to the embodiment of the present invention, which is represented by General Formula (1), can be synthesized by a known method except that the compound structure is the structure regulated by General Formula (1). For example, the methods described in WO2009/078970A and WO2013/130761A, and the like can be mentioned.

A compound having a substituent capable of being bonded to a biological substance can be synthesized by a known method except that the compound structure is the structure regulated by General Formula (1). For example, Bioconjugate Techniques (Third Edition, written by Greg T. Hermanson) can be referred to.

<<Labeled Biological Substance>>

The labeled biological substance according to the embodiment of the present invention is a substance in which the compound according to the embodiment of the present invention, which is represented by General Formula (1), is bonded to a biological substance. Since the compound according to the embodiment of the present invention, which is represented by General Formula (1), has fluorescence and exhibits an absorption wavelength peak suitable for color development in the near infrared range and an excellent fluorescence intensity, it can be preferably used for a labeled biological substance. The bond between the compound represented by General Formula (1) and a biological substance may have a form in which the compound represented by General Formula (1) and the biological substance are directly bonded or a form in which they are linked through a linking group.

Preferred examples of the biological substance include a protein, a peptide, an amino acid, a nucleic acid, a sugar chain, and a lipid. Preferred examples of the protein include an antibody, and preferred examples of the lipid include a phospholipid, a fatty acid, sterol, where a phospholipid is more preferable.

Among the above biological substances, the clinically useful substance is not particularly limited, but examples thereof include immunoglobulins such as immunoglobulin (Ig) G, IgM, IgE, IgA, and IgD; plasma proteins such as complement, C-reactive protein (CRP), ferritin, $\alpha_1$ microglobulin, $\beta_2$ microglobulin, and antibodies thereof; tumor markers such as α-fetoprotein, carcinoembryonic antigen (CEA), prostate acid phosphatase (PAP), carbohydrate antigen (CA) 19-9, and CA-125, and antibodies thereof; hormones such as luteinizing hormone (LH), follicle-stimulating hormone (FSH), human ciliated gonadotropin (hCG), estrogen, and insulin, and antibodies thereof; and viral infection-related substances of viruses such HIV and ATL, hepatitis B virus (HBV)-related antigens (HBs, HBe, and HBc), human immunodeficiency virus (HIV), adult T-cell leukemia (ATL), and antibodies thereof.

The examples thereof further include bacteria such as *Corynebacterium diphtheriae, Clostridium botulinum, mycoplasma*, and *Treponema pallidum*, and antibodies thereof; protozoa such as *Toxoplasma, Trichomonas, Leishmania, Trypanosoma*, and malaria parasites, and antibodies thereof; embryonic stem (ES) cells such as ELM3, HM1, KH2, v6.5, v17.2, v26.2 (derived from mice, 129, 129/SV, C57BL/6, and BALB/c), and antibodies thereof; antiepileptic drugs such as phenytoin and phenobarbital; cardiovascular drugs such as quinidine and digoxin; anti-asthma drugs such as theophylline; drugs such as antibiotics such as chloramphenicol and gentamicin, and antibodies thereof; and enzymes, extracellular toxins (for example, styrelidine O), and the like, and antibodies thereof. In addition, antibody fragments such as Fab'2, Fab, and Fv can also be used.

Examples of the specific form in which the compound according to the embodiment of the present invention, which is represented by General Formula (1), (hereinafter, also abbreviated as the compound (1) and the biological substance interact with each other to be bonded include the forms described below, i) non-covalent bond (for example, hydrogen bond, ionic bond including chelate formation) or covalent bond between a peptide in the compound (1) and a peptide in the biological substance, ii) van der Waals force between a long-chain alkyl group in the compound (1) and a lipid bilayer, a lipid, or the like in the biological substance, iii) an amide bond formed by reacting an N-hydroxysuccinimide ester (NHS ester) in the compound (1) with an amino group in the biological substance, iv) a thioether bond formed by reacting a maleimide group in the compound (1) with a sulfanyl group (—SH) in the biological substance, and v) a formation of a triazole ring, which is formed by the Click reaction between an azido group in the compound (1) and an acetylene group in the biological substance, or the Click reaction between an acetylene group in the compound (1) and an azido group in the biological substance.

In addition to the forms of the i) to v), the bond can be formed according to another form, for example, which is described in "Lucas C. D. de Rezende and Flavio da Silva Emery, A Review of the Synthetic Strategies for the Development of BODIPY Dyes for Conjugation with Proteins, Orbital: The Electronic Journal of Chemistry, 2013, Vol 5, No. 1, p. 62-83". Further, the method described in the same document can be appropriately referred to for the preparation of the labeled biological substance according to the embodiment of the present invention.

Hereinafter, specific examples of the labeled biological substance according to the embodiment of the present invention, obtained from a compound among the compounds according to the embodiment of the present invention represented by General Formula (1) and from a biological substance that is bonded to the compound with interaction, are shown, where the compound is a compound having at least a substituent capable of being bonded to a biological substance as at least any one of the substituents contained in $L^1$ and $L^2$ and possessed by the ring-constituting nitrogen atom located at the ortho position in the definition (Zβ). However, the present invention is not limited to these compounds or the like, In the following specific examples, a group having a dissociative hydrogen atom such as a sulfo group may adopt a salt structure by a hydrogen atom being dissociated therefrom. The $mPEG_4$ and $PEG_4$ are respectively synonymous with the $mPEG_4$ and the $PEG_4$ in the specific example of the compound represented by General Formula (1) described above.

| Compound example | Product (bonding mode) |
|---|---|
| 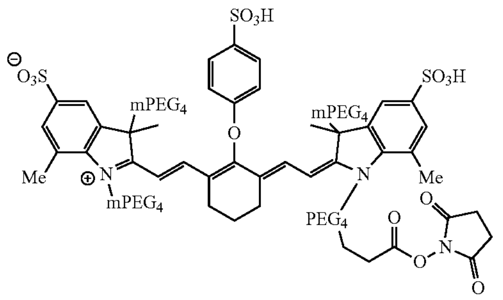 NHS ester structure | 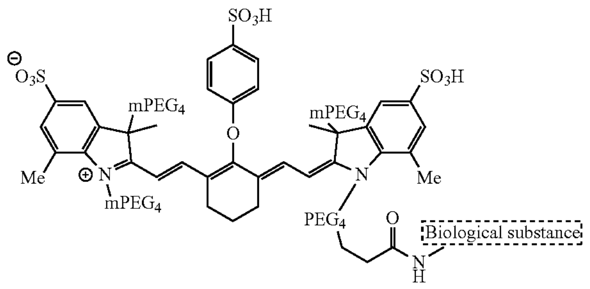 Bonding through amino group of biological substance |
| 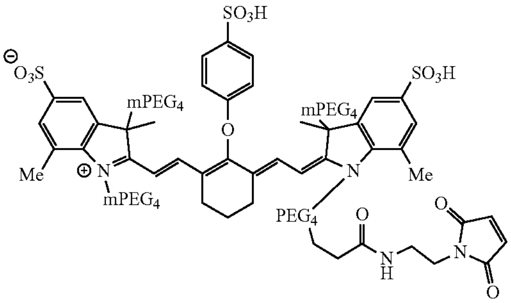 Maleimide structure | 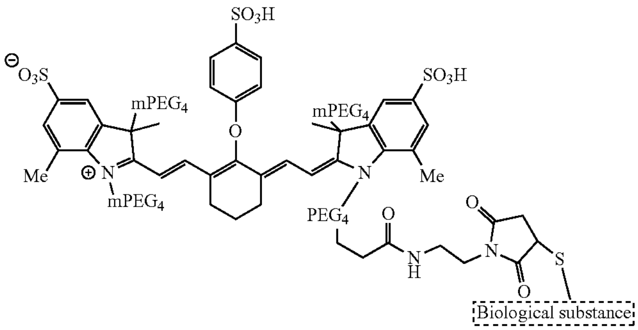 Bonding through sulfanyl group of biological substance |
| 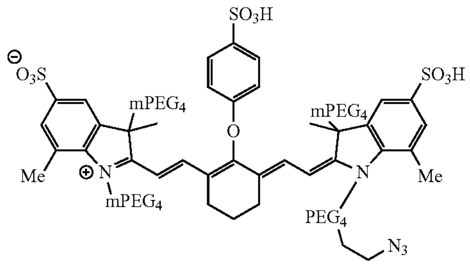 Azide structure | 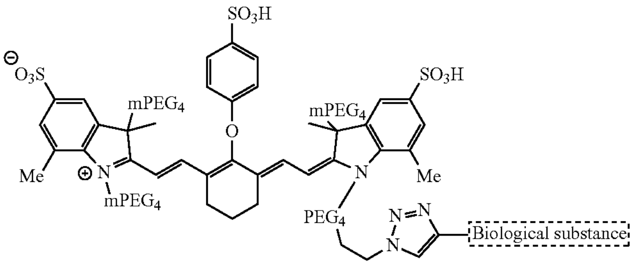 Click reaction through acetylene group of biological substance |
| 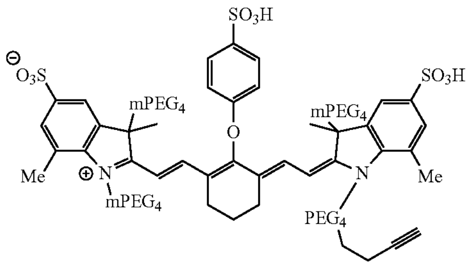 Acetylene structure | 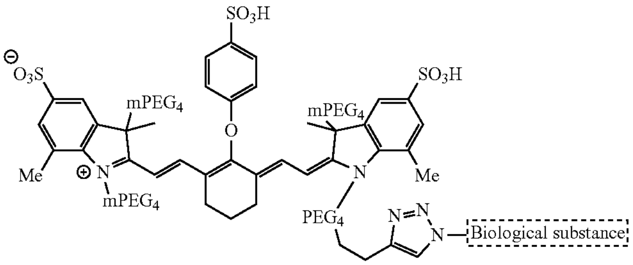 Click reaction through azide group of biological substance |

-continued

| Compound example | Product (bonding mode) |
| --- | --- |
| 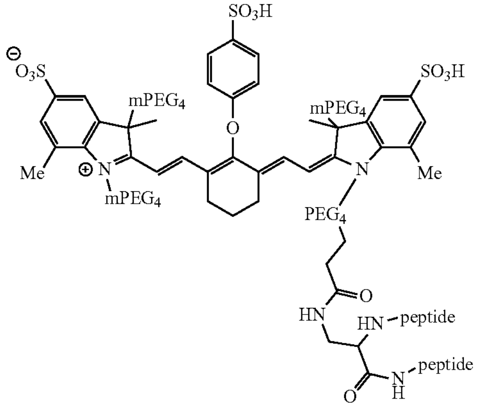<br>Peptide structure (polyamino acid structure) | 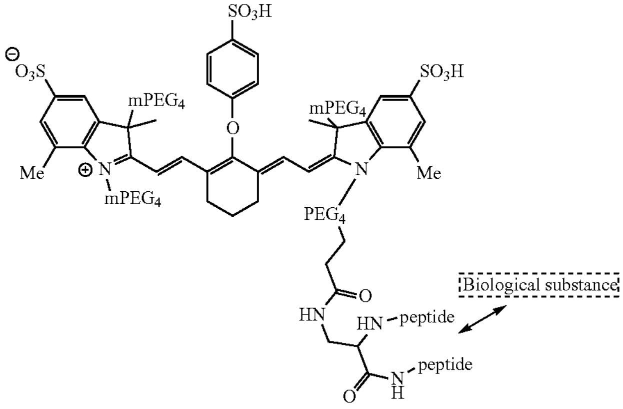<br>Bonding through peptide of biological substance |
| 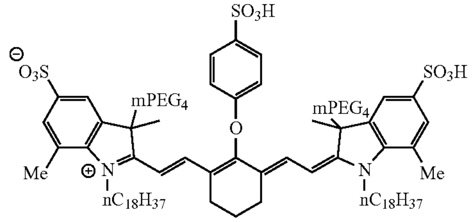<br>Long-chain alkyl group | Van der Waals force through lipid bilayer, phospholipid, or the like of biological substance |

<Reagent Containing Labeled Biological Substance>

In the reagent containing the labeled biological substance according to the embodiment of the present invention, the form of the labeled biological substance according to the embodiment of the present invention, for example, a solution form dissolved in an aqueous medium such as physiological saline and a phosphate buffer solution, and a solid form such as a fine particle powder or a lyophilized powder, is not particularly limited and can be appropriately selected depending on the purpose of use.

For example, in a case where the labeled biological substance according to the embodiment of the present invention is used as a fluorescence labeling reagent, it can be used as a reagent containing the labeled biological substance having any one of the forms described above.

<Use Application of Labeled Biological Substance>

The labeled biological substance according to the embodiment of the present invention, obtained from the compound according to the embodiment of the present invention, which is represented by General Formula (1), can exhibit an excellent fluorescence intensity and stably detect fluorescence emitted from the labeled biological substance excited by light irradiation. As a result, the labeled biological substance according to the embodiment of the present invention can be applied to various techniques using the fluorescence labeling, and it can be suitably used, for example, as a fluorescence labeling reagent in a multicolor WB or a reagent for in vivo fluorescence imaging.

The fluorescence detection carried out using the labeled biological substance according to the embodiment of the present invention usually includes the following processes (i) to (iii) or (iv) to (vii). The fluorescence detection including the processes (i) to (iii) corresponds to the direct method using a primary antibody fluorescently labeled with the compound according to the embodiment of the present invention, and the fluorescence detection including the processes (iv) to (vii) corresponds to the indirect method using a secondary antibody fluorescently labeled with the compound according to the embodiment of the present invention.

(i) The process of preparing each of the following (a) and (b)

(a) A sample containing a targeted biological substance (hereinafter, also referred to as a "target biological substance")

(b) A labeled biological substance according to the embodiment of the present invention (hereinafter, also referred to as a "labeled biological substance A according to the embodiment of the present invention") obtained by bonding the biological substance (hereinafter, also referred to as a "primary biological substance") capable of binding to the target biological substance in the above (a) to the compound according to the embodiment of the present invention (ii) The process of preparing a conjugate (hereinafter, also referred to as a "fluorescently labeled conjugate A") in which the target biological substance in the above (a) is bonded to the primary biological substance in the labeled biological substance A according to the embodiment of the present invention in the above (b)

(iii) The process of irradiating the fluorescently labeled conjugate A with light having the range of the wavelength which is absorbed by the labeled biological substance A according to the embodiment of the present invention, and detecting the fluorescence emitted by the labeled biological substance A according to the embodiment of the present invention (iv) The process of preparing each of the following (c) to (e)

(c) A sample containing a target biological substance (d) A biological substance capable of binding to the target biological substance in the above (c) (hereinafter, also referred to as a "primary biological substance")

(e) A labeled biological substance according to the embodiment of the present invention (hereinafter, also referred to as a "labeled biological substance B according to the embodiment of the present invention") obtained by bonding the biological substance (hereinafter, also referred to as a "secondary biological substance") capable of binding to the primary biological substance in the above (d) to the compound according to the embodiment of the present invention (hereinafter, also referred to as a "labeled biological substance B according to the embodiment of the present invention")

(v) The process of preparing a conjugate (hereinafter, also referred to as a "conjugate b") in which the target biological substance in the above (c) is bonded to the primary biological substance of the above (d)

(vi) The process of preparing a conjugate (hereinafter, also referred to as a "fluorescently labeled conjugate B2") in which the primary biological substance in the conjugate (b) is bonded to the secondary biological substance in the labeled biological substance B according to the embodiment of the present invention (vii) The process of irradiating the fluorescently labeled conjugate B2 with light having the range of the wavelength which is absorbed by the labeled biological substance B according to the embodiment of the present invention, and detecting the fluorescence emitted by the labeled biological substance B according to the embodiment of the present invention Examples of the biological substance (the primary biological substance) capable of binding to the target biological substance and the biological substance (the secondary biological substance) capable of binding to the primary biological substance include the biological substances in the labeled biological substance according to the embodiment of the present invention. The above biological substance can be appropriately selected in accordance with the target biological substance (a biological substance in the test object) or the primary biological substance, and a biological substance capable of specifically binding to the biological substance in the test object or to the primary biological substance can be selected.

Examples of the protein among the target biological substances include a protein, which is a so-called disease marker. The disease marker is not particularly limited, and examples thereof include α-fetoprotein (AFP), protein induced by vitamin K absence or antagonist II (PIVKA-II), breast carcinoma-associated antigen (BCA) 225, basic fetoprotein (BFP), carbohydrate antigen (CA) 15-3, CA19-9, CA72-4, CA125, CA130, CA602, CA54/61 (CA546), carcinoembryonic antigen (CEA), DUPAN-2, elastase 1, immunosuppressive acidic protein (IAP), NCC-ST-439, γ-seminoprotein (γ-Sm), prostate specific antigen (PSA), prostatic acid phosphatase (PAP), nerve specific enolase (NSE), Iba1, amyloid β, tau, flotillin, squamous cell carcinoma associated antigen (SCC antigen), sialyl LeX-i antigen (SLX), SPan-1, tissue polypeptide antigen (TPA), serial Tn antigen (STN), cytokeratin (CYFRA) pepsinogen (PG), C-reactive protein (CRP), serum amyloid A protein (SAA), myoglobin, creatine kinase (CK), troponin T, and ventricular muscle myosin light chain I.

The target biological substance may be a bacterium. Examples of the bacterium include a bacterium to be subjected to a cellular and microbiological test, which is not particularly limited. Specific examples thereof include *Escherichia coli, Salmonella, Legionella*, and bacteria causing problems in public health.

The target biological substance may be a virus. Although the virus is not particularly limited, examples of the virus antigen include hepatitis virus antigens such as hepatitis C and B virus antigens, p24 protein antigen of HIV virus, and pp65 protein antigen of cytomegalovirus (CMV), and E6 and E7 proteins of human papillomavirus (HPV).

In the above (i) or (iv), the sample containing the target biological substance is not particularly limited and can be prepared according to a conventional method.

In addition, the labeled biological substance according to the embodiment of the present invention is not particularly limited and can be prepared by bonding a biological substance capable of binding to a target biological substance to the compound according to the embodiment of the present invention, according to a conventional method. The form of the bond and the reaction to form the bond are as described above in the labeled biological substance according to the embodiment of the present invention.

In the above (v), the target biological substance may be directly bonded to the primary biological substance or may be bonded through another biological substance which is different from the target biological substance and the primary biological substance. Further, in the above (vi), the primary biological substance in the conjugate b may be directly bonded to the secondary biological substance in the labeled biological substance B according to the embodiment of the present invention or may be bonded through another biological substance which is different from the primary biological substance and the secondary biological substance.

The labeled biological substance according to the embodiment of the present invention can be used as a fluorescently labeled antibody in both the direct method and the indirect method but is preferably used as a fluorescently labeled antibody in the indirect method.

In the above (ii) or (v) and the (vi), the binding of the labeled biological substance or the like according to the embodiment of the present invention to the target biological substance is not particularly limited and can be carried out according to a conventional method.

In the above (iii) or (vii), the wavelength for exciting the labeled biological substance according to the embodiment of the present invention is not particularly limited as long as the wavelength is an emission wavelength (excitation wavelength) capable of exciting the labeled biological substance according to the embodiment of the present invention.

Since the labeled biological substance using a compound in which n is 1 among the compounds (1) according to the embodiment of the present invention has an absorption maximum wavelength in the vicinity of 585 nm (560 to 620 nm), the range of the wavelength of light to be emitted is preferably 530 to 650 nm and more preferably 550 to 630 nm. The labeled biological substance using this compound can be suitably used as a labeled biological substance that exhibits an excellent fluorescence intensity with respect to a light source for excitation wavelength in the vicinity of 600 nm in the visible range.

Since the labeled biological substance using a compound in which n is 2 among the compounds (1) according to the embodiment of the present invention has an absorption maximum wavelength in the vicinity of 685 nm (660 to 720 nm), the range of the wavelength of light to be emitted is preferably 630 to 750 nm and more preferably 650 to 730 nm. The labeled biological substance using this compound can be suitably used as a labeled biological substance that exhibits an excellent fluorescence intensity with respect to a light source for excitation wavelength in the vicinity of 700 nm in the near infrared range of the multicolor WB.

Since the labeled biological substance using a compound in which n is 3 among the compounds (1) according to the embodiment of the present invention has an absorption maximum wavelength in the vicinity of 785 nm (760 to 820 nm), the range of the wavelength of light to be emitted is preferably 730 to 850 nm and more preferably 750 to 830 nm. The labeled biological substance using this compound can be suitably used as a labeled biological substance that exhibits an excellent fluorescence intensity with respect to a light source for excitation wavelength in the vicinity of 800 nm in the near infrared range of the multicolor WB.

The fluorescence excitation light source used in the present invention is not particularly limited as long as it emits an emission wavelength (excitation wavelength) capable of exciting the labeled biological substance according to the embodiment of the present invention, and for example, various laser light sources can be used. In addition, various optical filters can be used to obtain a preferred excitation wavelength or detect only fluorescence.

Other matters in the above (i) to (vii) are not particularly limited, and conditions of a method, a reagent, a device, and the like, which are generally used in the fluorescence detection using fluorescence labeling, can be appropriately selected.

Further, regarding the processes other than the above (i) to (vii) as well, conditions of a method, a reagent, a device, and the like, which are generally used, can be appropriately selected in accordance with various methods using fluorescence labeling.

For example, in the multicolor WB using the labeled biological substance according to the embodiment of the present invention, it is possible to detect a target biological substance with excellent fluorescence intensity by preparing a blotted membrane according to a method generally used for a target biological substance (protein separation by electrophoresis, blotting to a membrane, and blocking of a membrane) and using the labeled biological substance according to the embodiment of the present invention as a labeled antibody (preferably, as a secondary antibody).

—Substituent Group T—

In the present invention, the preferred substituents include those selected from the following substituent group T.

In addition, in the present invention, in a case where it is simply described as a substituent, the substituent refers to the substituent group T, and in a case where an individual group, for example, an alkyl group is only described, a corresponding group in the substituent group T is preferably applied.

Further, in the present specification, in a case where an alkyl group is described separately from a cyclic (cyclo) alkyl group, the alkyl group is used to include a linear alkyl group and a branched alkyl group. On the other hand, in a case where an alkyl group is not described separately from a cyclic alkyl group, and unless otherwise specified, the alkyl group is used to include a linear alkyl group, a branched alkyl group, and a cycloalkyl group. This also applies to groups (alkoxy group, alkylthio group, alkenyloxy group, and the like) containing a group capable of having a cyclic structure (alkyl group, alkenyl group, alkynyl group, and the like) and compounds containing a group capable of having a cyclic structure. In a case where a group is capable of forming a cyclic skeleton, the lower limit of the number of atoms of the group forming the cyclic skeleton is 3 or more and preferably 5 or more, regardless of the lower limit of the number of atoms specifically described below for the group that can adopt this structure, In the following description for the substituent group T, a group having a linear or branched structure and a group having a cyclic structure, such as an alkyl group and a cycloalkyl group, are sometimes described separately for clarity.

The groups included in the substituent group T include the following groups.

An alkyl group (preferably having 1 to 30 carbon atoms, more preferably 1 to 20 carbon atoms, still more preferably 1 to 12 carbon atoms, still more preferably 1 to 8 carbon atoms, still more preferably 1 to 6 carbon atoms, and particularly preferably 1 to 3 carbon atoms), an alkenyl group (preferably having 2 to 30 carbon atoms, more preferably 2 to 20 carbon atoms, still more preferably 2 to 12 carbon atoms, still more preferably 2 to 6 carbon atoms, and even still more preferably 2 to 4 carbon atoms), an alkynyl group (preferably having 2 to 30 carbon atoms, still more preferably 2 to 20 carbon atoms, still more preferably 2 to 12 carbon atoms, still more preferably 2 to 6 carbon atoms, and even still more preferably 2 to 4 carbon atoms), a cycloalkyl group (preferably having 3 to 20 carbon atoms), a cycloalkenyl group (preferably having 5 to 20 carbon atoms), an aryl group (it may be a monocyclic group or may be a fused ring group (preferably a fused group in which 2 to 6 rings are fused); in a case of a fused ring group, it consists of a 5-membered to 7-membered ring; and the aryl group preferably has 6 to 40 carbon atoms, more preferably 6 to 30 carbon atoms, still more preferably 6 to 26 carbon atoms, and particularly preferably 6 to 10 carbon atoms), a heterocycle group (it has, as a ring-constituting atom, at least one nitrogen atom, an oxygen atom, a sulfur atom, a phosphorus atom, a silicon atom, or selenium atom, may be a monocyclic ring, or may be a fused ring group (preferably a fused group in which 2 to 6 rings are fused); in a case of a monocyclic group, the monocyclic ring is preferably a 5-membered to 7-membered ring and more preferably a 5-membered or 6-membered ring; the heterocycle group preferably has 2 to 40 carbon atoms and more preferably 2 to 20 carbon atoms; and the heterocyclic group includes an aromatic heterocyclic group (a heteroaryl group) and an aliphatic heterocyclic group (an aliphatic heterocyclic group), an alkoxy group (preferably having 1 to 20 carbon atoms, and more preferably having 1 to 12 carbon atoms), an alkenyloxy group (preferably having 2 to 20 carbon atoms, and more preferably having 2 to 12 carbon atoms), and an alkynyloxy group (preferably having 2 to 20 carbon atoms, and more preferably having 2 to 12 carbon atoms), a cycloalkyloxy group (preferably having 3 to 20 carbon atoms), an aryloxy group (preferably having 6 to 40 carbon atoms, more preferably having 6 to 26 carbon atoms, and still more preferably having 6 to 14 carbon atoms), a heterocyclic oxy group (preferably having 2 to 20 carbon atoms), a polyalkyleneoxy group (preferably having 2 to 40 carbon atoms and more preferably 2 to 20 carbon atoms).

An alkoxycarbonyl group (preferably having 2 to 20 carbon atoms), a cycloalkoxycarbonyl group (preferably having 4 to 20 carbon atoms), an aryloxycarbonyl group (preferably having 6 to 20 carbon atoms), an amino group (preferably having 0 to 20 carbon atoms; the amino group includes an unsubstituted amino group ($—NH_2$), a (mono- or di-) alkylamino group, a (mono- or di-) alkenylamino group, a (mono- or di-) alkynylamino group, a (mono- or di-) cycloalkylamino group, a (mono- or di-) cycloalkenylamino group, a (mono- or di-) arylamino group, or a (mono- or di-) heterocyclic amino group, where each of the above groups substituting an unsubstituted amino group has the same definition as the corresponding group in the substituent group T), a sulfamoyl group (preferably having 0 to 20 carbon atoms; the sulfamoyl group is preferably an alkyl, cycloalkyl, or aryl sulfamoyl group), an acyl group (preferably having 1 to 20 carbon atoms, and more preferably having 2 to 15 carbon atoms), an acyloxy group (preferably having 1 to 20 carbon atoms), a carbamoyl group (preferably having 1 to 20 carbon atoms; the carbamoyl group is preferably an alkyl, cycloalkyl, or aryl carbamoyl group).

An acylamino group (preferably having 1 to 20 carbon atoms), a sulfonamide group (preferably having 0 to 20 carbon atoms and preferably an alkyl, cycloalkyl, or aryl sulfonamide group), an alkylthio group (preferably having 1 to 20 carbon atoms and more preferably 1 to 12 carbon atoms), a cycloalkylthio group (preferably having 3 to 20 carbon atoms), an arylthio group (preferably having 6 to 40 carbon atoms, more preferably 6 to 26 carbon atoms, and still more preferably 6 to 14 carbon atoms), a heterocyclic thio group (preferably having 2 to 20 carbon atoms), an alkyl, cycloalkyl, or aryl sulfonyl group (preferably having 1 to 20 carbon atoms).

A silyl group (preferably having 1 to 30 carbon atoms and more preferably 1 to 20 carbon atoms, and preferably substituted with an alkyl, aryl, alkoxy, or aryloxy), a silyloxy group (preferably having 1 to 20 carbon atoms and preferably substituted with an alkyl, aryl, alkoxy, or aryloxy), a hydroxy group, a cyano group, a nitro group, a halogen atom (for example, a fluorine atom, a chlorine atom, a bromine atom or an iodine atom), an oxygen atom (specifically replacing $>CH_2$ which constitutes a ring with $>C{=}O$), a carboxy group ($—CO_2H$), a phosphono group [$—PO(OH)_2$], a phosphonooxy group [$—O—PO(OH)_2$], a sulfo group ($—SO_3H$), a boric acid group [$—B(OH)_2$], an onio group (an ammonio group including a cyclic ammonio group, which contains a sulfonio group or a phosphonio group, and preferably has 0 to 30 carbon atoms and more preferably 1 to 20 carbon atoms), a sulfanyl group (—SH), an amino acid residue, or a polyamino acid residue.

Further, examples thereof include the above-described alkyl group, alkenyl group, alkynyl group, cycloalkyl group, cycloalkenyl group, aryl group, heterocycle group, alkoxy group, alkenyloxy group, alkynyloxy group, cycloalkyloxy group, aryloxy group, heterocyclic oxy group, alkoxycarbonyl group, cycloalkoxycarbonyl group, aryloxycarbonyl group, amino group, sulfamoyl group, acyl group, acyloxy group, carbamoyl group, acylamino group, sulfonamide group, alkylthio group, cycloalkylthio group, arylthio group, heterocyclic thio group, and an alkyl, cycloalkyl, and aryl sulfonyl group, which have, as a substituent, a carboxy group, a phosphono group, a sulfo group, an onio group, an amino acid residue, a polyamino acid residue, or a $—(CH_2—CH_2—O)_m$-alkyl group (m is synonymous with m in $R^1$ to $R^6$).

The substituent selected from the substituent group T is more preferably an alkyl group, an alkenyl group, a cycloalkyl group, an aryl group, a heterocycle group, an alkoxy group, a cycloalkoxy group, an aryloxy group, an alkoxycarbonyl group, a cycloalkoxycarbonyl group, an amino group, an acylamino group, a cyano group or a halogen atom, and particularly preferably an alkyl group, an alkenyl group, an aryl group, a heterocycle group, an alkoxy group, an alkoxycarbonyl group, an amino group, an acylamino group, or a cyano group.

The substituent selected from the substituent group T also includes a group obtained by combining a plurality of the above groups, unless otherwise specified. For example, in a case where a compound, a substituent, or the like contains an alkyl group, an alkenyl group, or the like, the alkyl group, the alkenyl group, or the like may be substituted or unsubstituted. In addition, in a case where a compound, a substituent, or the like contains an aryl group, a heterocyclic ring group, or the like, the aryl group, the heterocyclic ring group, or the like may be a monocyclic ring or a fused ring moiety, and may be substituted or unsubstituted.

EXAMPLES

Hereinafter, the present invention will be described in more detail based on Examples, but the present invention is not limited thereto. It is noted that room temperature means 25° C.

Compounds (1) to (11) and comparative compounds (1) and (6), used in Examples, are shown below.

It is noted that in the compounds of Examples, the sulfo group may include a salt structure (for example, a potassium salt, a sodium salt, a triethylamine (TEA) salt, or an N,N-diisopropylethylamine (DIPEA) salt), even unless otherwise specified. m means an average repetition number. All of the compounds were synthesized using a compound in which the first decimal place of the average repetition number was 0 as a raw material.

Compound (1)

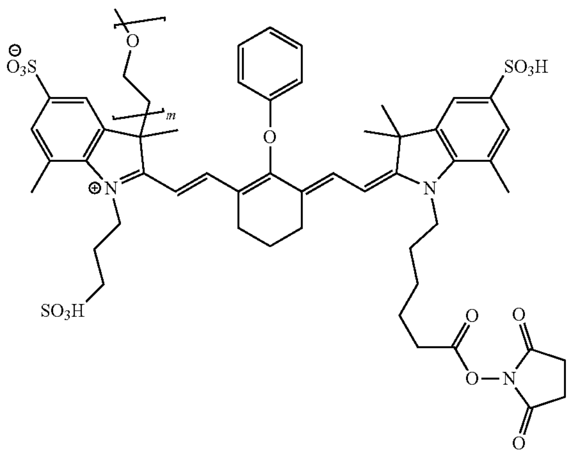

m = 8

-continued
(Compound 2)
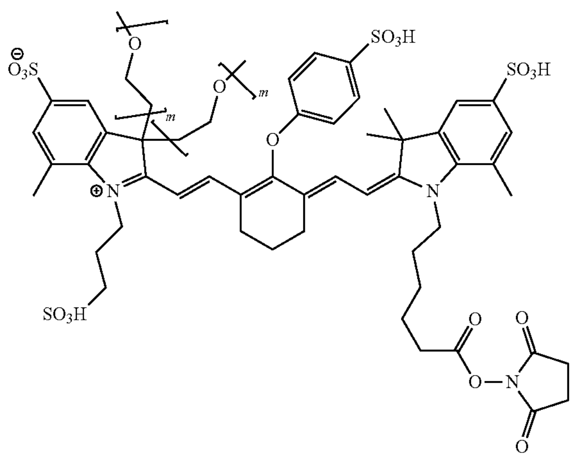
$m = 4$
(Compound 3)
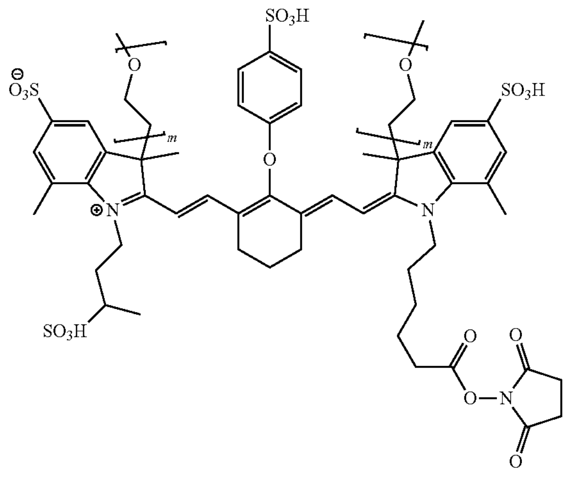
$m = 4$
(Compound 4)
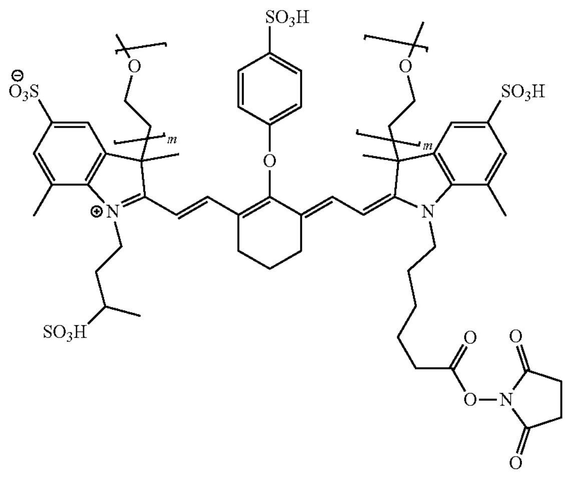
$m = 10$
-continued
(Compound 5)
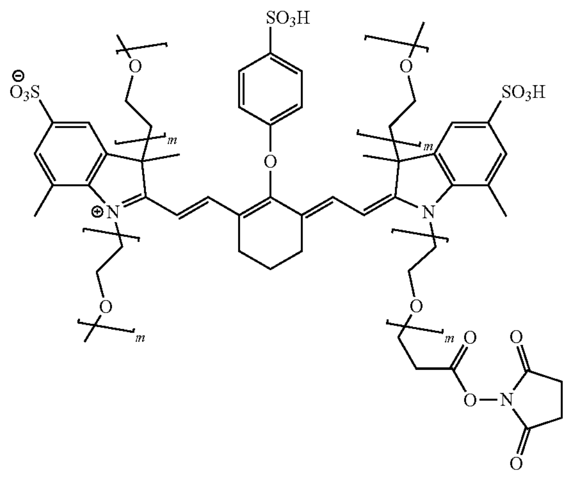
$m = 4$
(Compound 6)
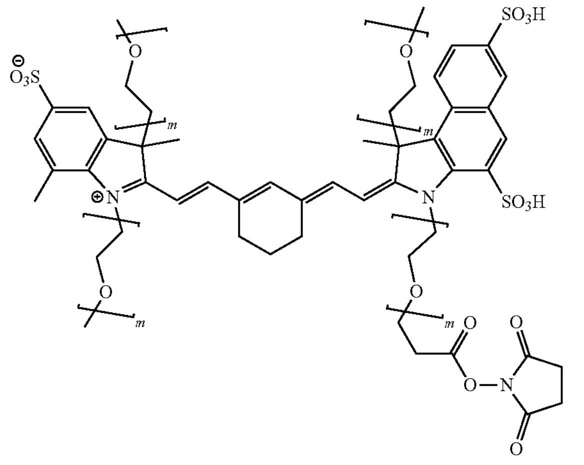
$m = 4$
Compound (7)
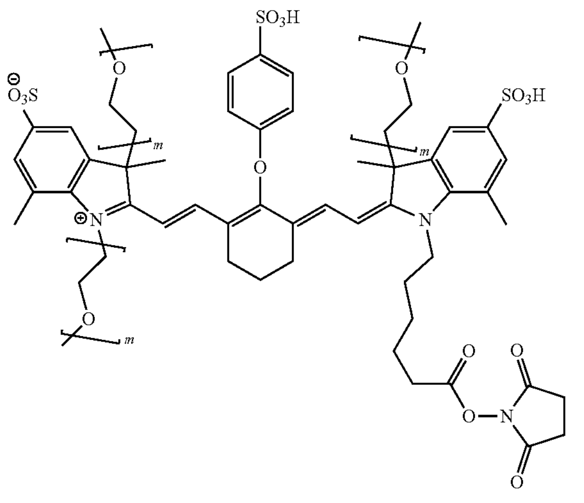
$m = 4$ -continued
Compound (8)
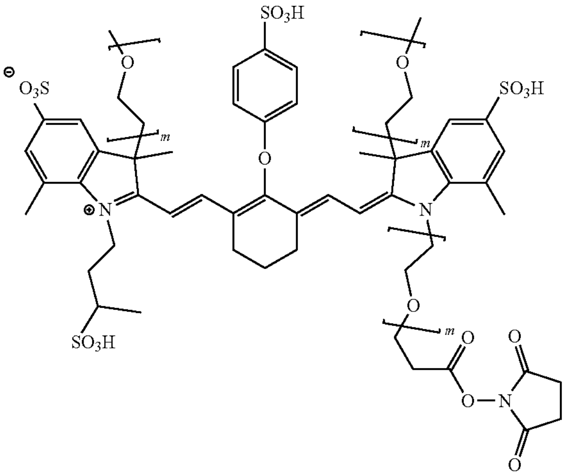
*m* = 4
Compound (9)
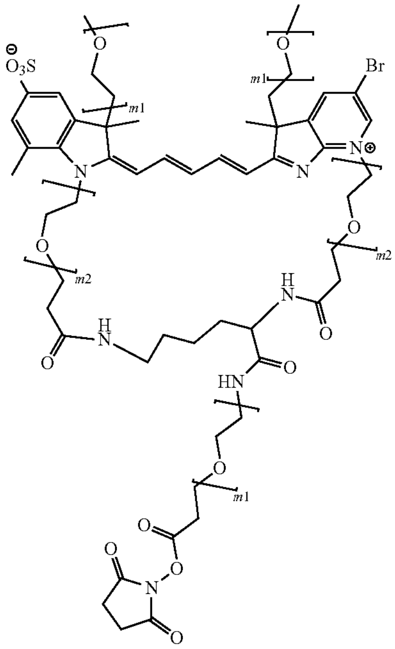
*m*1 = 4
*m*2 = 1
-continued
Compound (10)
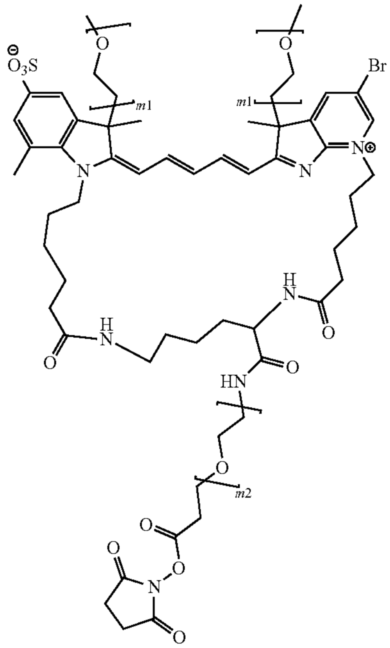
*m*1 = 4
*m*2 = 1
Compound (11)
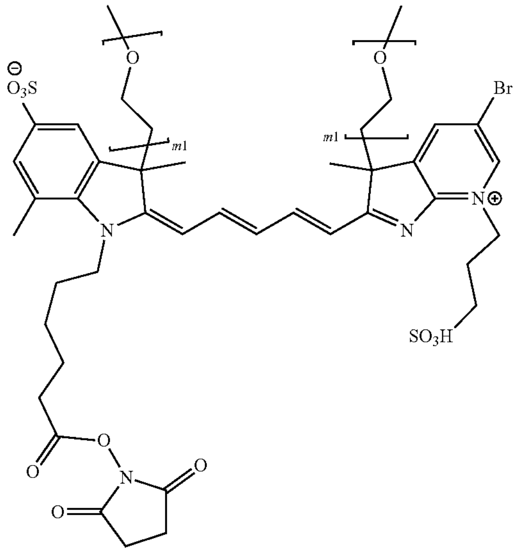
*m*1 = 10

-continued
Comparative compound (1)
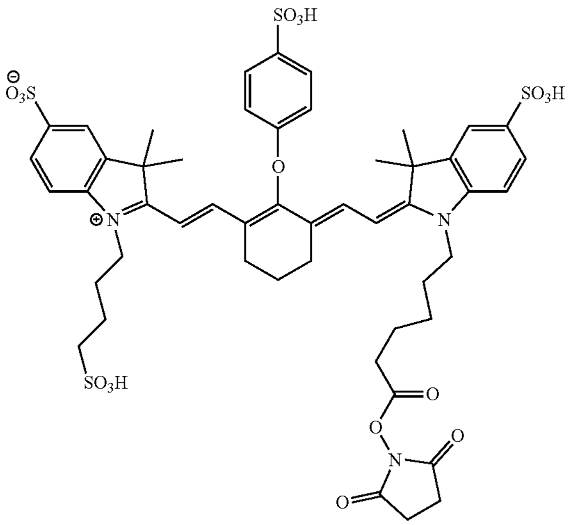
Comparative compound (2)
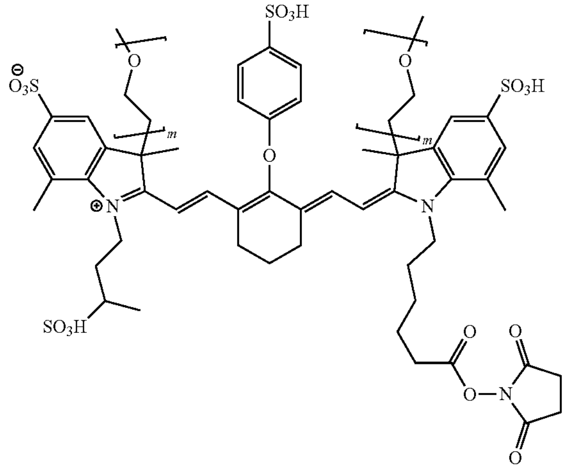
m = 11
Comparative compound (3)
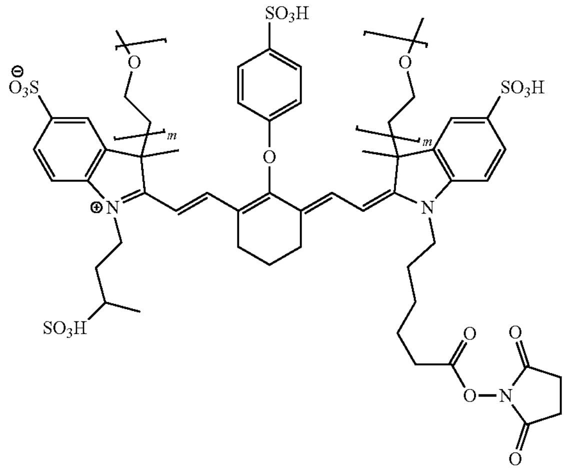
m = 4
-continued
Comparative compound (4)
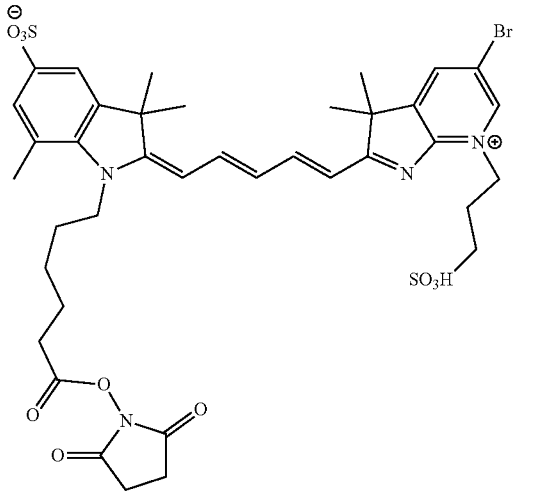
Comparative compound (5)
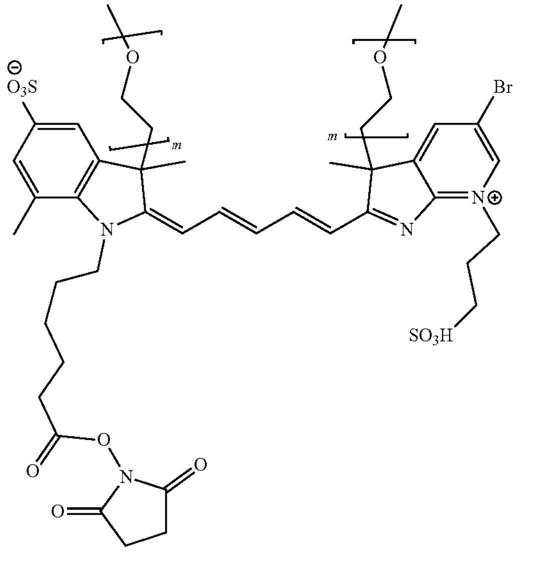
m = 11

-continued

Comparative compound (6)

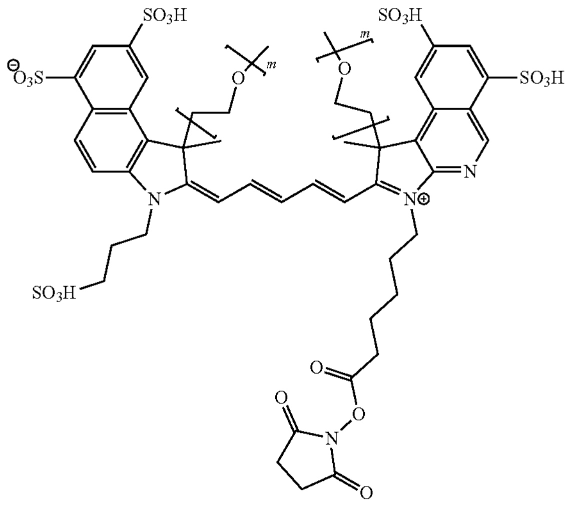

The comparative compound (1) is IRDye 800CW (product name) manufactured by LI-COR, Inc.

The methods for synthesizing the compounds (1) to (8) used in respective Examples are described in detail below; however, the starting materials, the dye intermediates and, the synthetic routes are not limited thereto.

In the following synthetic route, room temperature means 25° C.

Unless otherwise specified, SNAP Ultra C18 (product name, manufactured by Biotage, LLC) or Sfar C18 (product name, manufactured by Biotage, LLC) was used as the carrier in the reverse phase column chromatography, and Hi-Flash Column (product name, manufactured by Yamazen Corporation) was used as a carrier in the normal phase column chromatography.

The mixing ratio in the eluent used in the reverse phase column chromatography or the normal phase column chromatography is in terms of the volume ratio. For example, "acetonitrile:water=from 0:100 to 20:80" means that the eluent of "acetonitrile:water=0:100" was changed to an eluent of "acetonitrile:water=20:80".

For the preparative high performance liquid chromatography (HPLC), 2767 (product name, manufactured by Waters Corporation) was used.

The MS spectrum was measured by ACQUITY SQD LC/MS System [product name, manufactured by Waters Corporation, ionization method: electrospray Ionization (ESI)] or LCMS-2010EV [product name, manufactured by Shimadzu Corporation, ionization method: an ionization method simultaneously carrying out ESI and atmospheric pressure chemical ionization (APCI)].

Synthesis of Compound (1)

A compound (1) was synthesized based on the following scheme.

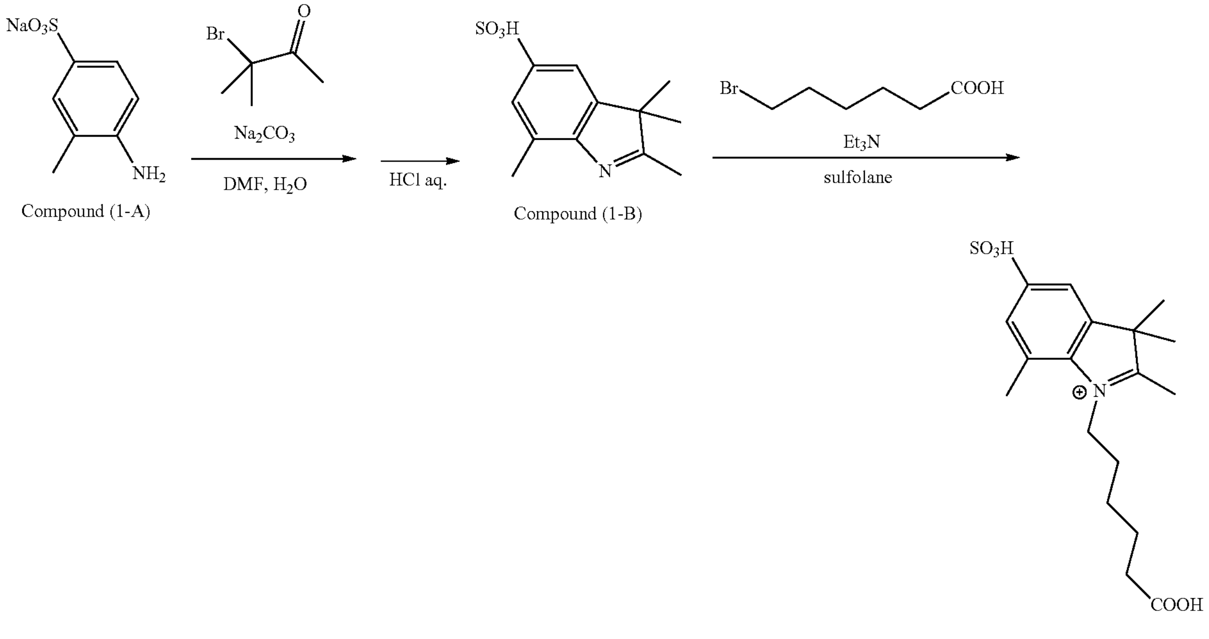

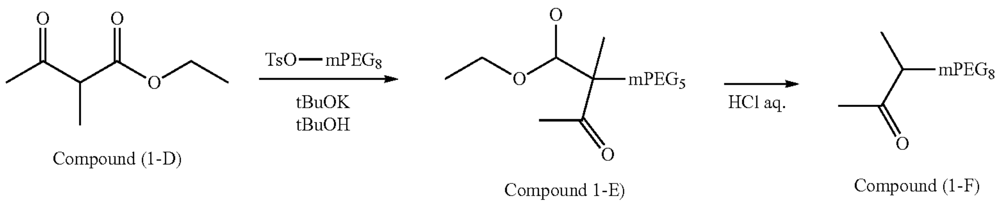

-continued
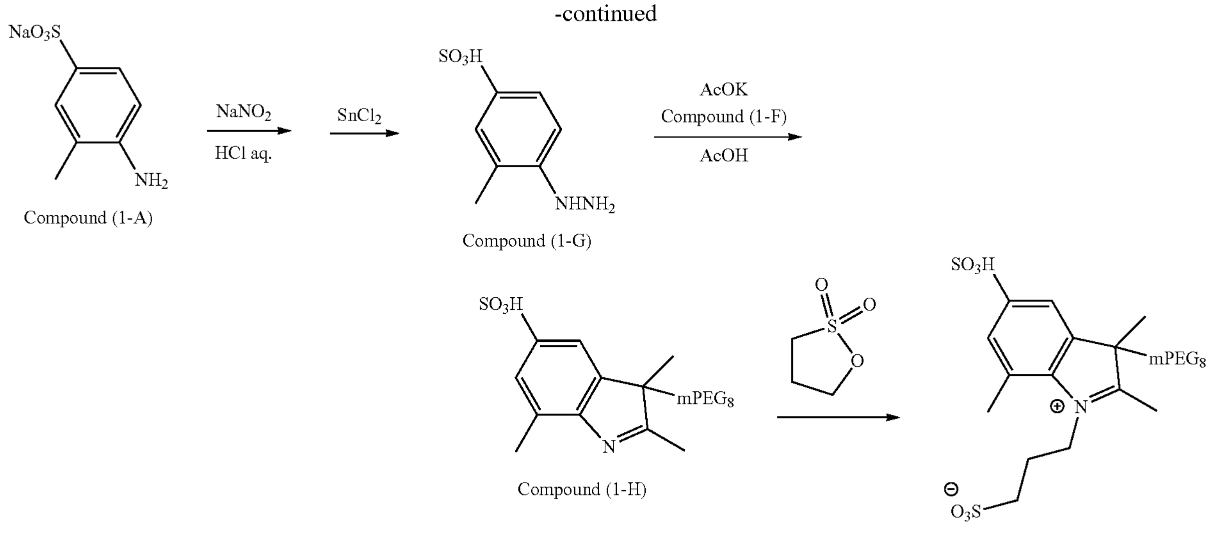
Compound (1-A)
Compound (1-G)
Compound (1-H)
Compound (1-I)
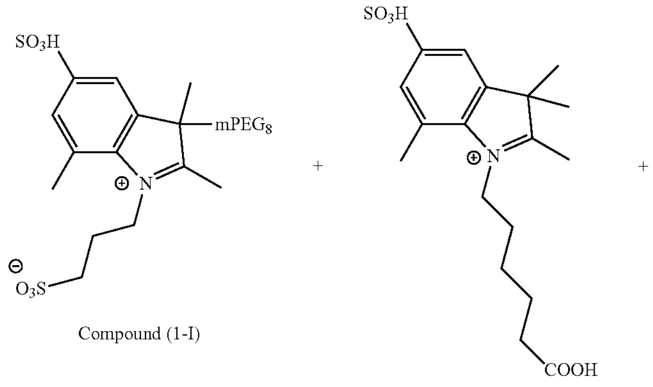
Compound (1-I)
Compound (1-C)
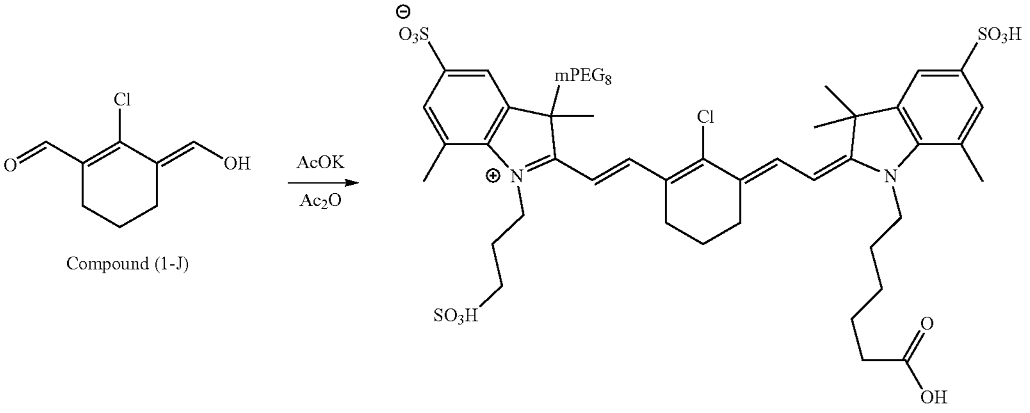
Compound (1-J)
Compound (1-K)

-continued
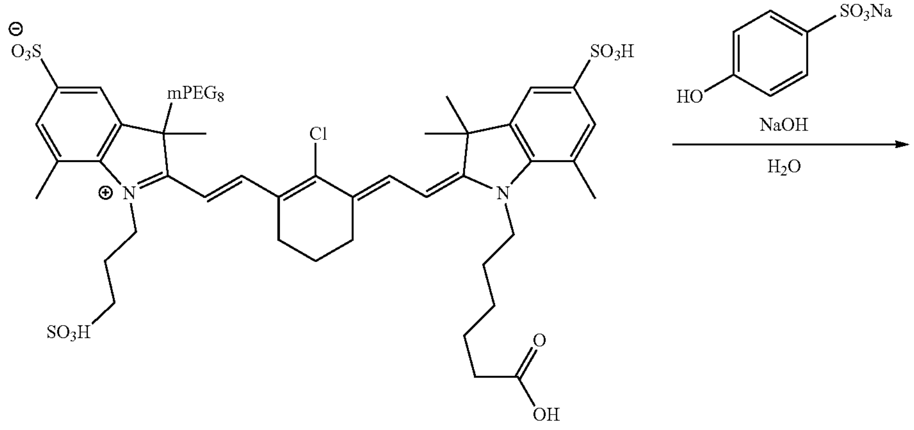
Compound (1-K)
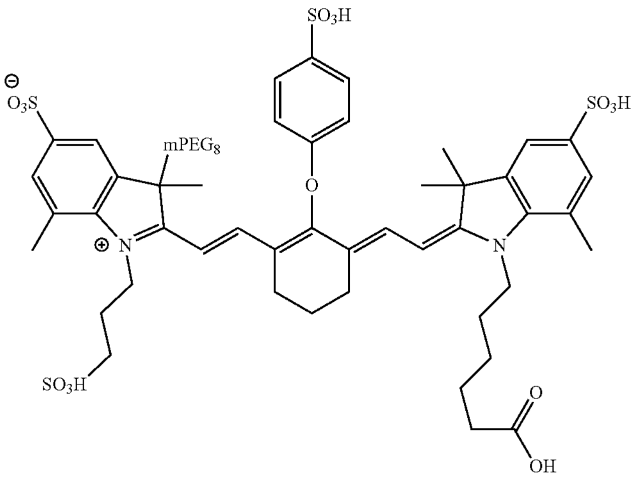
Compound (1-L)
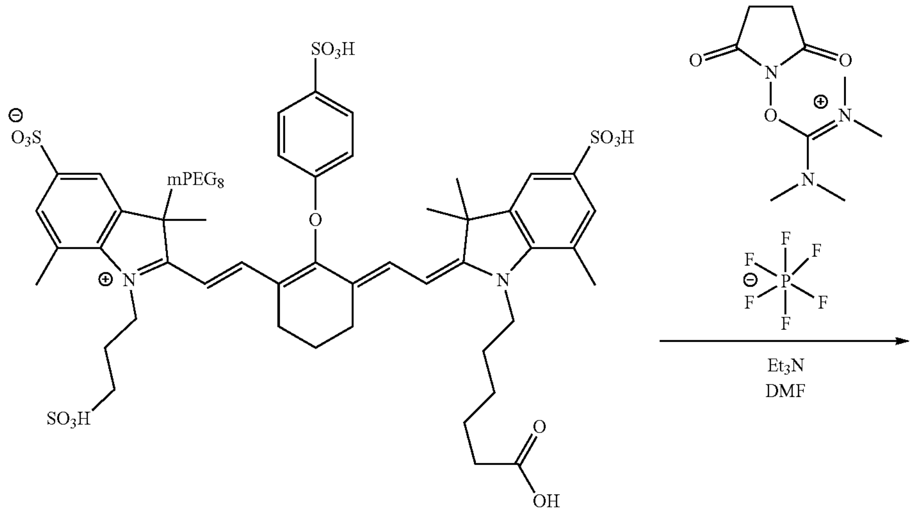
Compound (1-L)

-continued

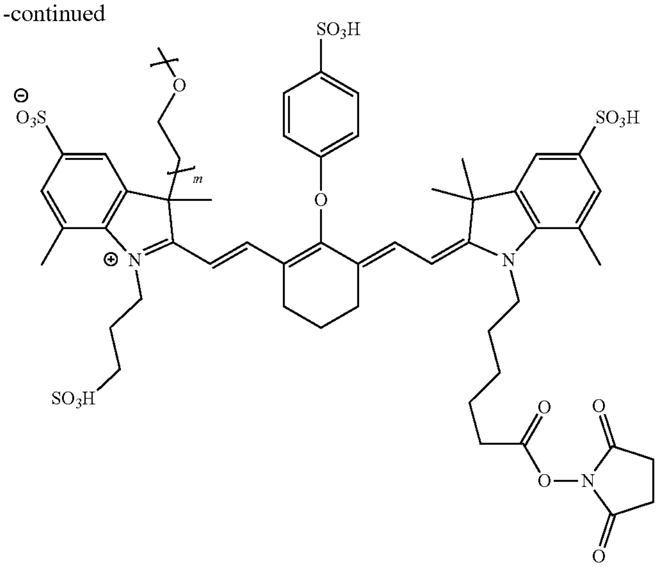

m = 8
Compound (1)

1) Synthesis of Compound (1-B)

10 g of a compound (1-A), 30 ml of N,N-dimethylformamide (DMF), 3.3 ml of distilled water, 3.1 g of sodium carbonate, and 16.5 g of 3-bromo-3-methyl-2-butanone were added in a three-necked flask having a capacity of 200 ml, and heating and stirring were carried out at 90° C. for 12 hours in a nitrogen atmosphere. Then, the solvent was distilled off from the reaction solution under reduced pressure, 15 ml of a 10% hydrochloric acid aqueous solution was added thereto, and then, heating was further carried out and stirred at 90° C. for 12 hours. Then, the solvent was distilled off under reduced pressure, dispersed in methanol, and subjected to filtration. The filtrate was concentrated under reduced pressure, acetone was added to cause precipitation, and the supernatant was removed by decantation. This crude product was purified by reverse phase column chromatography (acetonitrile/water=from 0/100 to 10/90) to obtain 4.1 g of a compound (1-B).

2) Synthesis of Compound (1-C)

400 mg of the compound (1-B), 2 ml of sulfolane, 365 mg of 6-bromohexanoic acid, and 0.169 ml of triethylamine ($Et_3N$) were added in an eggplant flask having a capacity of 50 ml and heated and stirred at 120° C. for 6 hours. Ethyl acetate was added to the reaction solution to cause precipitation. The precipitate was purified by reverse phase column chromatography (eluent: acetonitrile/water=from 0/100 to 20/100) to obtain 95 mg of a compound (1-C).

3) Synthesis of Compound (1-F)

200 ml of tert-butanol (tBuOH) and 12 g of potassium tert-butoxide (tBuOK) were added in a nitrogen-substituted three-necked flask having a capacity of 50 ml, and while stirring the resultant mixture, 14.4 g of the compound (1-D) was added dropwise thereto, and stirring was carried out for a while. Next, 53.9 g of polyethylene glycol methyl ether tosylate (average repetition number of ethylene glycol units=8.0, TsO-$mPEG_8$) was added dropwise thereto, and heating and stirring were carried out. After stirring at 80° C. for 1 hour, the solvent was distilled off under reduced pressure, a liquid separation operation was carried out with ethyl acetate and distilled water, and a crude product was extracted with distilled water. 30 ml of a 30% hydrochloric acid aqueous solution was added to the obtained crude product, and stirring was carried out at 100° C. for 3 hours. Then, the solvent was distilled off under reduced pressure, and purification was carried out by normal phase column chromatography (eluent: hexane/ethyl acetate=from 50/50 to 30/70) to obtain 12.1 g of a compound (1-F).

4) Synthesis of Compound (1-G)

20 g of the compound (1-A) and 150 ml of distilled water were added in a three-necked flask having a capacity of 1 L, and while stirring the resultant mixture, 75 ml of a 30% hydrochloric acid aqueous solution was added dropwise thereto. The mixture was cooled in a salt-ice bath, and a solution obtained by dissolving 7 g of sodium nitrite in 80 ml of distilled water was slowly added dropwise while maintaining the temperature at 3° C. or lower, and then the mixture was stirred at 0° C. to 3° C. for 45 minutes. Subsequently, a solution obtained by dissolving 38 g of tin (II) chloride in 90 ml of distilled water and 30 ml of a 30% HCl was slowly added dropwise, and then the mixture was stirred for 40 minutes at 7° C. or lower. The solvent was concentrated, and the residue was washed with isopropanol to obtain 15 g of a compound (1-G).

5) Synthesis of Compound (1-H)

2.0 g of the compound (1-G), 30 ml of acetic acid (AcOH), 4.4 g of the compound (1-F), and 0.98 g of potassium acetate (AcOK) were added in an eggplant flask having a capacity of 200 ml and stirred at 140° C. for 1 hour in a nitrogen atmosphere. The solvent was distilled off under reduced pressure, the purification was carried out by reverse phase column chromatography (eluent: acetonitrile/water=from 0/100 to 35/65) to obtain 3.5 g of a compound (1-H).

6) Synthesis of Compound (1-I)

200 mg of the compound (1-H), 2 ml of sulfolane, 80 mg of 1,3-propane sultone, and 129 mg of N-ethyldiisopropylamine were added in an eggplant flask having a capacity of 50 ml and stirred at 120° C. for 1.5 hours. After returning it to room temperature, 200 mg of distilled water was added, and purification was carried out by reverse phase column chromatography (eluent: acetonitrile/water=from 0/100 to 10/90) to obtain 61 mg of a compound (1-I).

7) Synthesis of Compound (1-K)

72.8 mg of the compound (1-I), 36.8 mg of the compound (1-C), 17.3 mg of the compound (1-J), 9.8 mg of potassium acetate (AcOK), and 1 ml of anhydrous acetic acid ($Ac_2O$) were added to a test tube, and stirring was carried out at 60° C. for 2 hours in a nitrogen atmosphere. After the reaction was settled, distilled water was added, and purification was carried out by reverse phase column chromatography (eluent: acetonitrile/water=from 0/100 to 25/75) to obtain 33 mg of a compound (1-K).

8) Synthesis of Compound (1-L)

10 mg of the compound (1-K) and 500 L of distilled water were added to a test tube, and stirring was carried out at 95° C. A solution obtained by mixing 16.5 mg of sodium 4-hydroxybenzenesulfonate and 5 mg of sodium hydroxide in 500 L of distilled water was added dropwise to this solution, and stirring was carried out at 95° C. for 30 minutes. The reaction solution was cooled to room temperature and purified by preparative HPLC, and freeze drying was followed to obtain 5.1 mg of a compound (1-L). The results of the MS measurement of the compound (1-L) were as follows.

MS (ESI m/z):(M+H+)+=1,369, $(M-H^+)^-$=1,367

9) Synthesis of Compound (1)

0.28 ml of N,N-dimethylformamide (DMF), an N,N-dimethylformamide solution obtained by dissolving 1 mg of N,N,N',N'-tetramethyl-O—(N-succinimidyl)uronium hexafluorophosphate, and 1.3 μL of triethylamine ($Et_3N$) were added to 2.6 mg of the compound (1-L), and stirring was carried out for 1 hour. Then, the solvent was distilled off under reduced pressure, ethyl acetate was added, the supernatant was removed, and vacuum drying was carried out to obtain a compound (1).

Synthesis of Compound (2)

A compound (2) was synthesized in the same manner as the compound (1), based on the following scheme. The results of the MS measurement of the compound (2-L) were as follows.

MS (ESI m/z):$(M+H^+)^+$=1,369, $(M-H^+)^-$=1,367

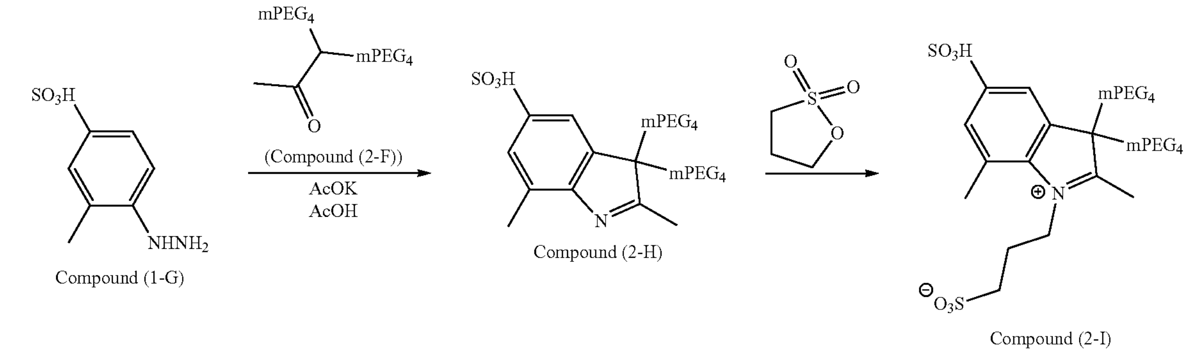

Compound (1-G)
Compound (2-H)
Compound (2-I)

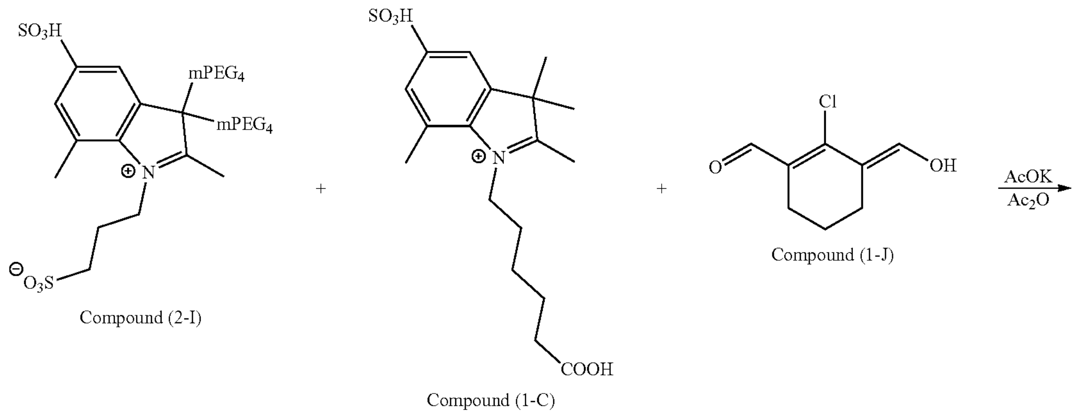

Compound (2-I)
Compound (1-C)
Compound (1-J)

-continued
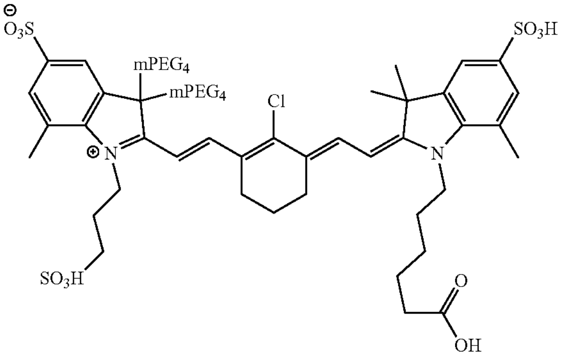
Compound (2-K)
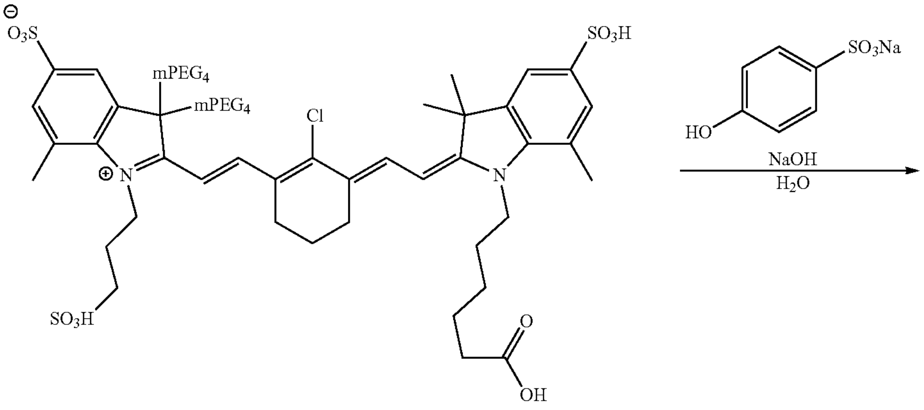
Compound (2-K)
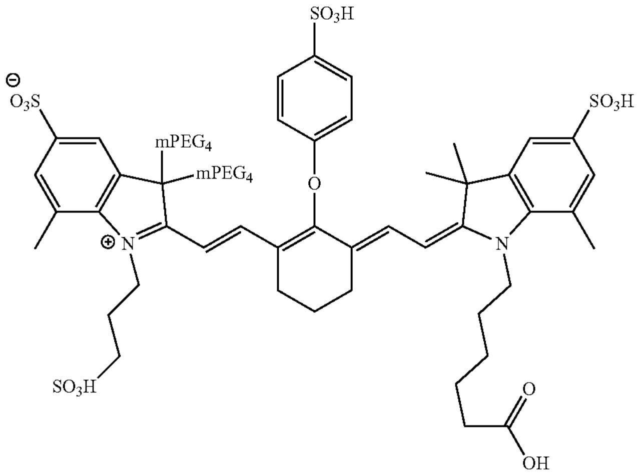
Compound (2-L)

-continued
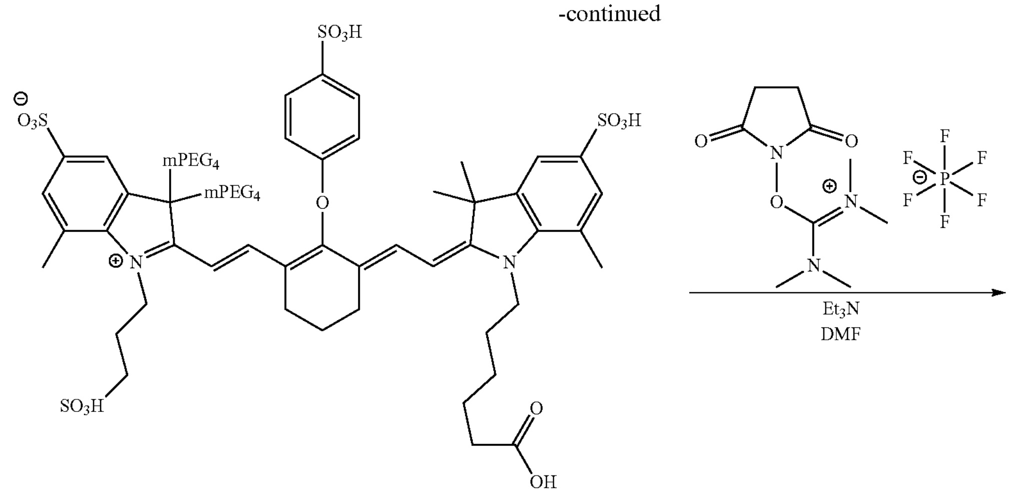
Compound (2-L)
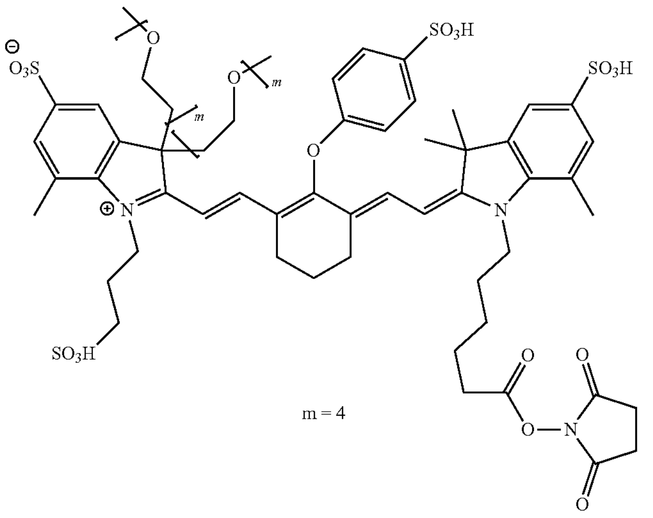
Compound (2)
Synthesis of Compound (3)
A compound (3) was synthesized in the same manner as the compound (1), based on the following scheme. The results of the MS measurement of the compound (3-L) were as follows.
MS (ESI m/z):$(M+H^+)^+$=1,383, $(M-H^+)^-$=1,381
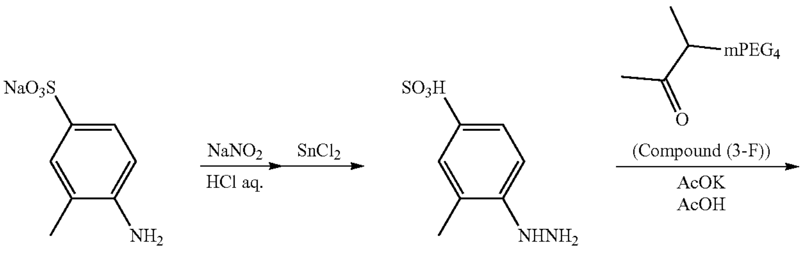
Compound (1-A) Compound (1-G)

-continued
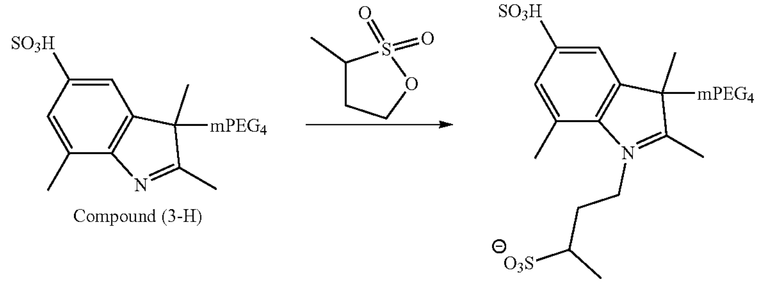
Compound (3-H)
Compound (3-J)
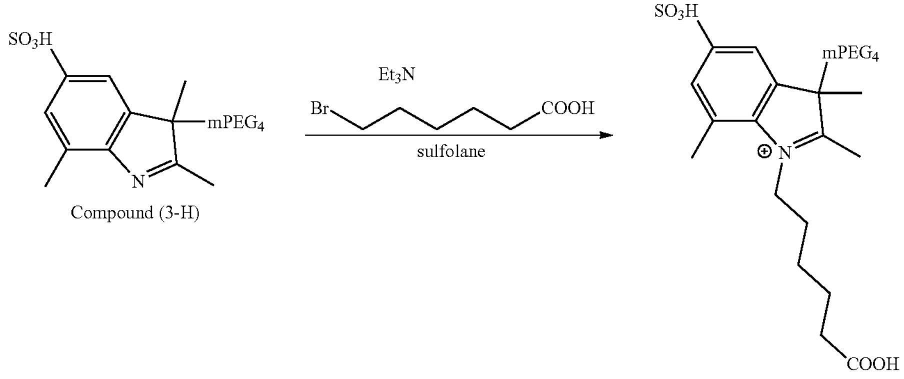
Compound (3-H)
Compound (3-C)
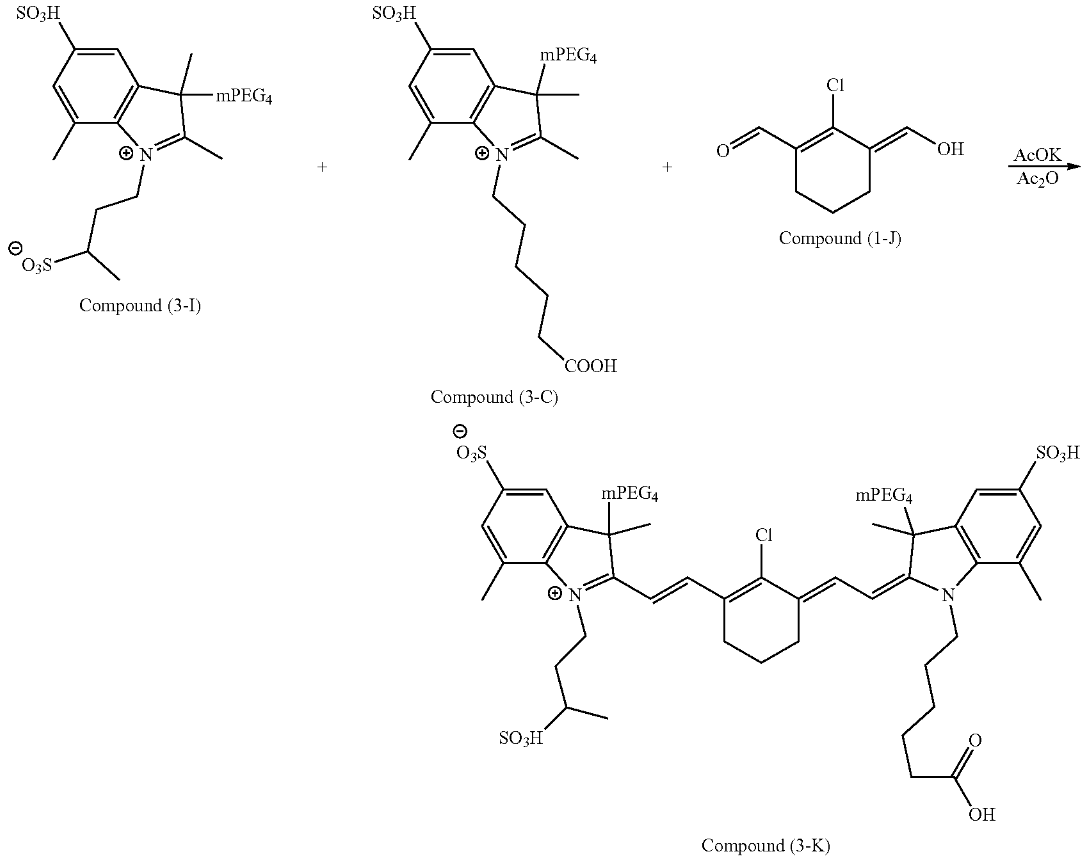
Compound (3-I)
Compound (3-C)
Compound (1-J)
Compound (3-K)

-continued
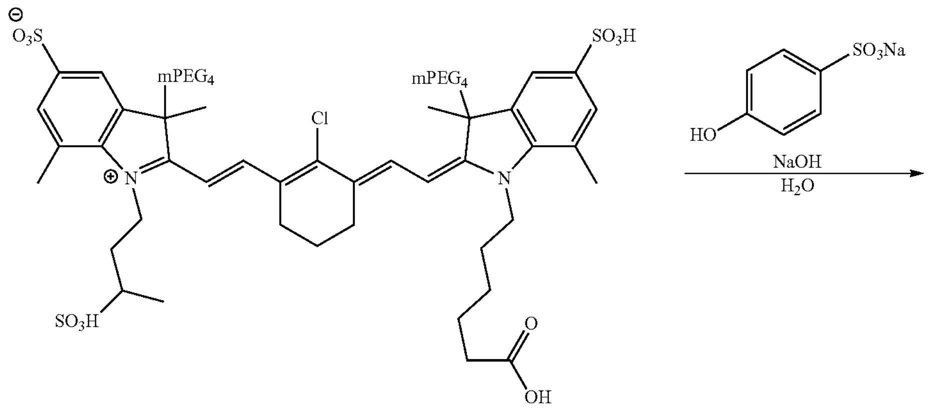
Compound (3-K)
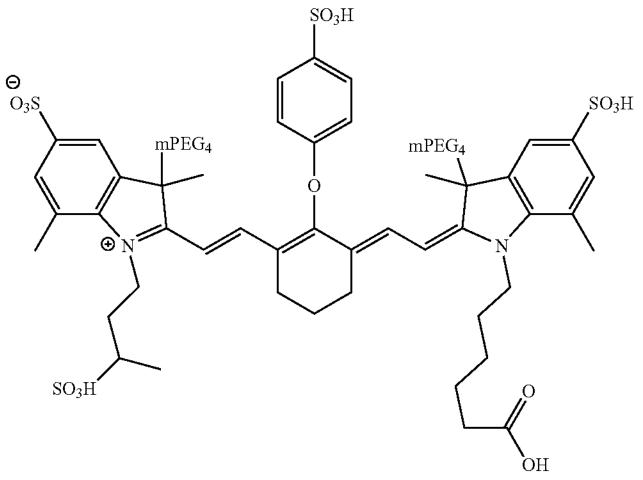
Compound (3-L)
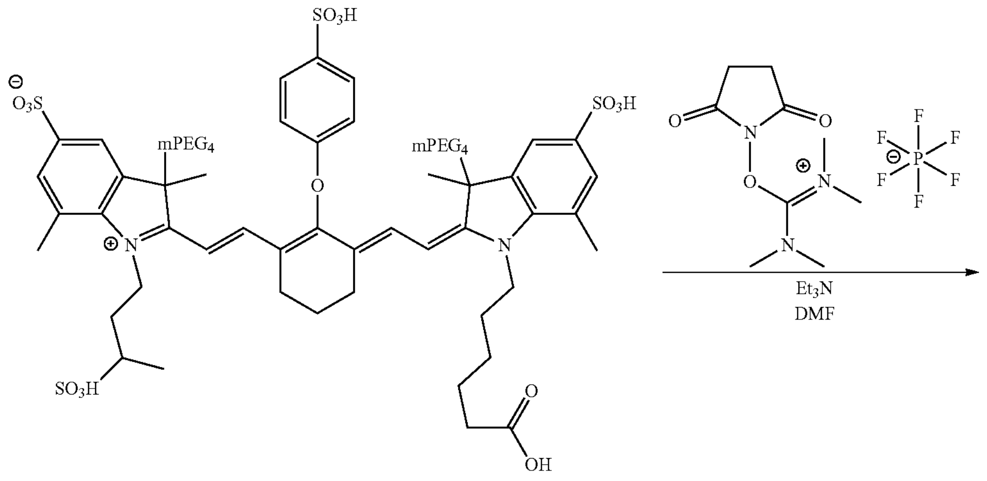
Compound (3-L)

-continued
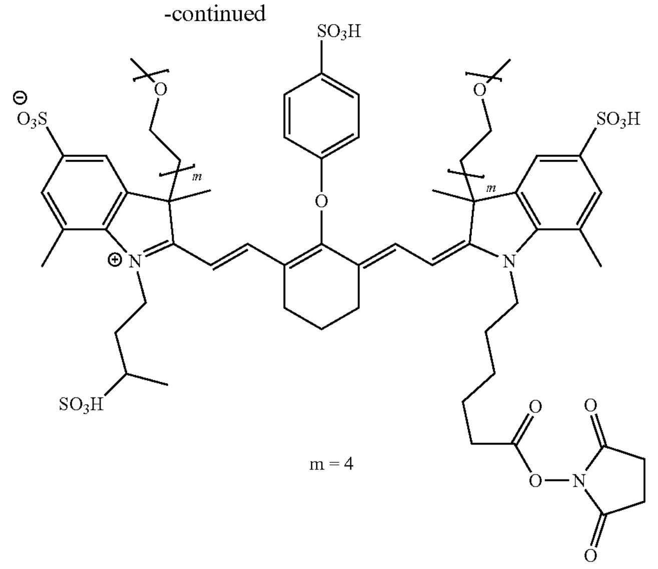
Compound (3)
Synthesis of Compound (4)
A compound (4) was synthesized in the same manner as the compound (1), based on the following scheme. The results of the MS measurement of the compound (4-L) were as follows.
MS (ESI m/z):$(M+H^+)^+$1,912, $(M-H+)^-$=1,910
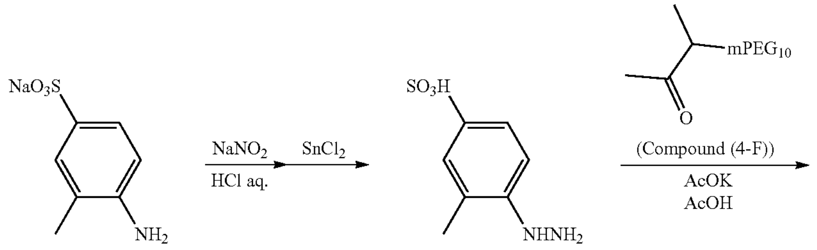
Compound (1-A)
Compound (1-G)
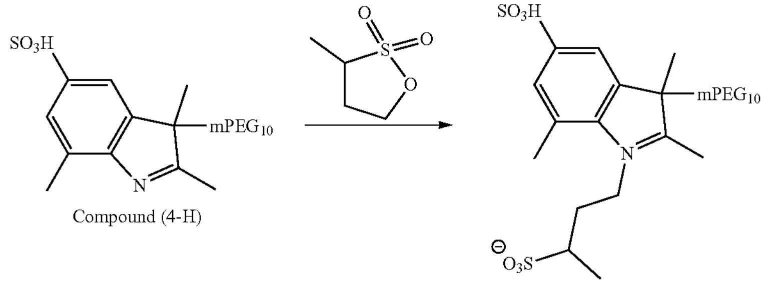
Compound (4-H)
Compound (4-I)

-continued
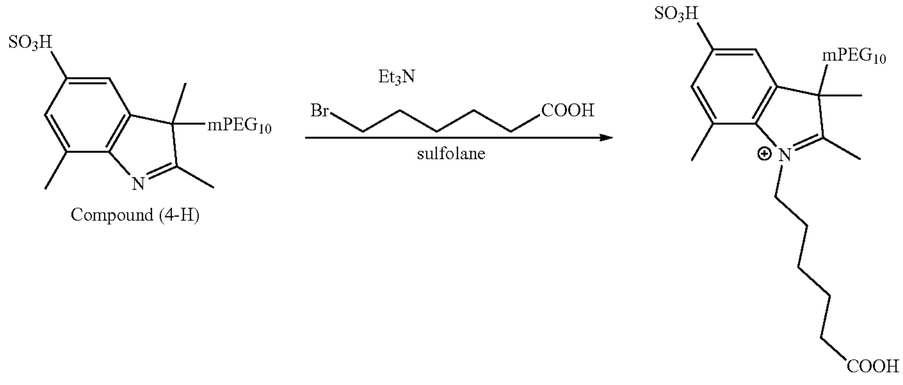
Compound (4-H)
Compound (4-C)
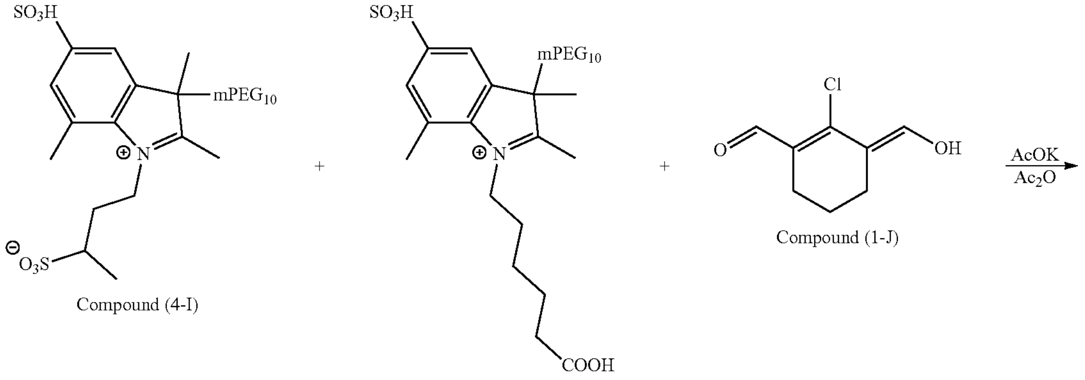
Compound (4-I)
Compound (1-J)
Compound (4-C)
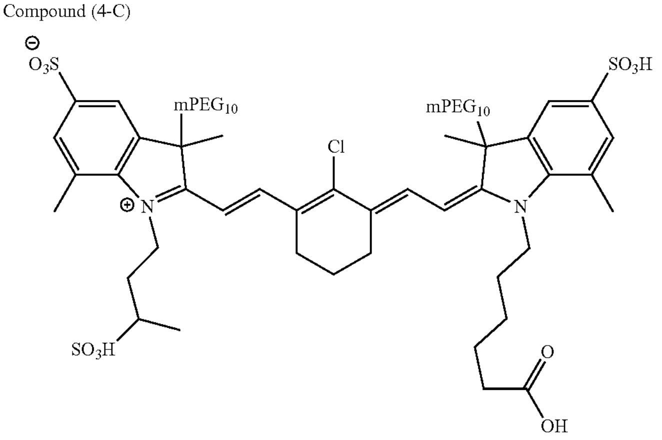
Compound (4-K)
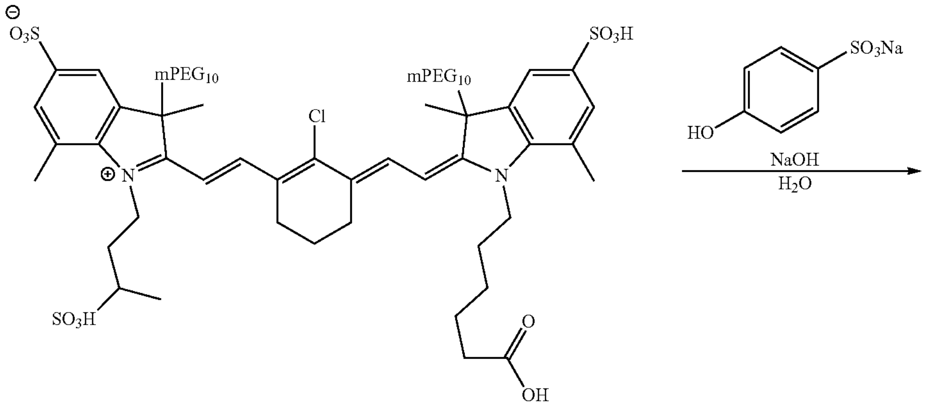
Compound (4-K)

-continued
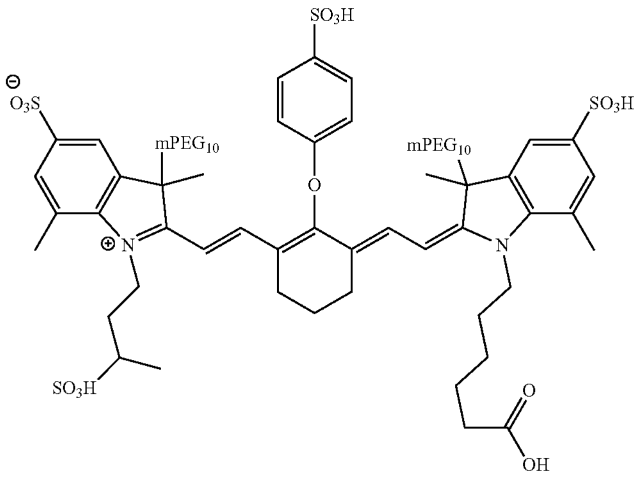
Compound (4-L)
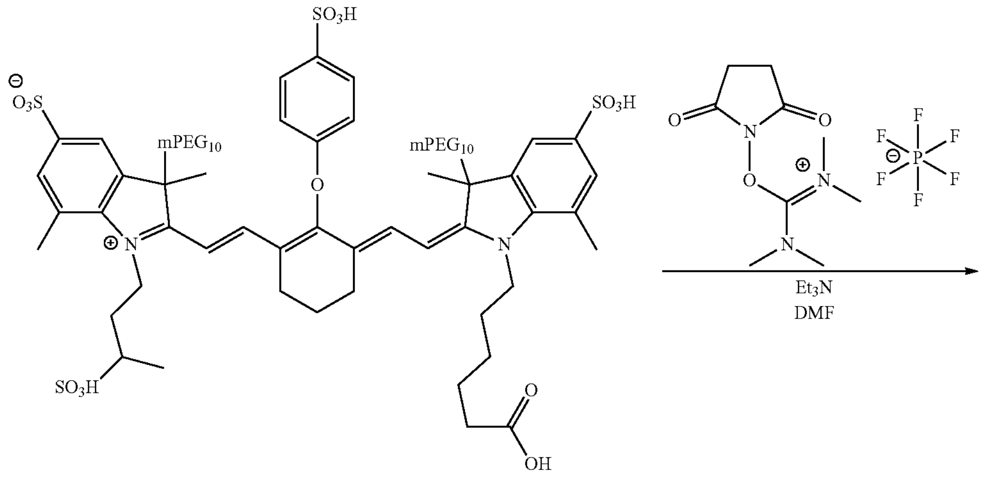
Compound (4-L)
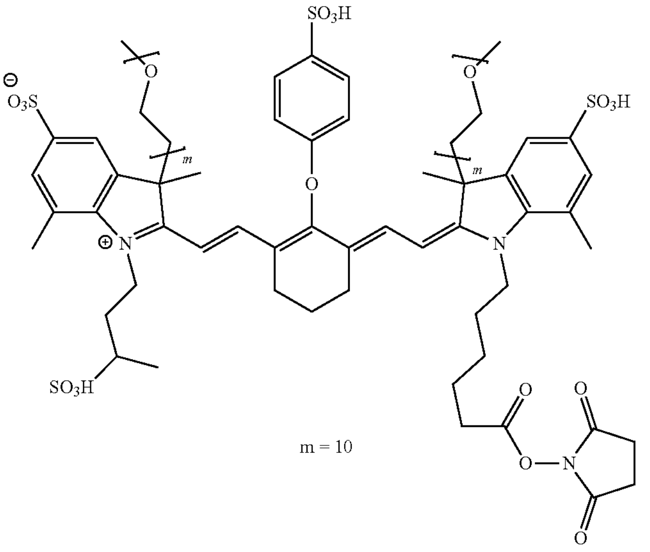
m = 10
Compound (4)

Synthesis of Compound (5)
A compound (5) was synthesized in the same manner as the compound (1), based on the following scheme. The results of the MS measurement of the compound (5-L) were as follows.
MS (ESI m/z):$(M+H^+)^+$=1,572, $(M-H^+)^-$=1,570
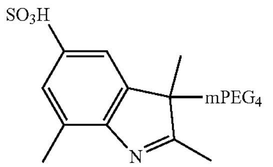
Compound (3-H)
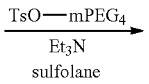
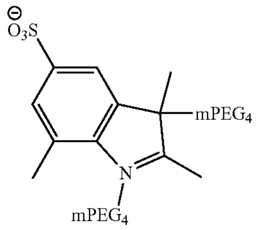
Compound (5-I)
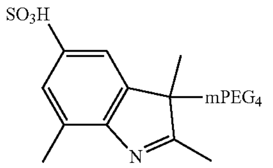
Compound (3-H)
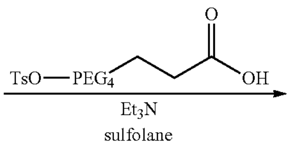
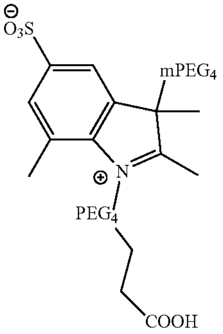
Compound (5-C)
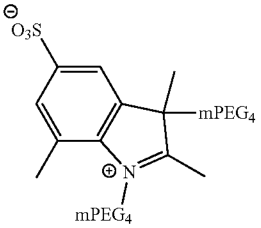
Compound (5-I)
+
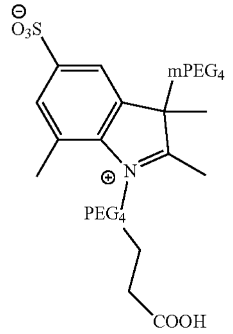
Compound (5-C)
+
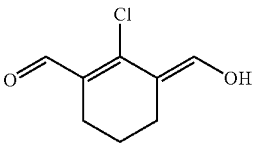
Compound (1-J)
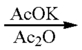
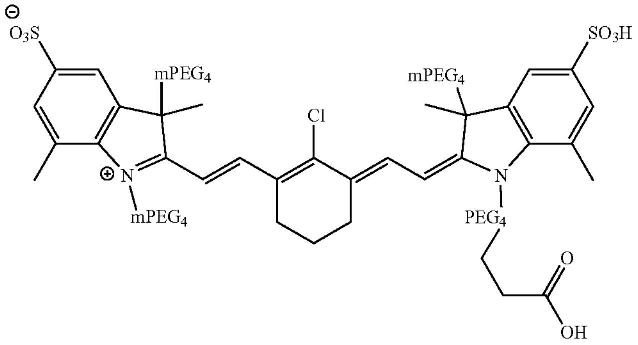
Compound (5-K)

-continued
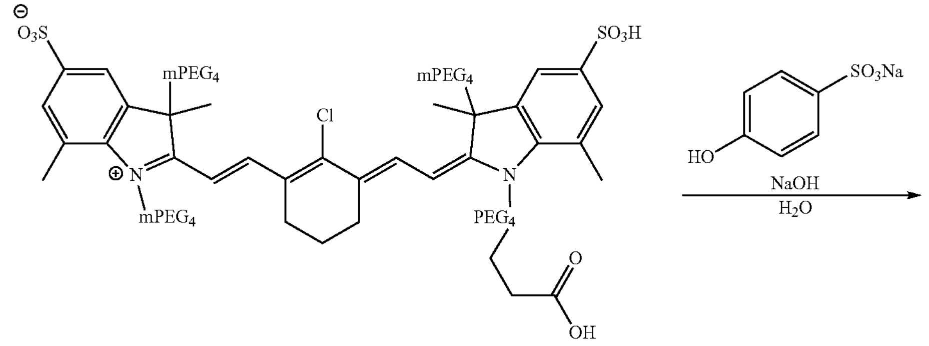
Compound (5-K)
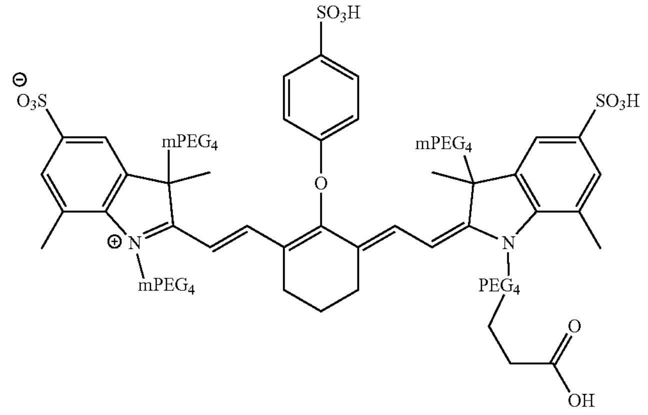
Compound (5-L)
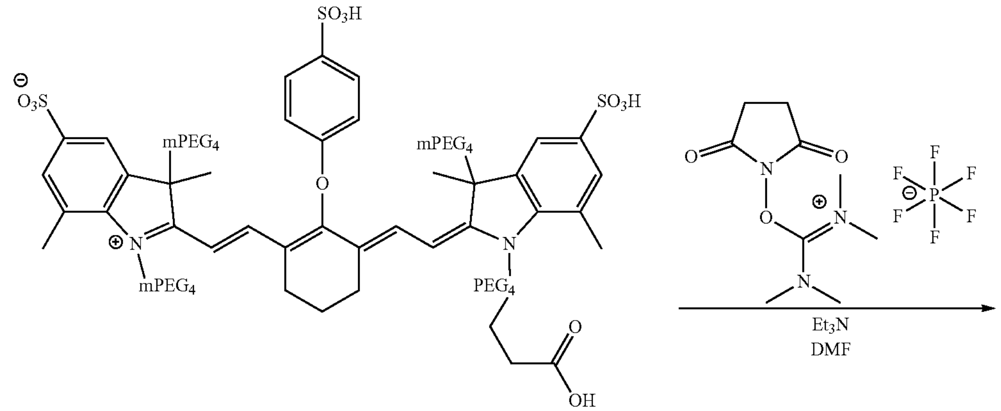
Compound (5-L)

-continued

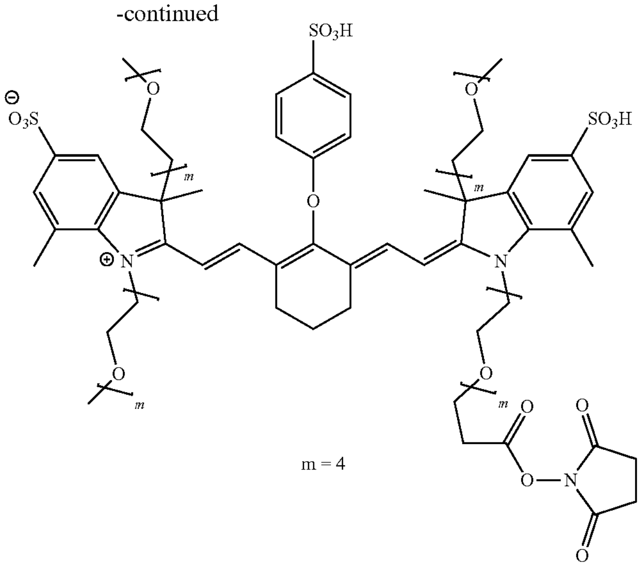

m = 4

Compound (5)

Synthesis of Compound (6)

A compound (6) was synthesized in the same manner as the compound (1), based on the following scheme. The results of the MS measurement of the compound (6-K) were as follows.

MS (ESI m/z):$(M+H^+)^+$=1,502, $(M-H^+)^-$=1,500

A compound (6-J) was synthesized as follows.

Synthesis of Compound (6-J)

0.35 g of the compound (6-I), 1.3 g of the zinc powder, and 10 ml of ethanol were added to an eggplant flask having a capacity of 50 ml, and the resultant mixture was reacted under reflux for 3 hours. Zinc was removed by filtration through celite, the purification was carried out by reverse phase column chromatography (eluent: acetonitrile/water=from 0/100 to 35/65) to obtain 0.1 g of a compound (6-J).

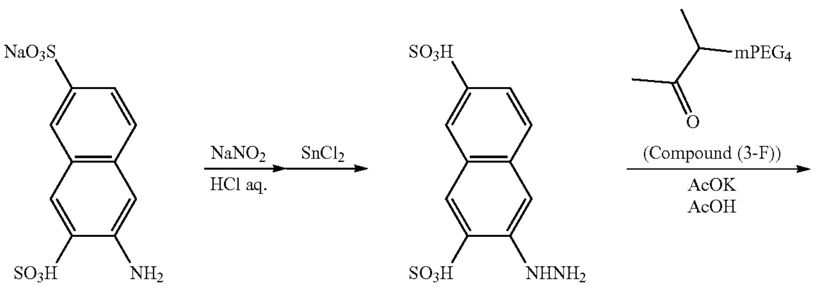

Compound (6-A) Compound (6-B)

-continued
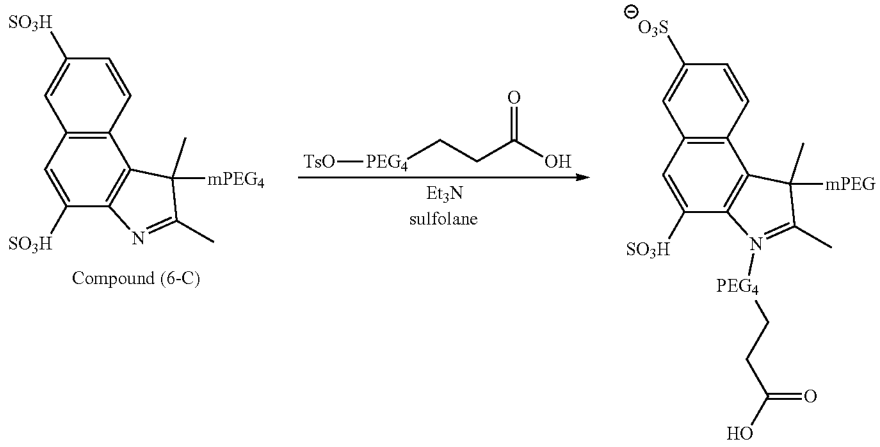
Compound (6-C)
Compound (6-D)
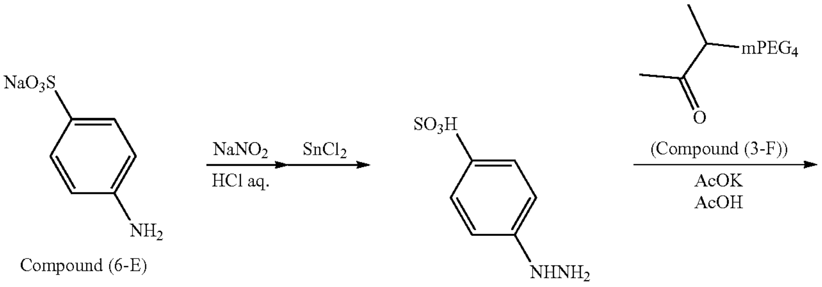
Compound (6-E)
Compound (6-F)
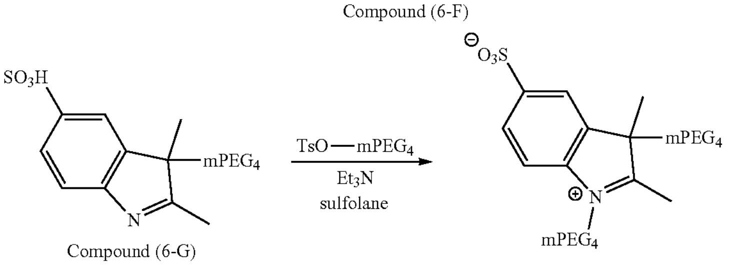
Compound (6-G)
Compound (6-H)
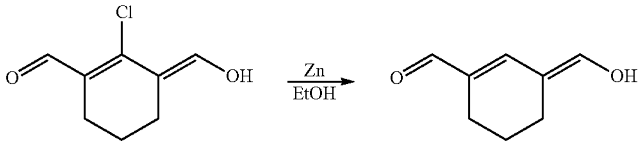
Compound (6-I)
Compound (6-J)
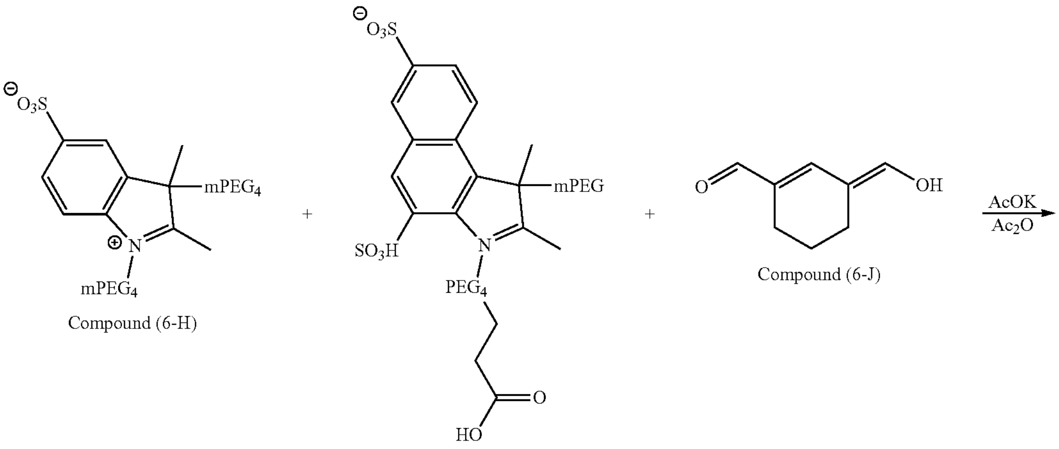
Compound (6-H)
Compound (6-D)
Compound (6-J)

-continued
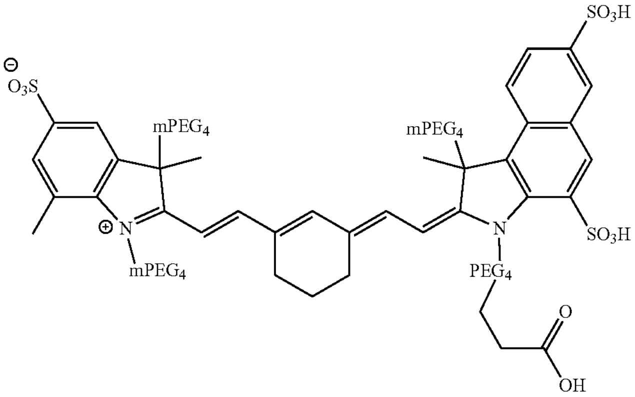
Compound (6-K)
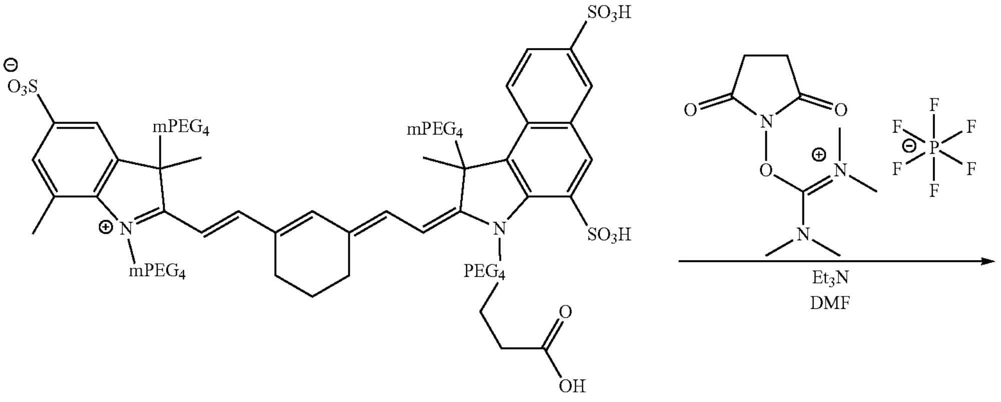
Compound (6-K)
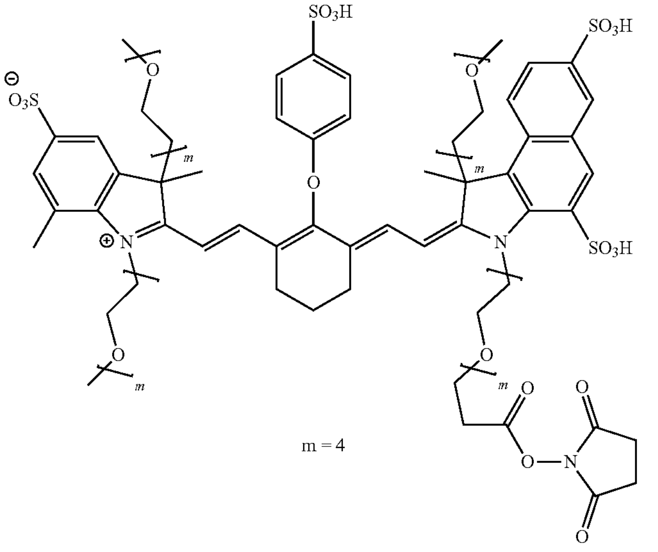
Compound (6)

Synthesis of Compound (7)
A compound (7) was synthesized in the same manner as the compound (1), based on the following scheme. The results of the MS measurement of the compound (7-L) were as follows.
MS (ESI m/z):$(M+H^+)^+$=1,438, $(M-H^+)^-$=1,436
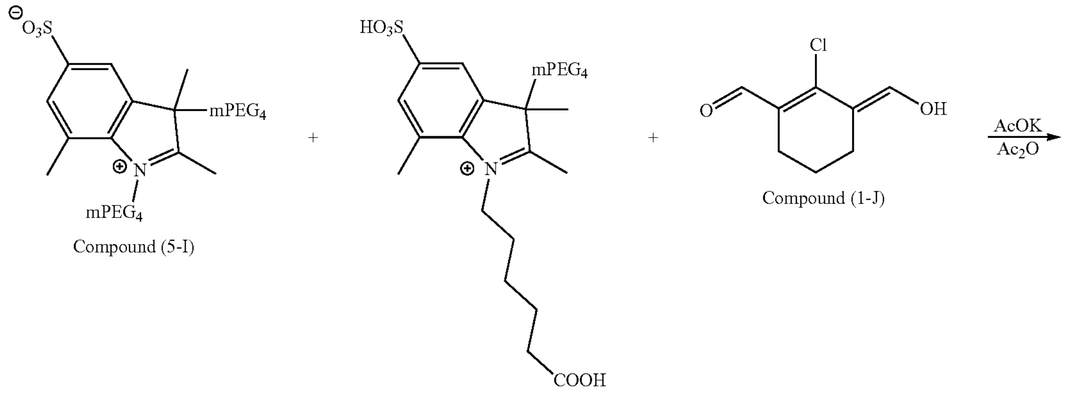
Compound (5-I)
Compound (3-C)
Compound (1-J)
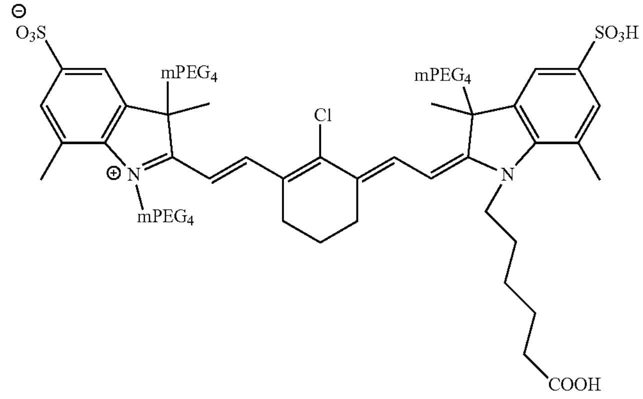
Compound (7-K)
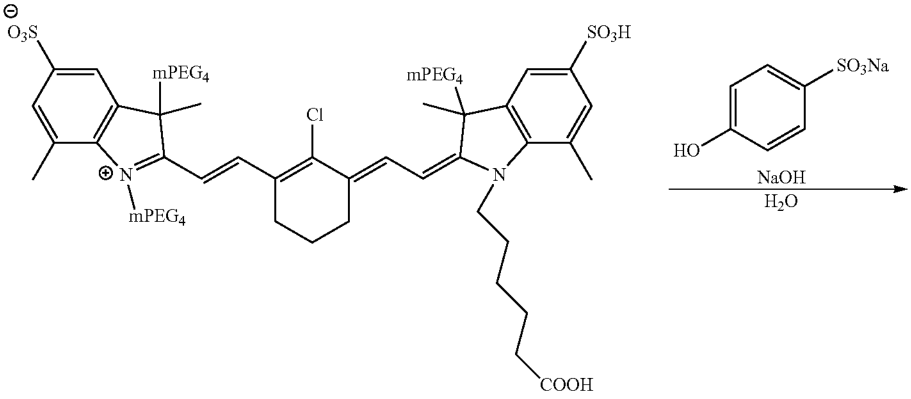
Compound (7-K)

-continued
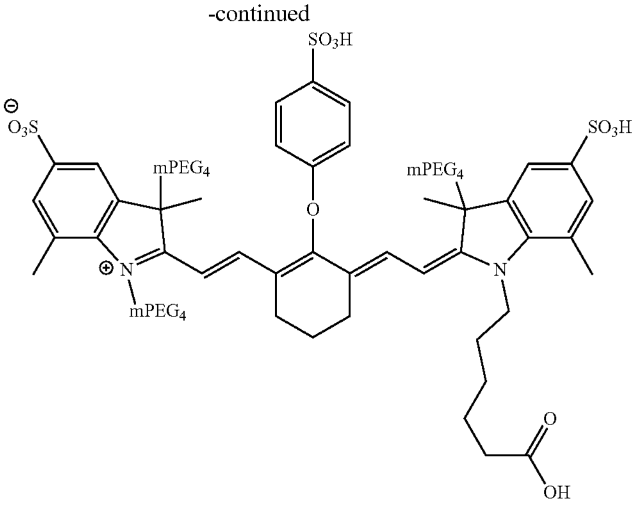
Compound (7-L)
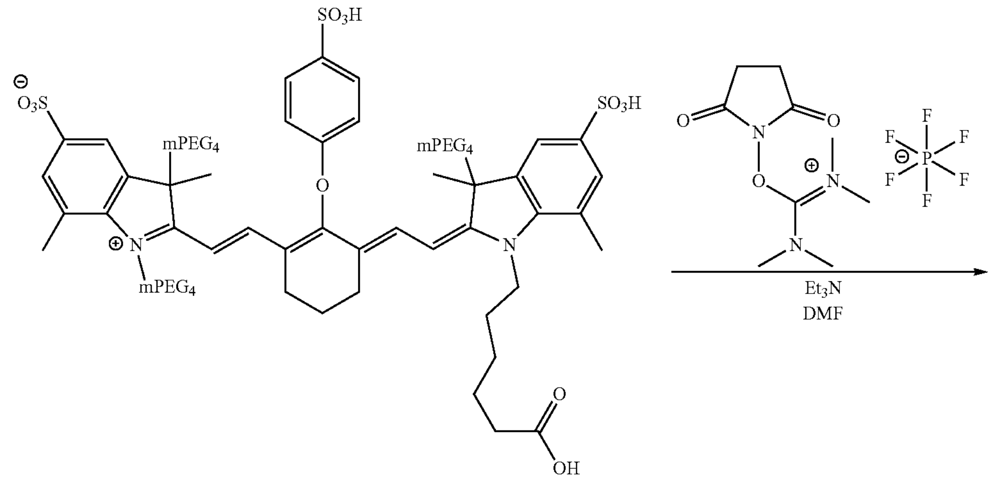
Compound (7-L)
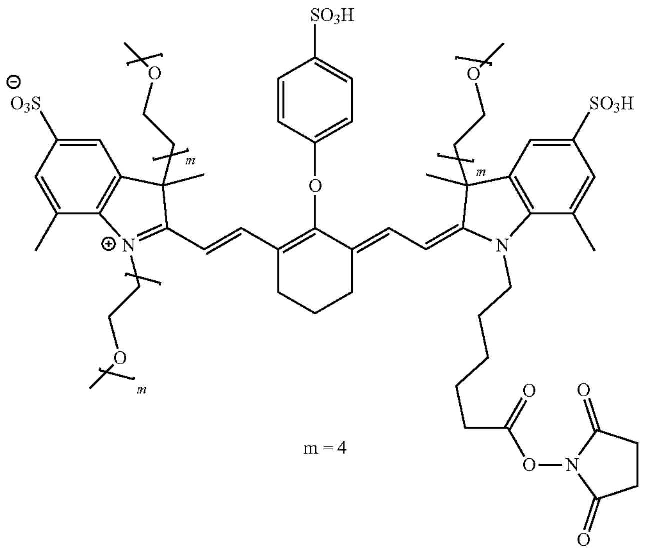
m = 4
Compound (7)

Synthesis of Compound (8)
A compound (8) was synthesized in the same manner as the compound (1), based on the following scheme. The results of the MS measurement of the compound (8-L) were as follows.
MS (ESI m/z):$(M+H^+)^+$=1,518, $(M-H^+)^-$=1,516
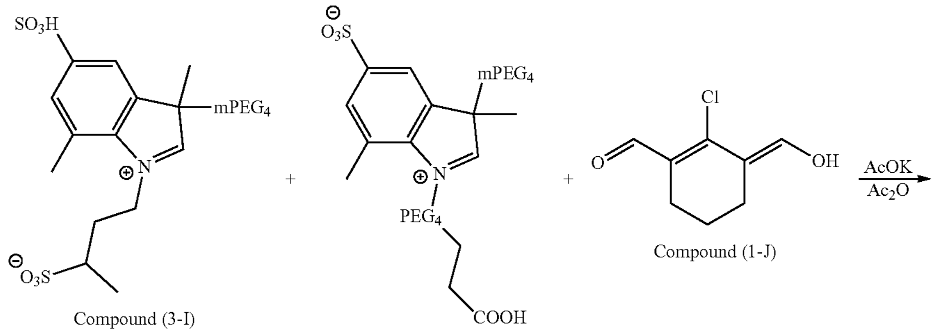
Compound (3-I)
Compound (5-C)
Compound (1-J)
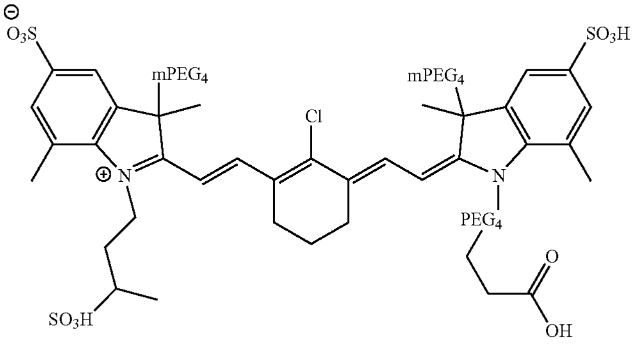
Compound (8-K)
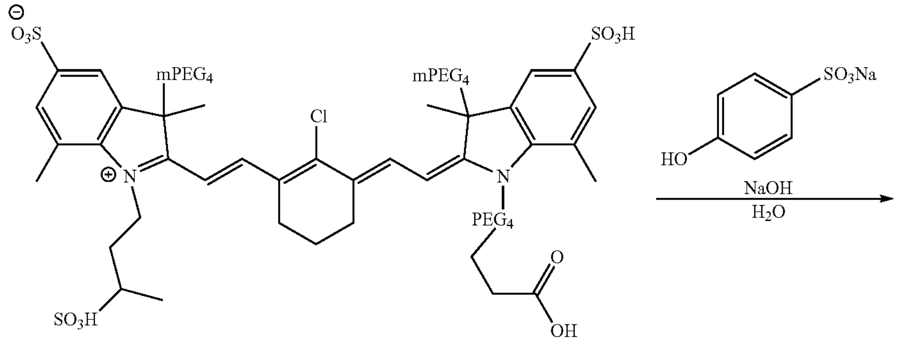
Compound (8-K)

-continued
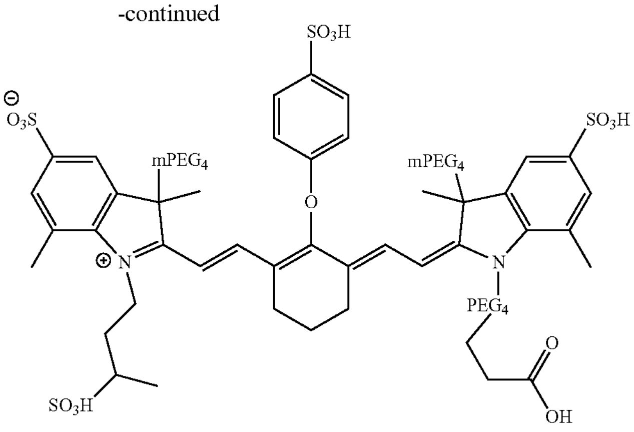
Compound (8-L)
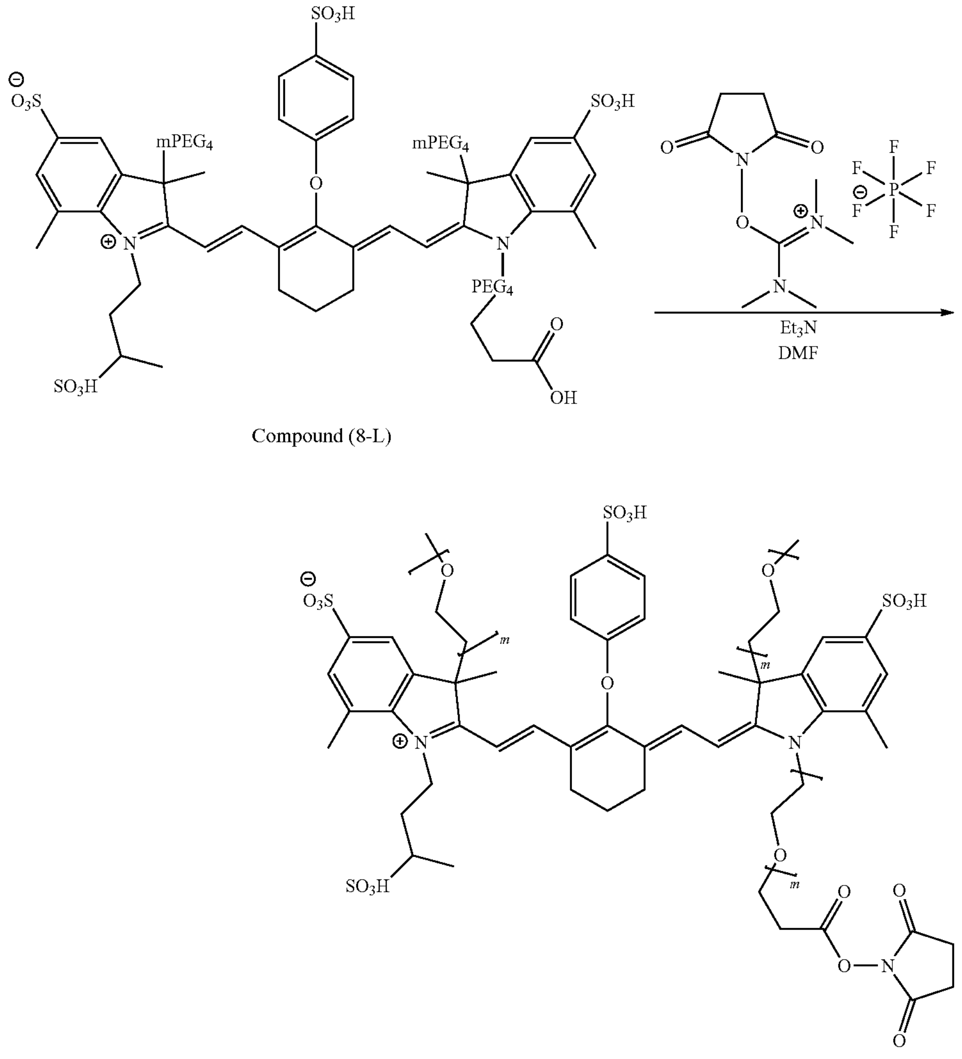
Compound (8-L)
m = 4
Compound (8)

Synthesis of Compound (9)

A compound (9) was synthesized in the same manner as the compound (1), based on the following scheme. The results of the MS measurement of the compound (9-H) were as follows.

MS (ESI m/z):$(M+H^+)^+$=1,470, $(M-H^+)^-$=1,468

A compound (9-H) was synthesized as follows.

Synthesis of Compound (9-G)

20 mg of the compound (9-F), 2 ml of DMF, 80 mg of N,N,N',N'-tetramethyl-O—(N-succinimidyl)uronium hexafluorophosphate (HSTU), and 77 μL of triethylamine (TEA) were added in an eggplant flask having a capacity of 10 ml, and the resultant mixture was reacted for 3 hours. Then, the reaction solution was added dropwise to a solution obtained by dissolving 6 mg of lysine hydrochloride and 3 mg of sodium carbonate in 40 ml of water, and then, the resultant reaction solution reacted for 3 hours. The reaction solution was concentrated and subsequently purified by preparative HPLC, and freeze drying was followed to obtain 7.0 mg of a compound (9-G).

Synthesis of Compound (9-H)

7.0 mg of the compound (9-G), 2 ml of DMF, 2 mg of N,N,N',N'-tetramethyl-O—(N-succinimidyl)uronium hexafluorophosphate (HSTU), and 5 μL of triethylamine (TEA) were added in an eggplant flask having a capacity of 10 ml, and the resultant mixture was reacted for 3 hours. Then, 0.5 ml of a DMF solution of 1 mg of aminoPEG4acid (product name, manufactured by BROAD PHARM, average repetition number of ethylene glycol units=4.0) was added to the reaction solution, and the reaction was carried out for 3 hours. The reaction solution was concentrated, purified by preparative HPLC, and freeze drying was followed to obtain 5.3 mg of a compound (9-H).

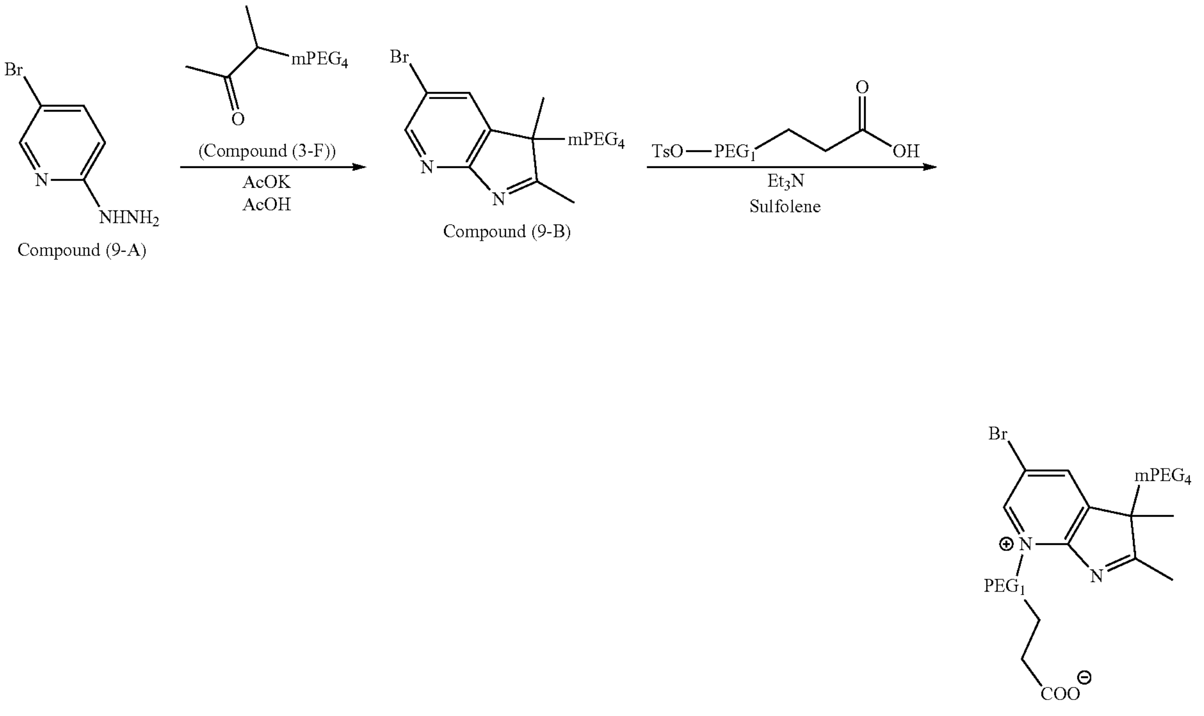

Compound (9-A)

Compound (9-B)

Compound (9-C)

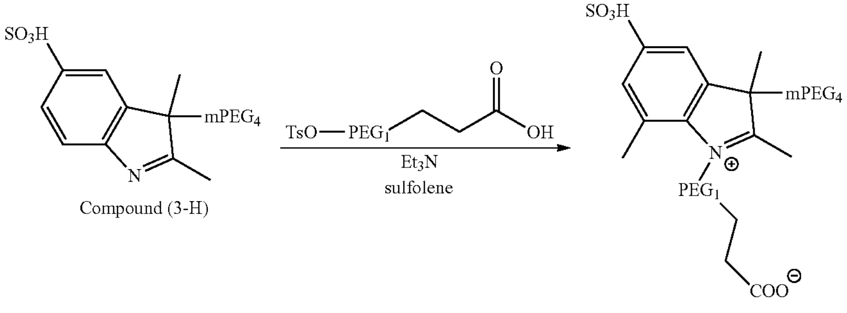

Compound (3-H)

Compound (9-D)

-continued
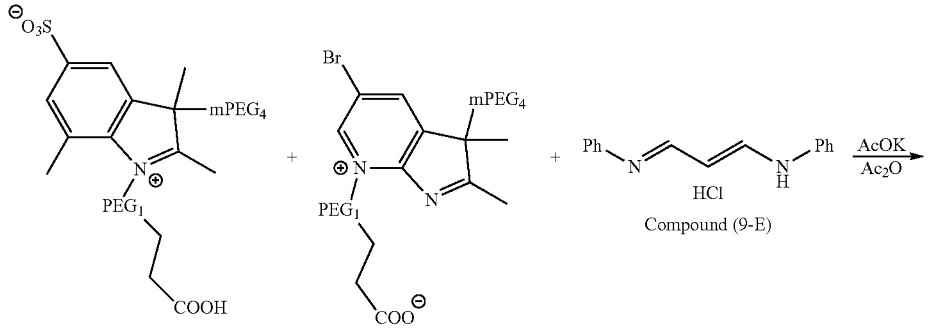
Compound (9-D) Compound (9-C) Compound (9-E)
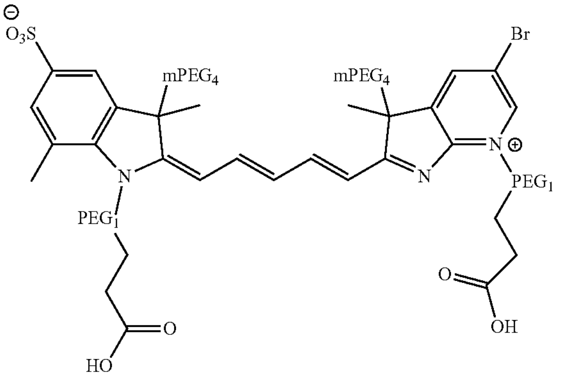
Compound (9-F)
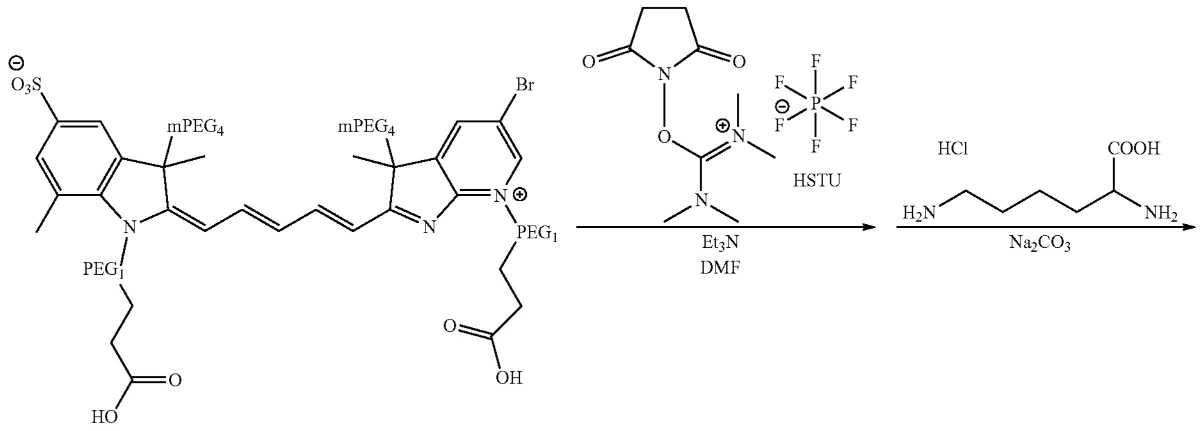
Compound (9-F)
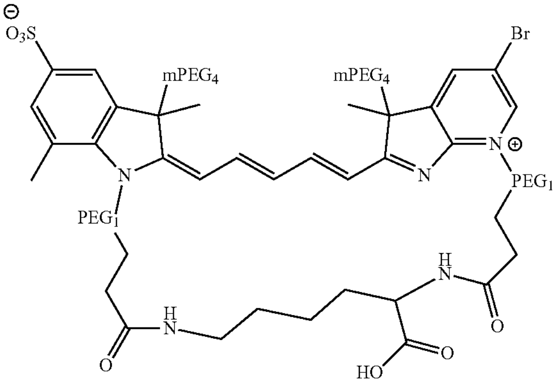
Compound (9-G)

-continued
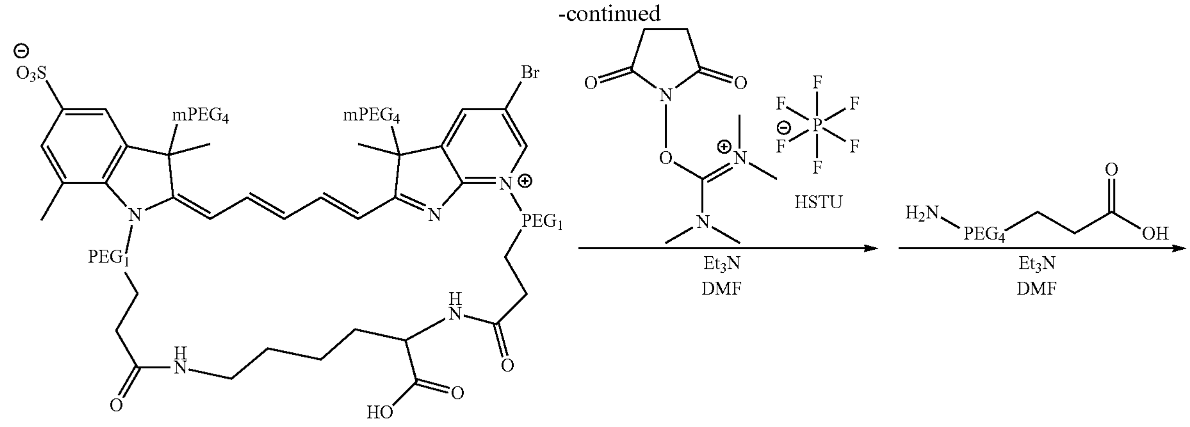
Compound (9-G)
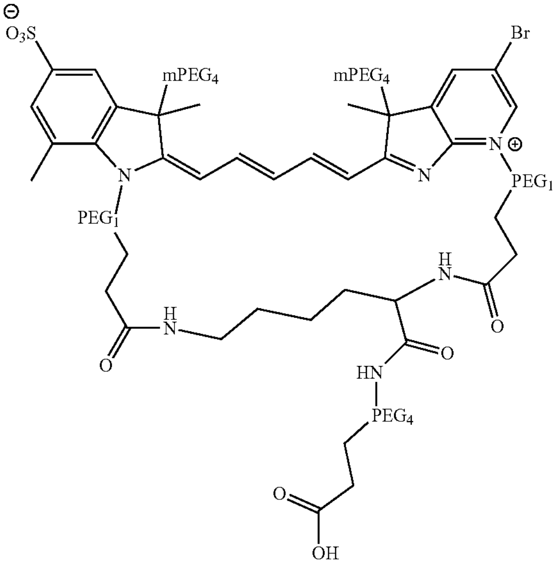
Compound (9-H)
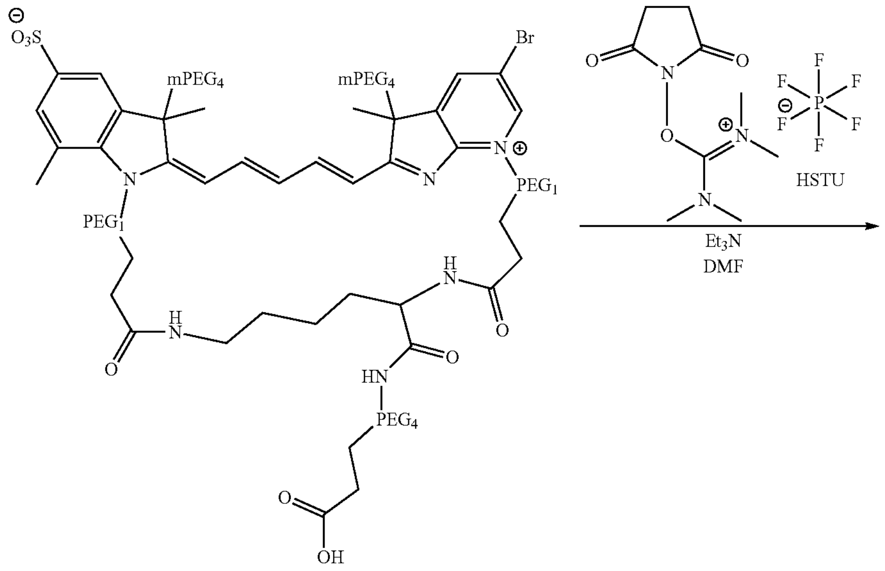
Compound (9-H)

-continued
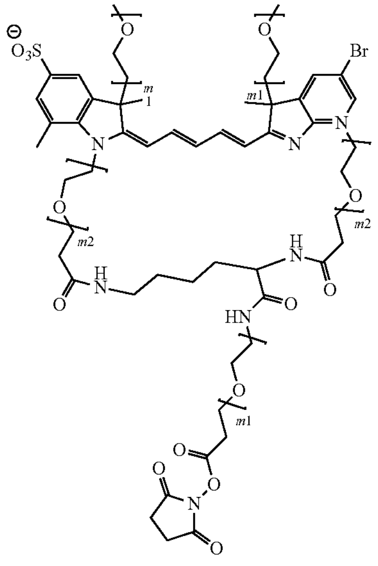
m1 = 4
m2 = 1
Compound (9)
Synthesis of Compound (10)
A compound (10) was synthesized in the same manner as the compound (1), based on the following scheme. The results of the MS measurement of the compound (10-H) were as follows.
MS (ESI m/z):$(M+H^+)^+$=1,334, $(M-H^+)^-$=1,332
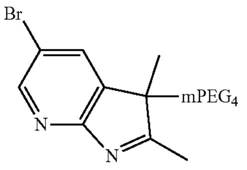
Compound (9-B)
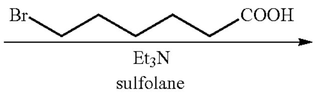
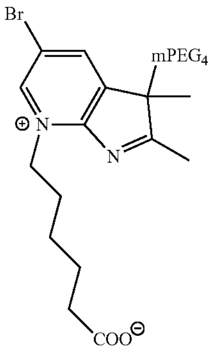
Compound (10-C)
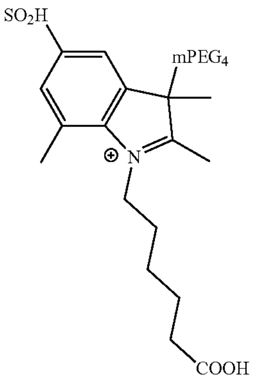
Compound (3-C)
+
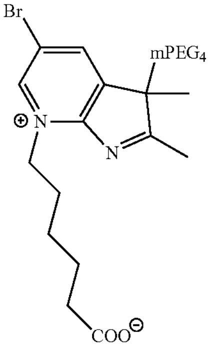
Compound (10-C)
+
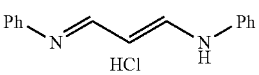
Compound (9-E)
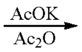

-continued
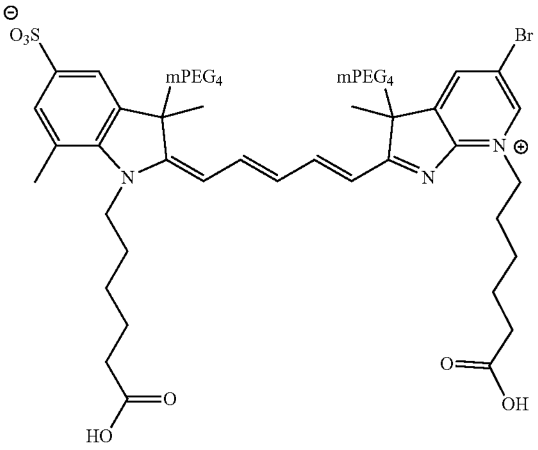
Compound (10-F)
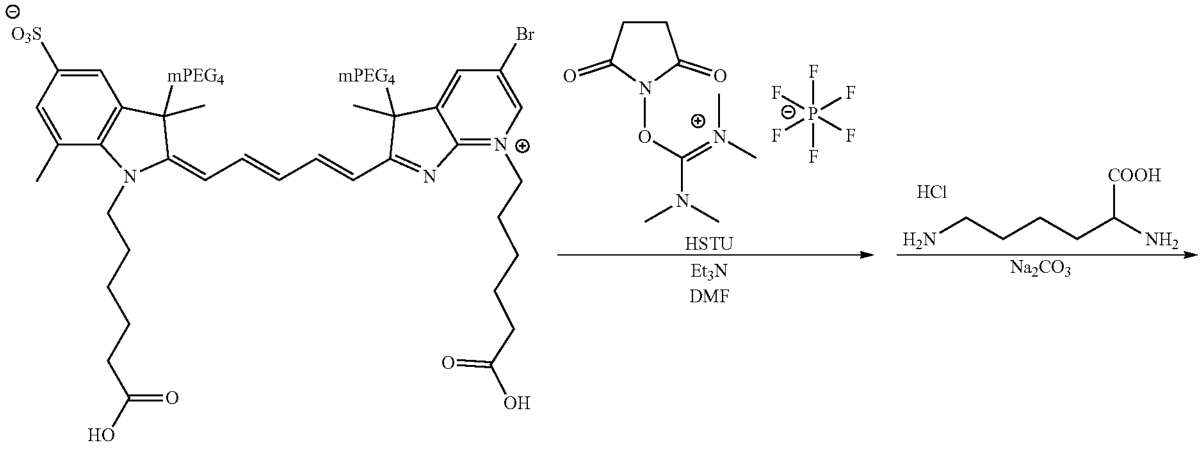
Compound (10-F)
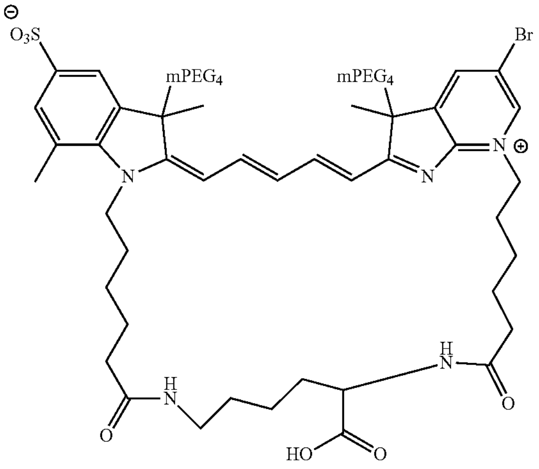
Compound (10-G)

-continued
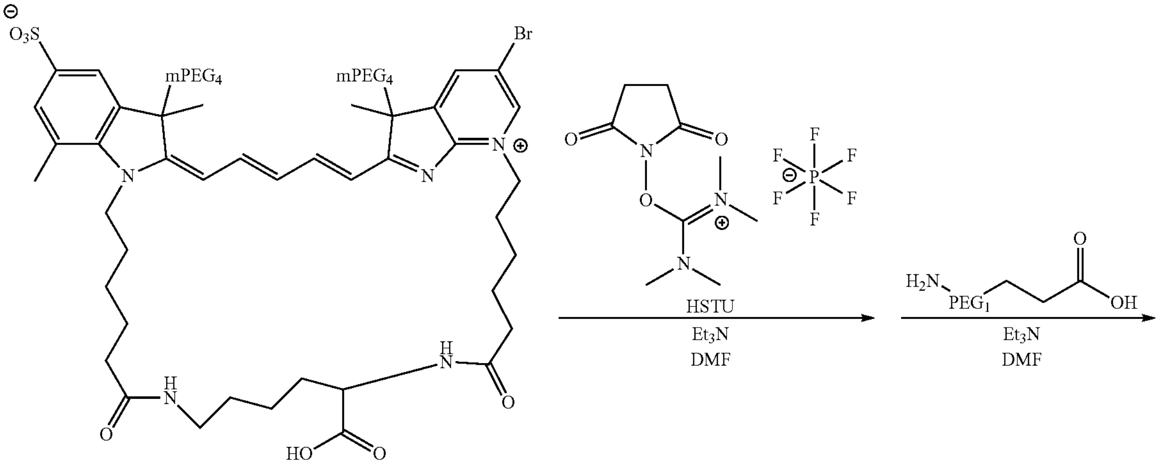
Compound (10-G)
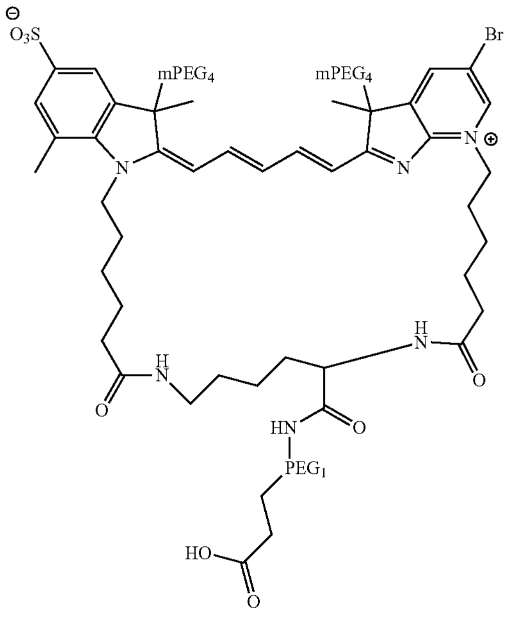
Compound (10-H)

-continued
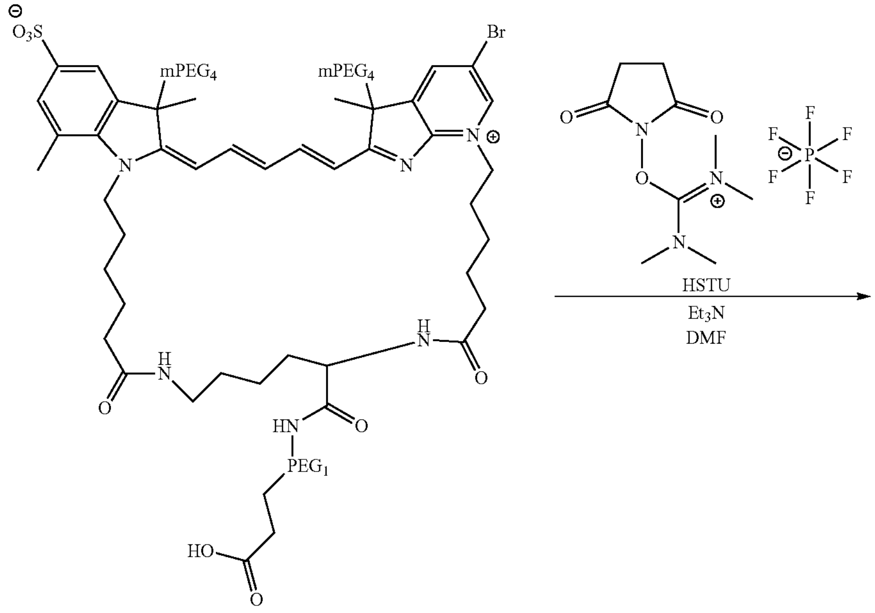
Compound (10-H)
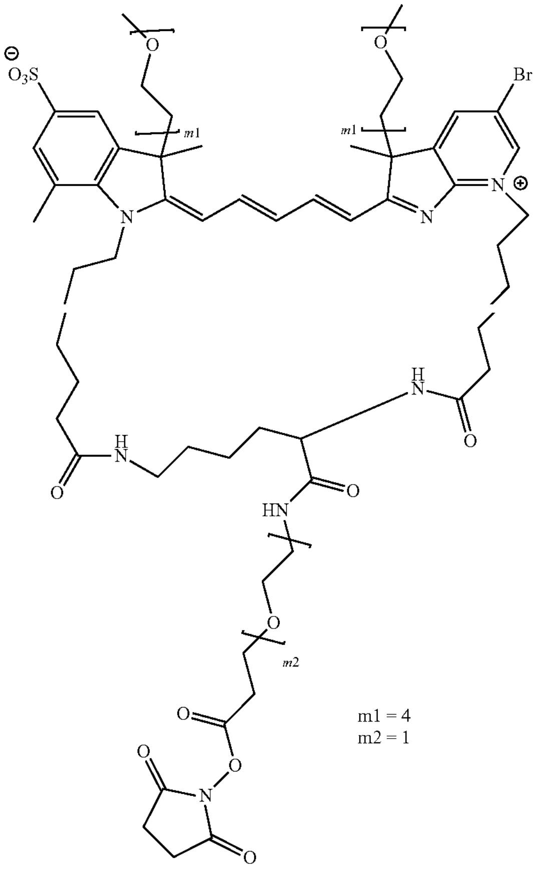
Compound (10)

Synthesis of Compound (11)
A compound (11) was synthesized in the same manner as the compound (1), based on the following scheme. The results of the MS measurement of the compound (11-F) were as follows.
MS (ESI m/z):$(M+H^+)^+$=1,645, $(M-H^+)^-$=1,643
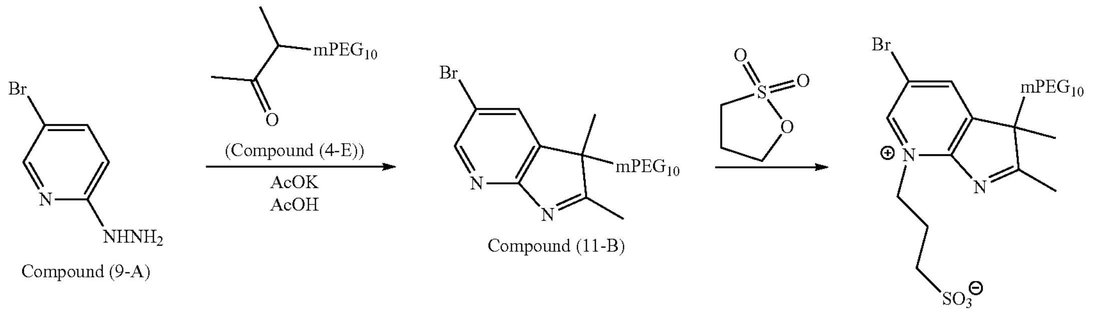
Compound (9-A)
Compound (11-B)
Compound (11-C)
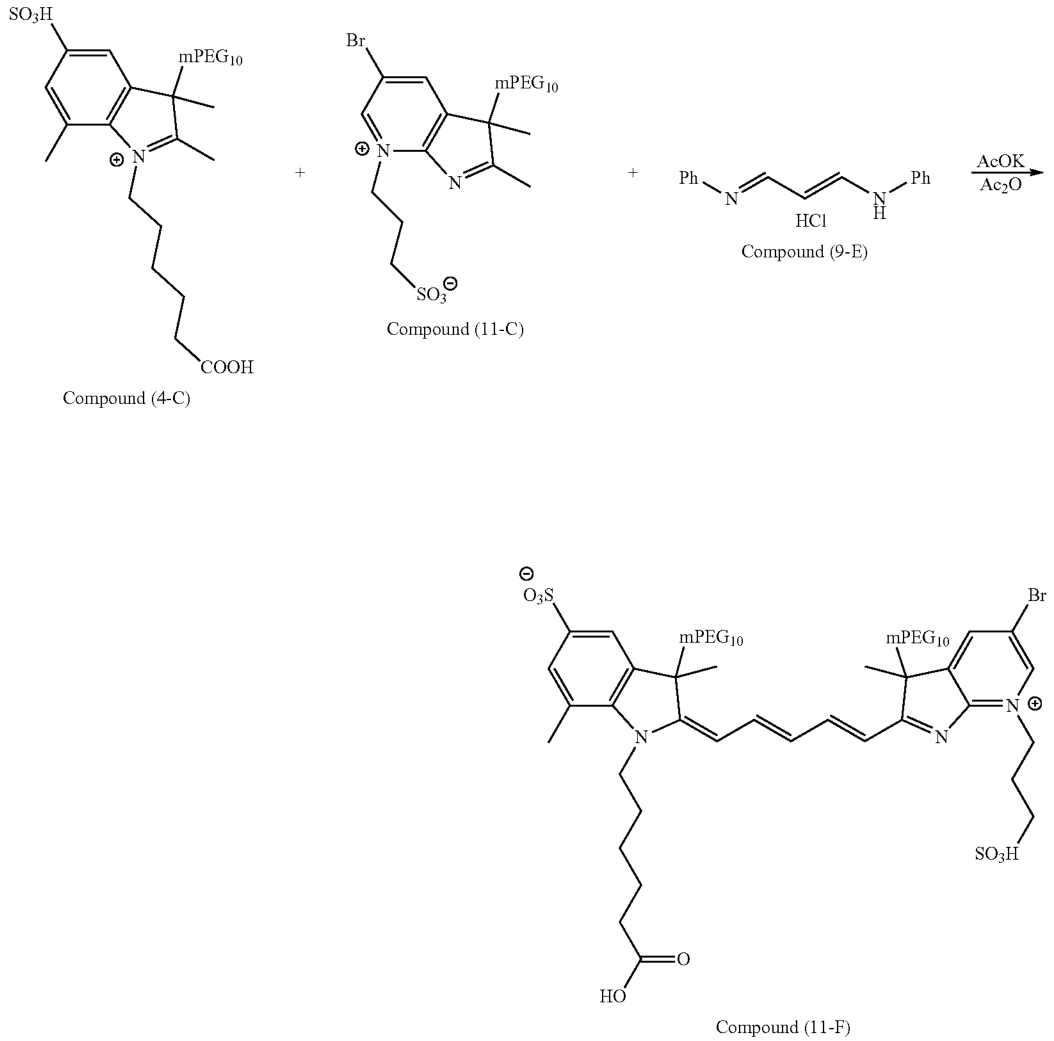
Compound (4-C)
Compound (11-C)
Compound (9-E)
Compound (11-F)

-continued
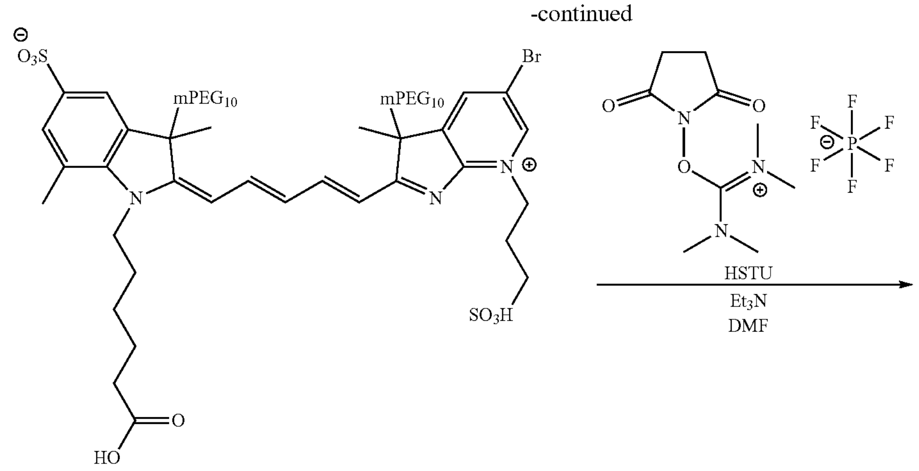
Compound (11-F)
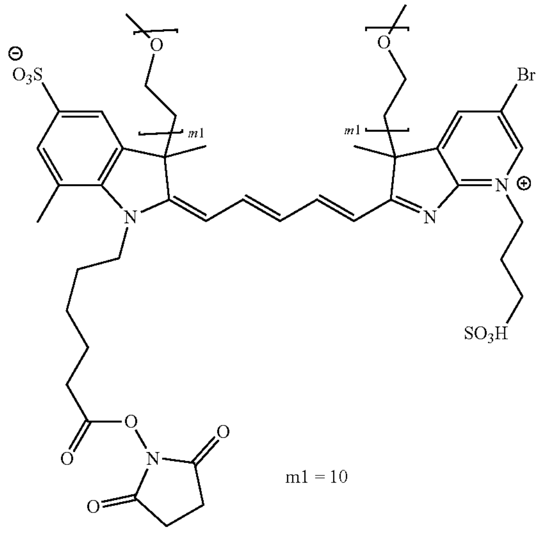
ml = 10
Compound (11)
Synthesis of Comparative Compound (2)
A comparative compound (2) was synthesized in the same manner as the compound (1), based on the following scheme. The results of the MS measurement of the compound (c2-L) were as follows.
MS (ESI m/z):$(M+H^+)^+$=2,000, $(M-H^+)^-$=1,998
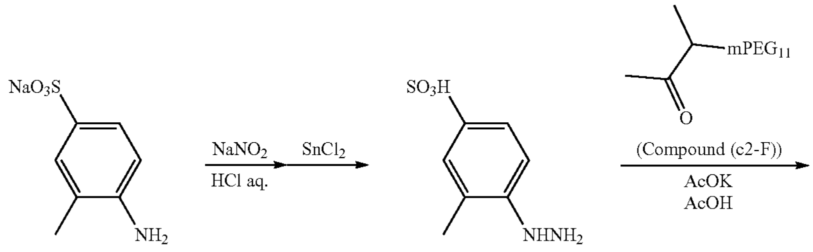
Compound (1-A) Compound (1-G)

-continued
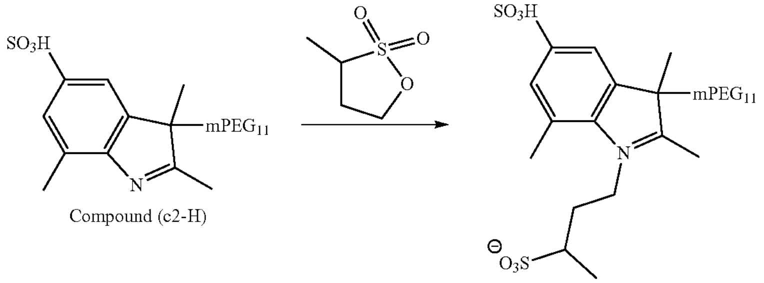
Compound (c2-H)
Compound (c2-I)
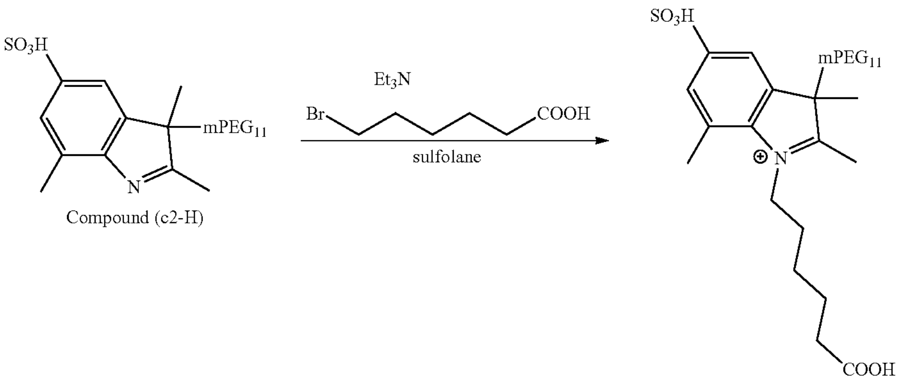
Compound (c2-H)
Compound (c2-C)
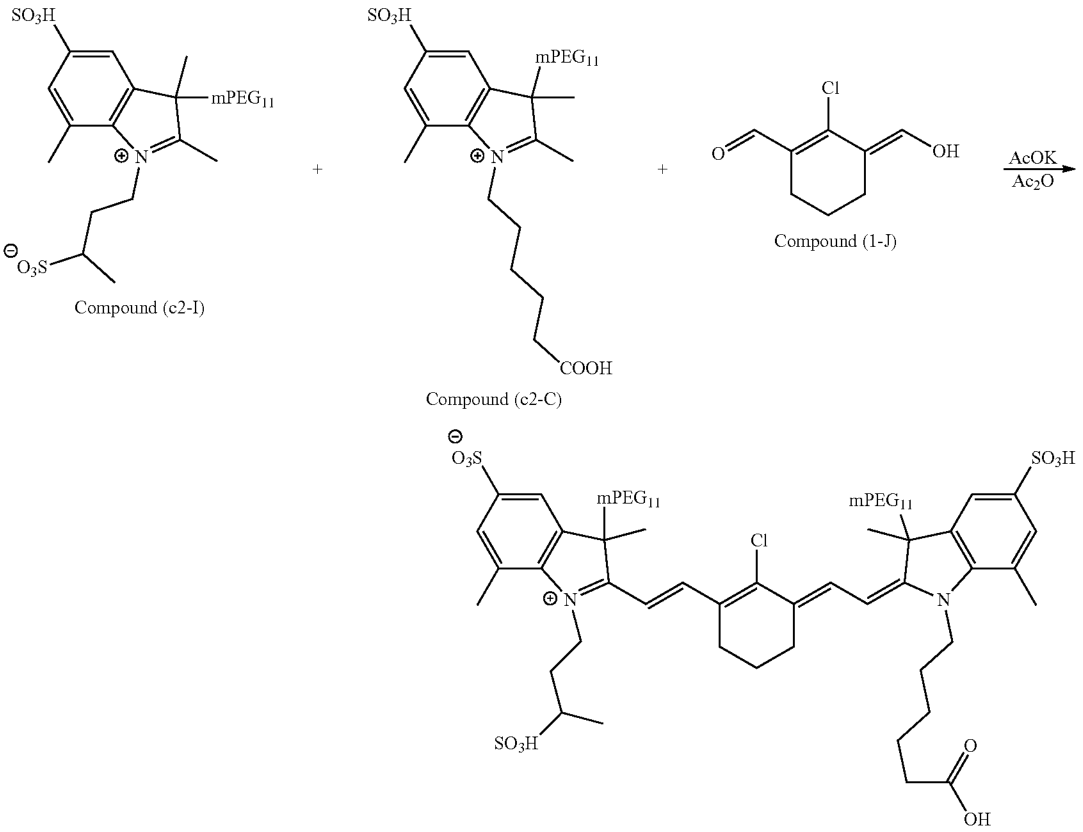
Compound (c2-I)
+
Compound (c2-C)
+
Compound (1-J)
Compound (c2-K)

-continued
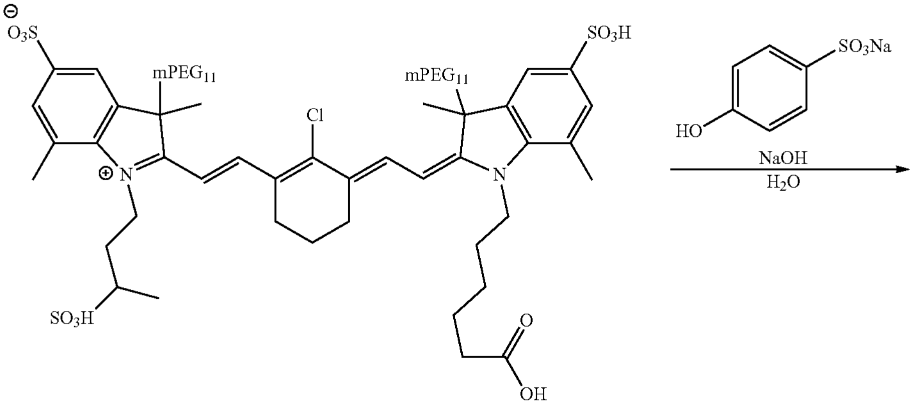
Compound (c2-K)
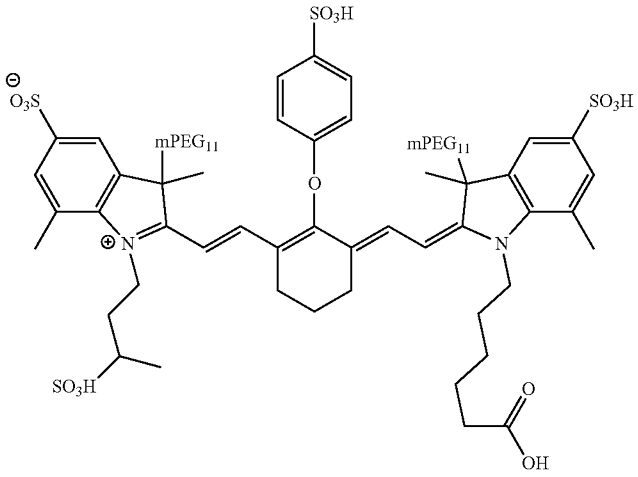
Compound (c2-L)
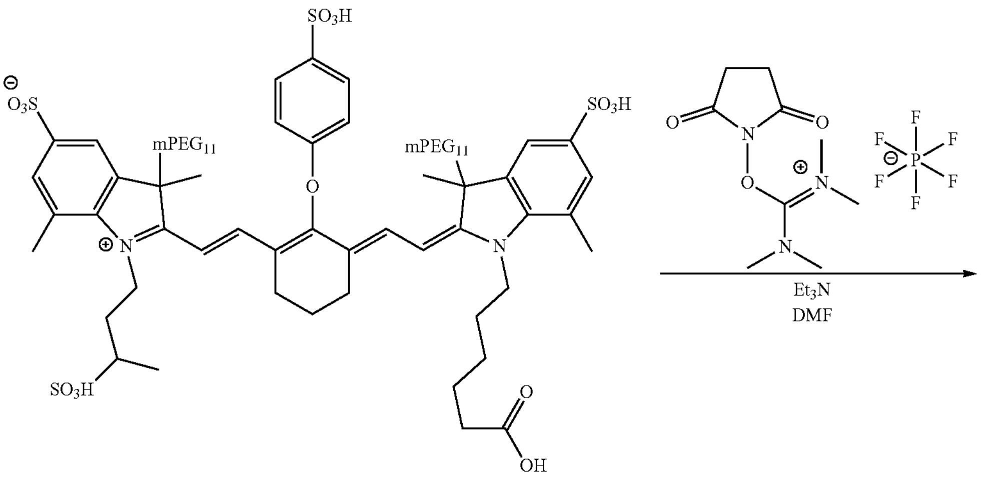
Compound (c2-L)

-continued
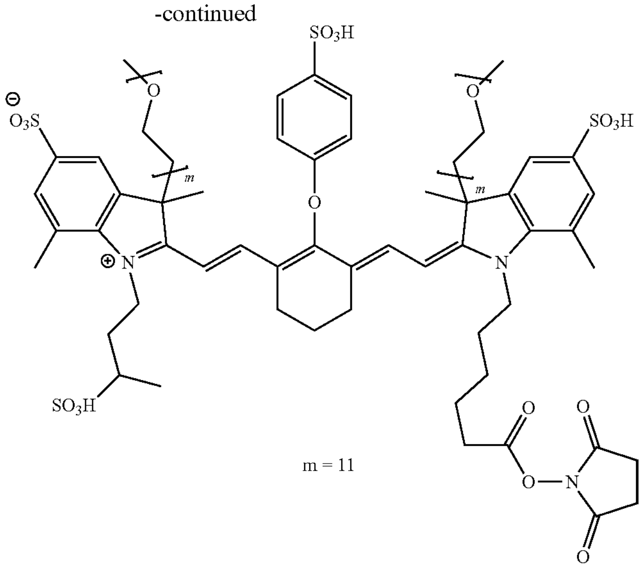
m = 11
Comparative compound (2)
Synthesis of Comparative Compound (3)
A comparative compound (3) was synthesized in the same manner as the compound (1), based on the following scheme. The results of the MS measurement of the compound (c3-L) were as follows.
MS (ESI m/z):$(M+H^+)^+$=1,355, $(M-H^+)^-$=1,353
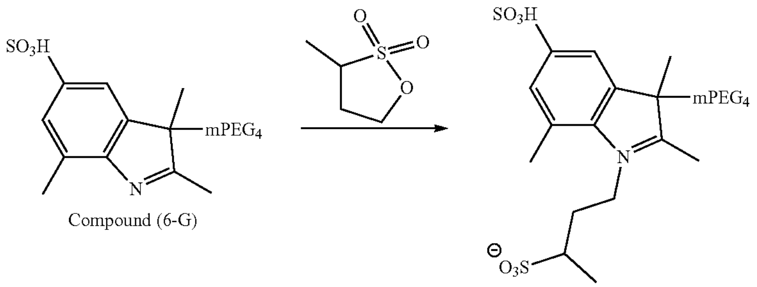
Compound (6-G)
Compound (c3-I)
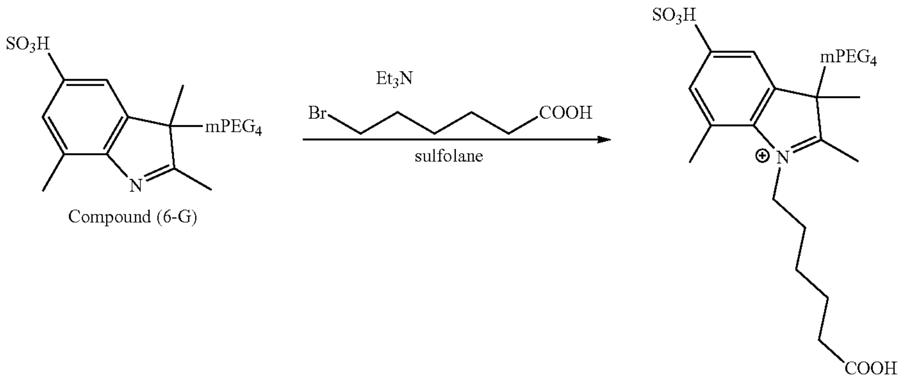
Compound (6-G)
Compound (c3-C)

-continued
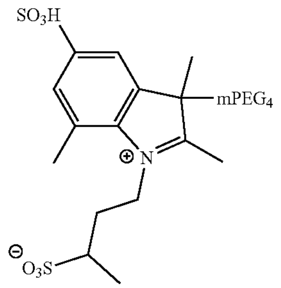
Compound (c3-I)
+
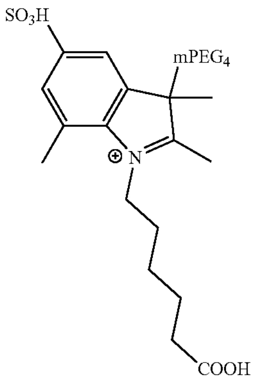
Compound (c3-C)
+
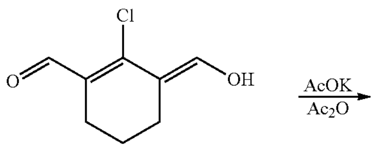
Compound (1-J)
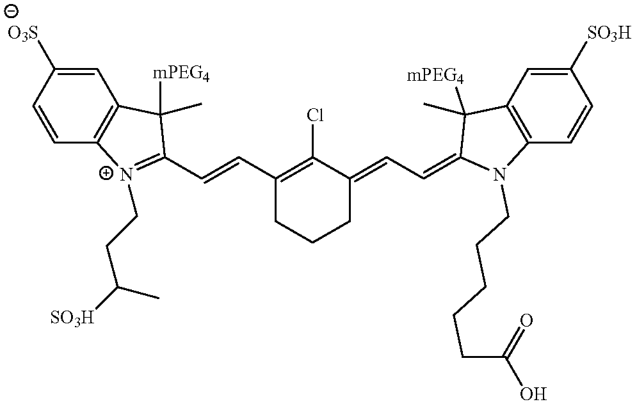
Compound (c3-K)
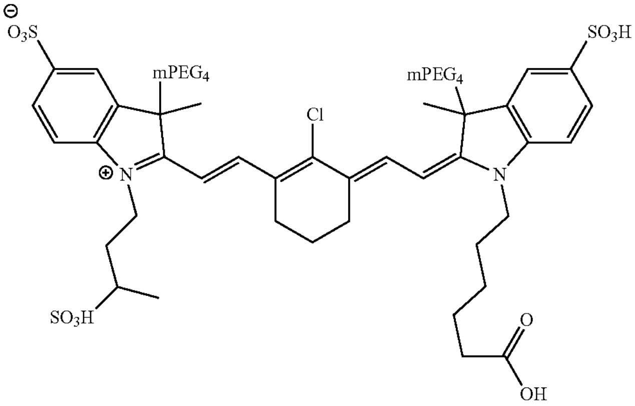
Compound (c3-K)
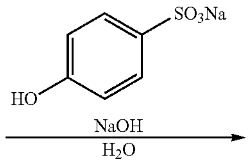

-continued
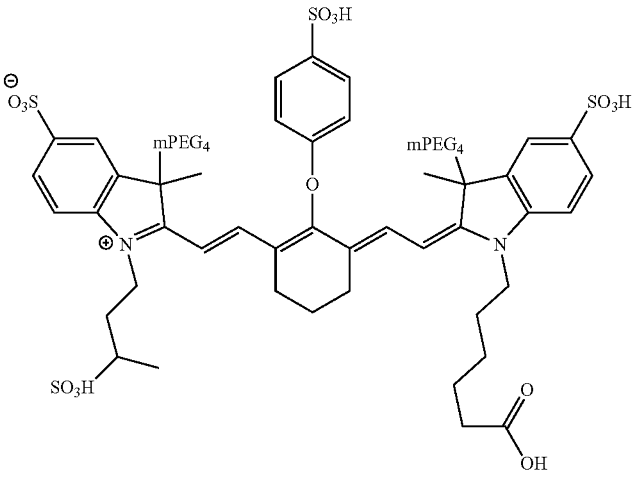
Compound (c3-L)
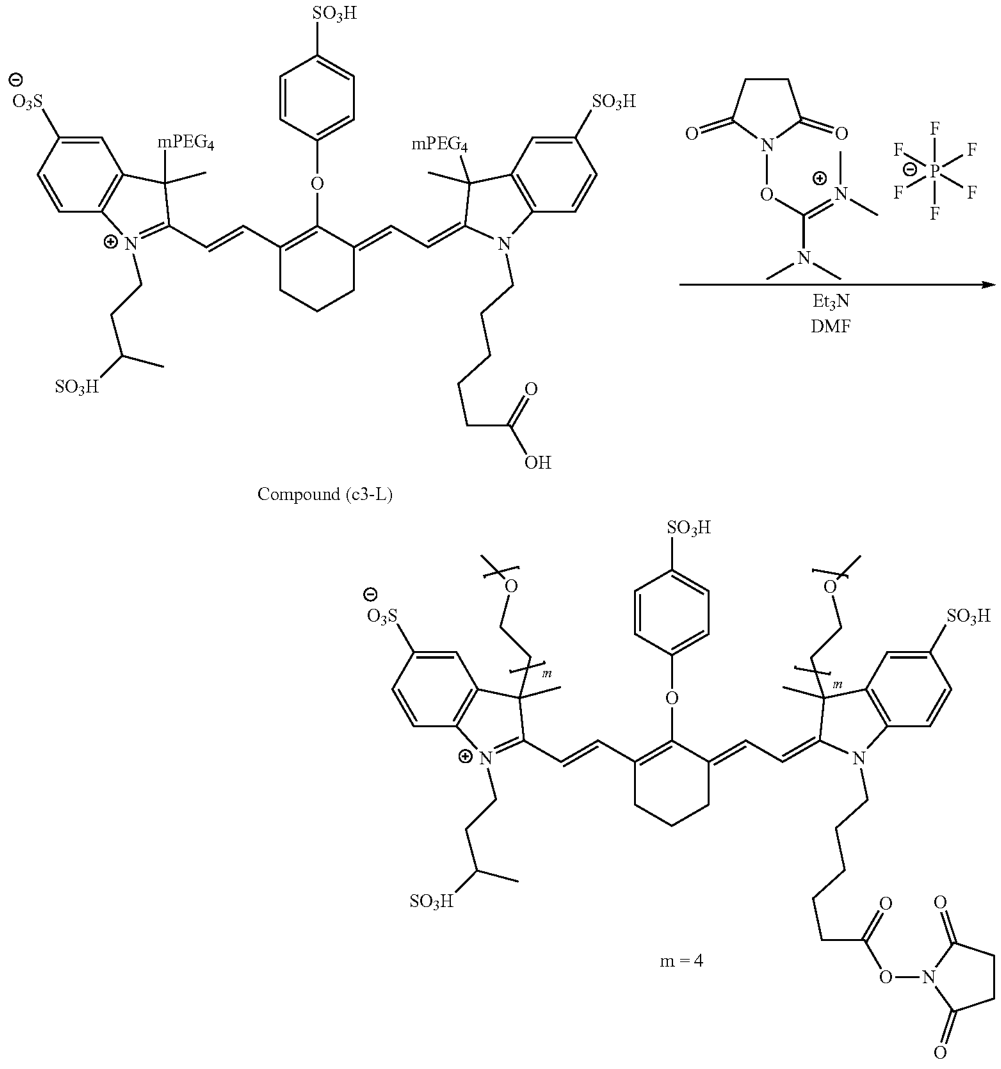
Compound (c3-L)
Comparative compound (3)

Synthesis of Comparative Compound (4)
A comparative compound (4) was synthesized in the same manner as the compound (1), based on the following scheme. The results of the MS measurement of the compound (c4-F) were as follows.
MS (ESI m/z):$(M+H^+)^+$=764, $(M-H^+)^-$=762
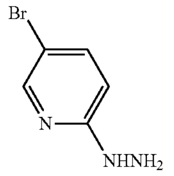
Compound (9-A)
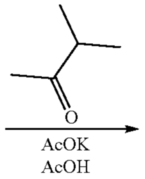
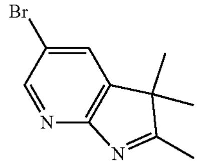
Compound (c4-B)
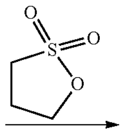
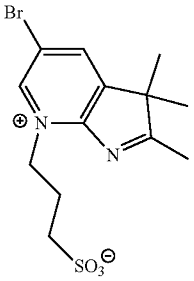
Compound (c4-C)
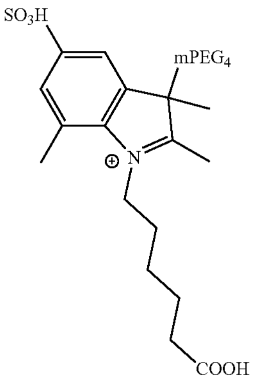
Compound (c3-C)
+
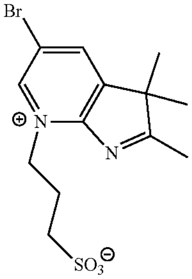
Compound (c4-C)
+
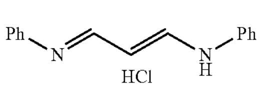
Compound (9-E)
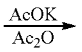
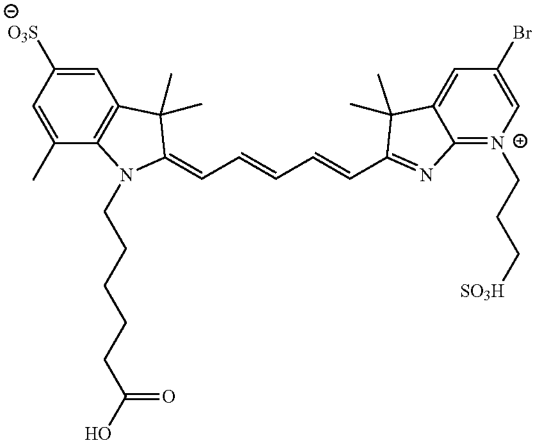
Compound (c4-F)

-continued
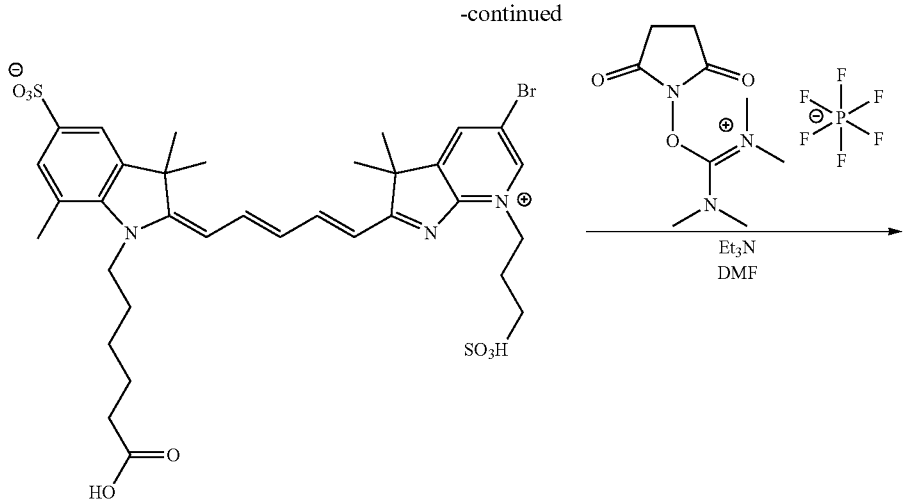
Compound (c4-F)
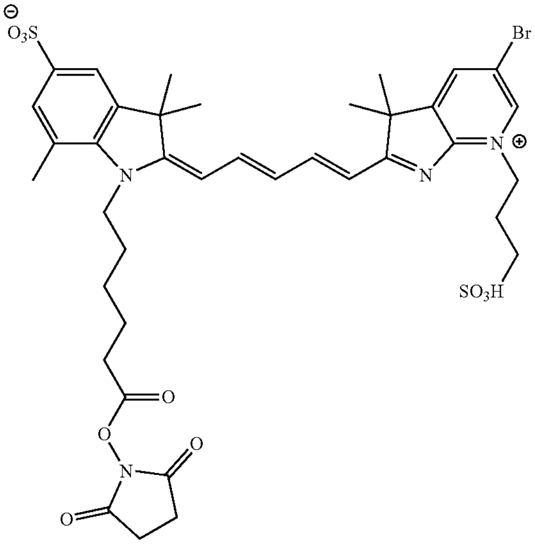
Comparative Compound (4)
Synthesis of Comparative Compound (5)
A comparative compound (5) was synthesized in the same manner as the compound (1), based on the following scheme. The results of the MS measurement of the compound (c5-F) were as follows.
MS (ESI m/z):$(M+H^+)^+$=1,733, $(M-H^+)^-$=1,731
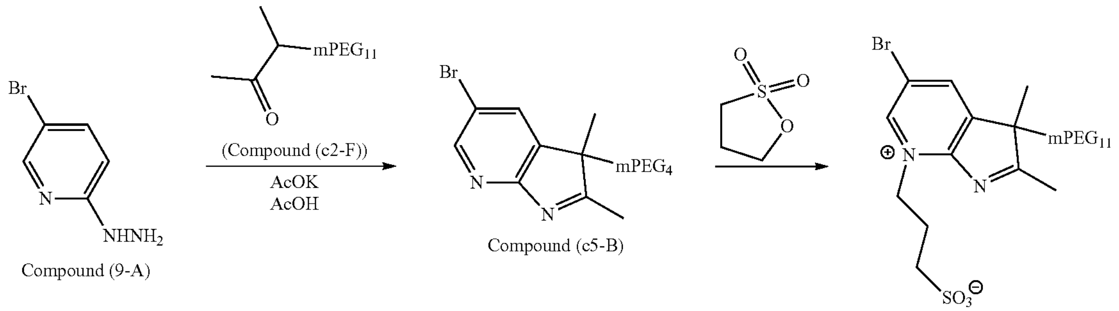
Compound (9-A)
Compound (c5-B)
Compound (c5-C)

-continued
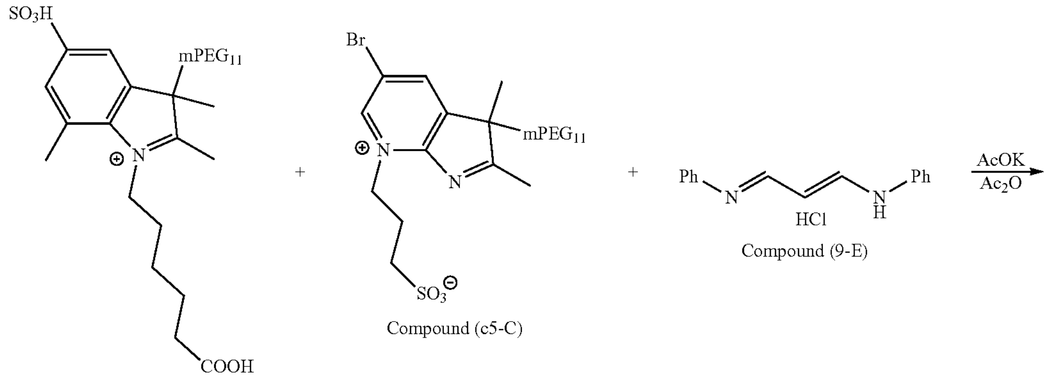
Compound (c2-C)
Compound (c5-C)
Compound (9-E)
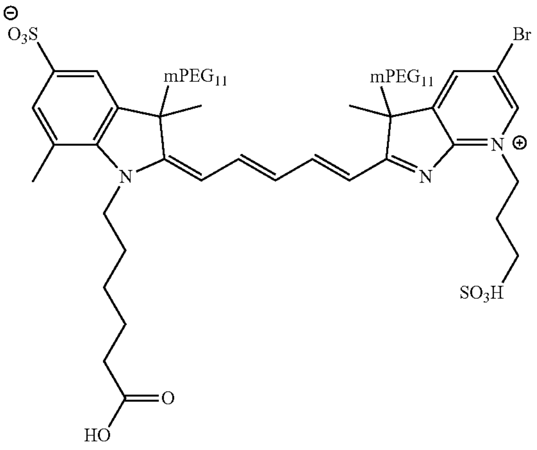
Compound (c5-F)
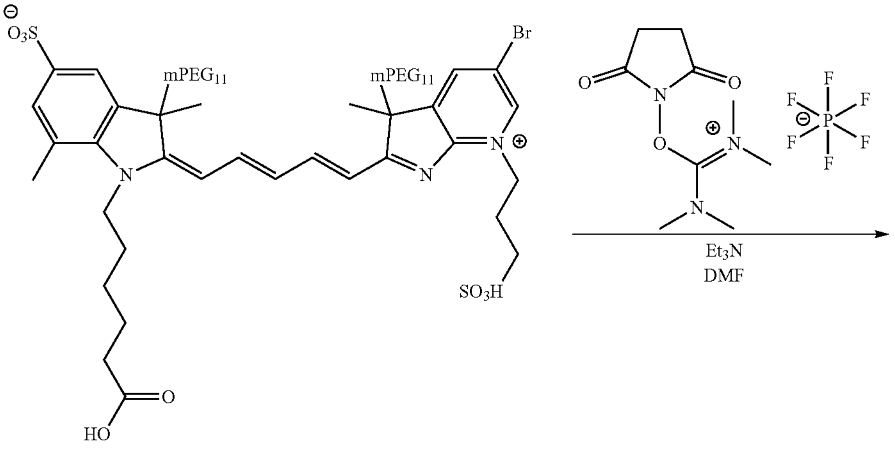
Compound (c5-F)

-continued
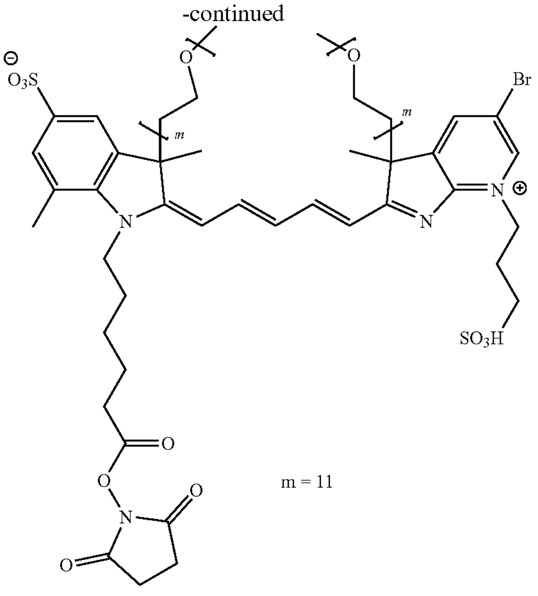
m = 11
Comparative Compound (5)
Synthesis of Comparative Compound (6)
A comparative compound (6) was synthesized in the same manner as the compound (1), based on the following scheme. The results of the MS measurement of the compound (c6-F) were as follows.
MS (ESI m/z):$(M+H^+)^+$1,363, $(M-H^+)^-$=1,361
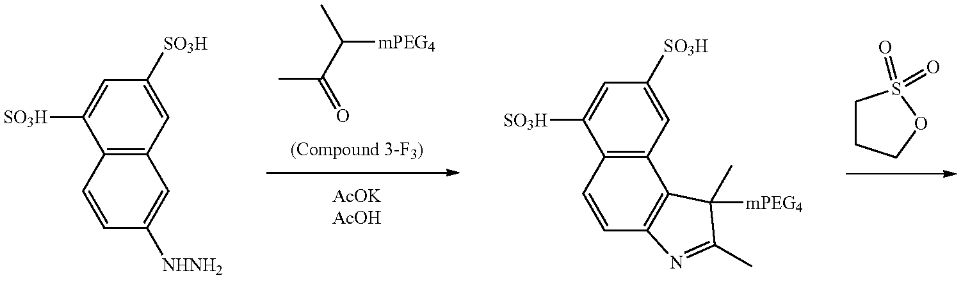
Compound (c6-A)
Compound (c6-B)
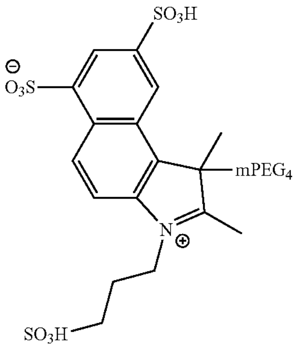
Compound (c6-C)

-continued
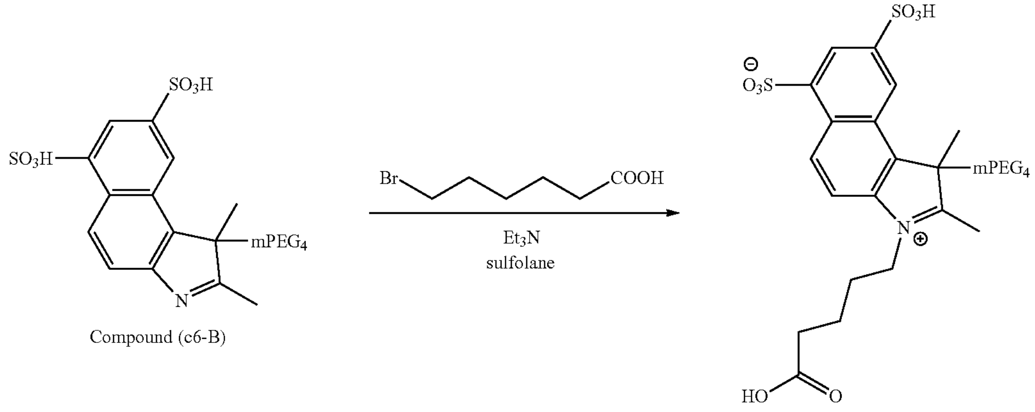
Compound (c6-B)
Compound (c6-D)
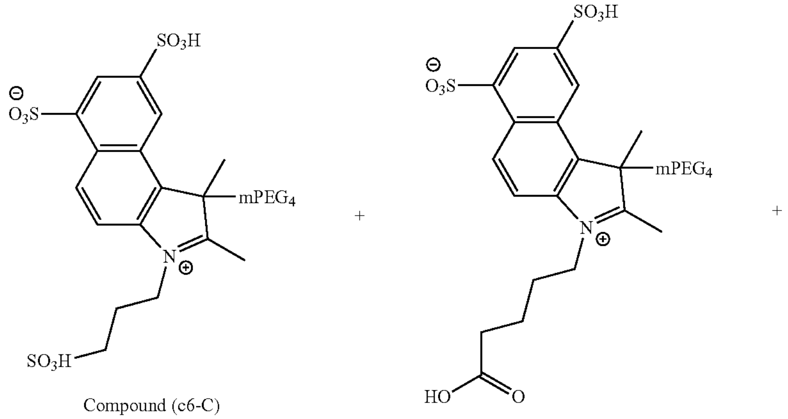
Compound (c6-C)
Compound (c6-D)
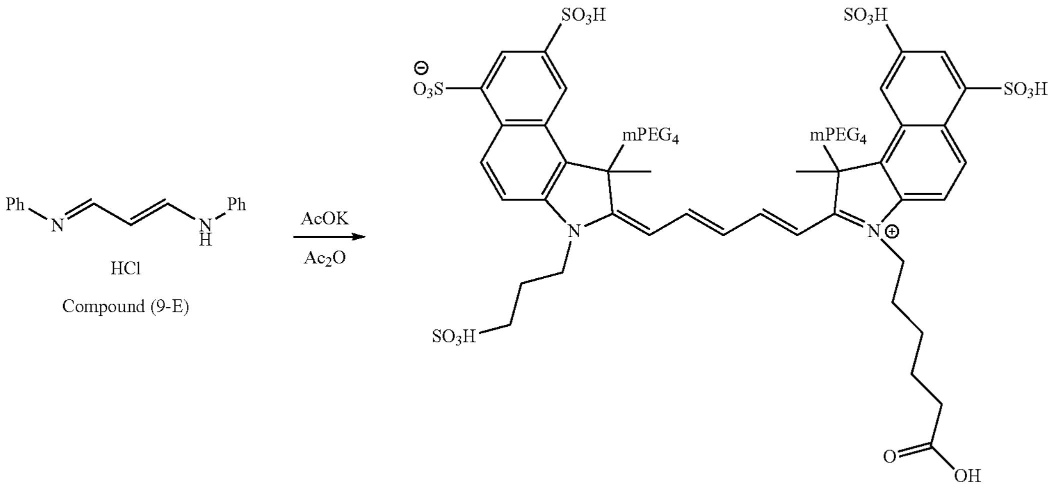
Compound (9-E)
Compound (c6-F)

-continued

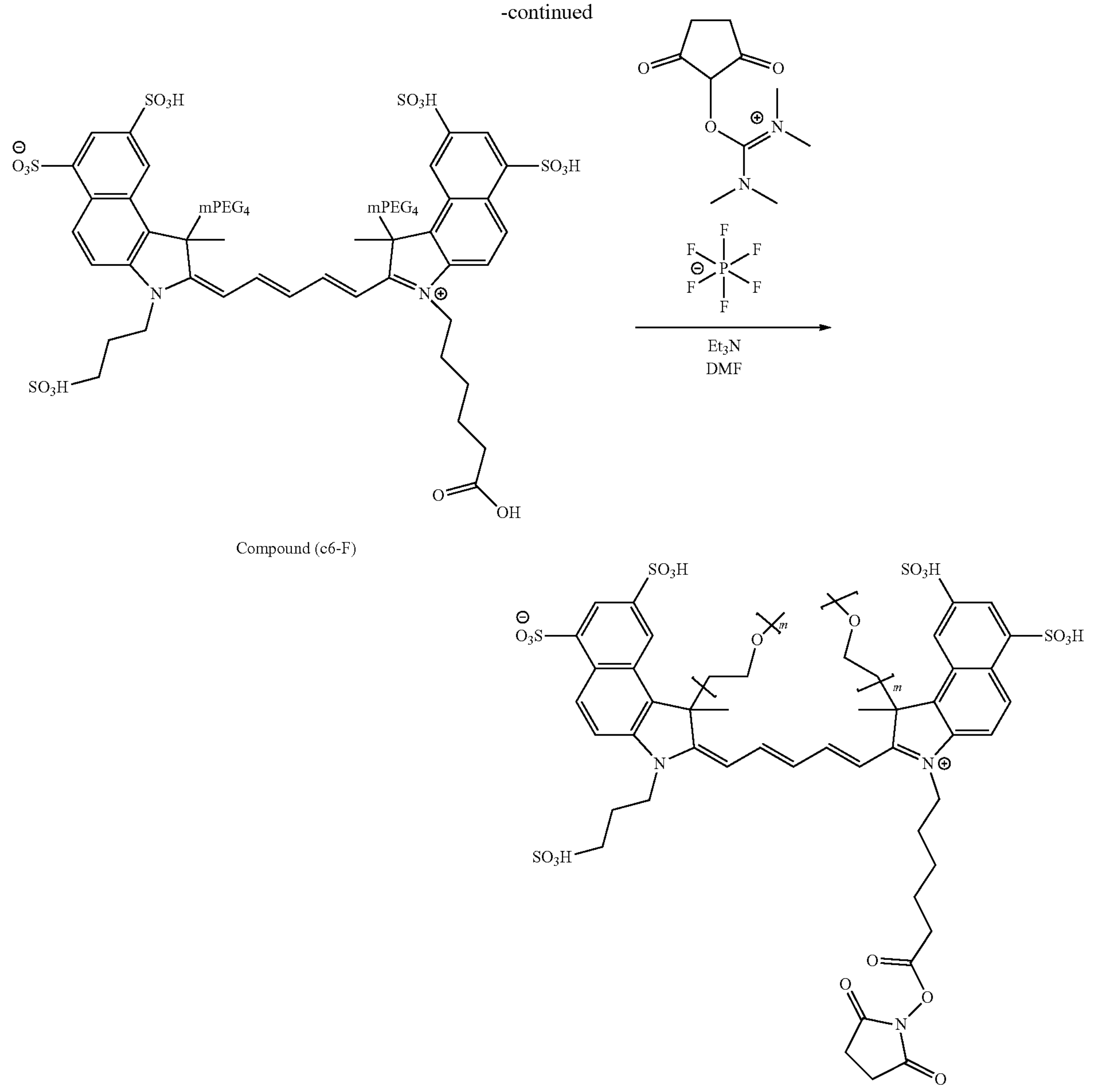

Compound (c6-F)

m = 4
Comparative compound (6)

Example 1

For each of the above described compounds the fluorescence labeling rate, the solution fluorescence intensity, and the fluorescence intensity on the membrane were evaluated.

[1] Evaluation of Fluorescence Labeling Rate

217 μL of an anti-rabbit IgG antibody (2.3 mg/ml) and 21.7 μL of a carbonate buffer were added to a microtube, the resultant mixture was shaken and stirred. Then, a dimethyl sulfoxide solution of the compound (1) was added thereto so that the molar equivalent ratio of the compound (1) to the antibody was as shown in Table 1, and the resultant mixture further was shaken and stirred. After being allowed to stand at room temperature for 1 hour, the reaction solution was purified using a gel filtration chromatography column PD10 (manufactured by GE Healthcare Life Sciences) and a PBS solution (a phosphate-buffered saline solution) to obtain a labeled antibody (1). The fluorescence labeling rate of the obtained labeled antibody was calculated according to the method described below. The results are summarized in Table 1.

As the method for calculating the fluorescence labeling rate, a general method as described below was used. The description in [ ] indicates a unit, and [−] means that there is no unit. In this study, protein means an anti-rabbit IgG antibody.

fluorescence labeling rate=fluorescent dye concentration/protein concentration

The fluorescent dye concentration means the total molar concentration [M] of the labeled fluorescent dye, and the protein concentration means the molar concentration [M] of the fluorescently labeled protein. They are respectively calculated according to the following expressions.

$$\text{Fluorescent dye concentration}=\text{Dye}_{max}/\varepsilon_{dye}$$

$$\text{Protein concentration}=(\text{IgG}_{280}-(\text{Dye}_{max}\times\text{CF}))/\varepsilon_{protein}$$

Each symbol in the above expressions is as follows.

$Dye_{max}$: Absorption [−] of fluorescent dye at maximum absorption wavelength $\varepsilon_{dye}$: Molar absorption coefficient [$M^{-1}cm^{-1}$] of fluorescent dye $IgG_{280}$: Absorption [−] of fluorescently labeled protein at 280 nm $Dye_{280}$: Absorption [−] of fluorescent dye at 280 nm $\varepsilon_{protein}$: Molar absorption coefficient [$M^{-1}cm^{-1}$] of protein CF (correction factor): $Dye_{280}/Dye_{max}$ [−]

In contrast, the compounds (3) and (4), which are the compounds according to the embodiment of the present invention, have the same chemical structure as the comparative compound (2) except for the fact that they differ in that the repetition numbers (m specified in the present invention) of PEG are respectively 4 and 10. It can be seen that all of these compounds (3) and (4) have a high fluorescence labeling rate as compared with the comparative compound (2), and in a case of adopting a structure in which the repetition number of PEG is 10 or less, the decrease in the binding property to an antibody due to the introduction of PEG can be suppressed. Similarly, the compound (11), which is the compound according to the embodiment of the present invention, has the same chemical structure as the comparative compound (5) except for the fact that it differs in that the repetition number (m specified in the present invention) of PEG is 10. It can be seen that this compound (11) has a high fluorescence labeling rate as compared with the comparative compound (5), and in a case of adopting a structure in which the repetition number of PEG is 10 or less, the decrease in the binding property to an antibody due to the introduction of PEG can be suppressed.

TABLE 1

| No. | Labeled antibody | 3 equivalents | 5 equivalents | 7 equivalents | 10 equivalents |
|---|---|---|---|---|---|
| 101 | Compound (1)-IgG | 2.4 | 3.7 | 4.8 | 6.5 |
| 102 | Compound (2)-IgG | 2.2 | 3.5 | 4.6 | 6.6 |
| 103 | Compound (3)-IgG | 2.3 | 3.5 | 4.6 | 6.7 |
| 104 | Compound (4)-IgG | 2.4 | 3.6 | 4.7 | 6.5 |
| 105 | Compound (5)-IgG | 2.1 | 3.1 | 4.2 | 6.0 |
| 106 | Compound (6)-IgG | 2.3 | 3.7 | 4.7 | 6.6 |
| 107 | Compound (7)-IgG | 2.2 | 3.5 | 4.5 | 6.3 |
| 108 | Compound (8)-IgG | 2.3 | 3.5 | 4.6 | 6.5 |
| 109 | Compound (9)-IgG | 2.4 | 3.7 | 4.6 | 6.8 |
| 110 | Compound (10)-IgG | 2.3 | 3.5 | 4.7 | 6.7 |
| 111 | Compound (11)-IgG | 2.1 | 3.5 | 4.4 | 6.0 |
| c11 | Comparative compound (1)-IgG | 2.3 | 3.3 | 4.2 | 6.3 |
| c12 | Comparative compound (2)-IgG | 1.9 | 2.8 | 3.4 | 4.2 |
| c13 | Comparative compound (3)-IgG | 2.1 | 3.4 | 4.3 | 6.4 |
| c14 | Comparative compound (4)-IgG | 2.2 | 3.5 | 4.5 | 6.4 |
| c15 | Comparative compound (5)-IgG | 1.7 | 2.5 | 3.6 | 4.5 |
| c16 | Comparative compound (6)-IgG | 2.2 | 3.5 | 4.5 | 6.3 |

(Note in Table)

In the column of the labeled antibody, the notation of the compound (Z)-IgG or the comparative compound (Z)-IgG means an IgG antibody labeled with the compound (Z) or an IgG antibody labeled with the comparative compound (Z). Here, Z means the number of each compound. They have the same meaning in the following tables.

From the results in Table 1 above, the following points can be seen.

Even in a case where the compounds (1) to (11), which are the compounds according to the embodiment of the present invention, are added at any molar equivalent of 3 equivalents, 5 equivalents, 7 equivalents, or 10 equivalents, with respect to the antibody, they exhibit the fluorescence labeling rate equal to or higher than that in a case where the compound (1), which is a commercially available labeled compound, is used, and the exhibited binding property thereof to the antibody was at a sufficient level without any problem in practical use. This fact can be read from the comparison between No. c11 and Nos. 101 to 111.

On the other hand, the comparative compounds (2) and (5) are not the compounds defined in the present invention in that the repetition number (m specified in the present invention) of PEG is 11. From the comparison between No. c11 and Nos. c12 and c15, the comparative compounds (2) and (5) had a low fluorescence labeling rate as compared with the comparative compound (1), which is a commercially available labeling compound, the fluorescence labeling rate was further decreased as the molar equivalent to the antibody increased, and the binding property to the antibody was inferior.

[2] Evaluation of Solution Fluorescence Intensity 1

A solution of each labeled antibody, prepared by adding 10 equivalents of the dye at the above-described fluorescence labeling rate, was adjusted to a protein concentration of 0.1 mg/ml, and the integrated value of the fluorescence intensity in the fluorescence wavelength range of 810 to 840 nm was calculated by using a spectroscopic fluorescence intensity meter (product name: RF-5300, manufactured by Shimadzu Corporation) with excitation light of 785 nm and unified the exposure conditions. Using the integrated value of the fluorescence intensity of the comparative compound (1)-IgG in the fluorescence wavelength range of 810 nm to 840 nm as the reference value, the ratio to this reference value (the integrated value of the fluorescence intensity of the labeled antibody in the fluorescence wavelength range of 810 nm to 840 nm/the reference value) was calculated, and then, the evaluation was made based on the following evaluation standards. The results are summarized in Table 2.

In the present test, it is determined that a compound has passed the evaluation of the fluorescence intensity in a case where the compound has a rank "D" or higher.

—Evaluation Standards for Fluorescence Intensity—

A: The ratio of fluorescence intensity to the reference value is more than 2 times.

B: The ratio of fluorescence intensity to the reference value is 1.8 times or more and less than 2 times.

C: The ratio of fluorescence intensity to the reference value is 1.6 times or more and less than 1.8 times.

D: The ratio of fluorescence intensity to the reference value is 1.4 times or more and less than 1.6 times.

E: The ratio of fluorescence intensity to the reference value is 1.2 times or more and less than 1.4 times.

F: The ratio of fluorescence intensity to the reference value is 0.9 times or more and less than 1.2 times.

G: The ratio of fluorescence intensity to the reference value is less than 0.9 times.

TABLE 2

| No. | Labeled antibody | Fluorescence intensity (solution) |
|---|---|---|
| 201 | Compound (1)-IgG | D |
| 202 | Compound (2)-IgG | C |
| 203 | Compound (3)-IgG | B |
| 204 | Compound (4)-IgG | C |
| 205 | Compound (5)-IgG | A |
| 206 | Compound (6)-IgG | B |
| 207 | Compound (7)-IgG | B |
| 208 | Compound (8)-IgG | A |
| c21 | Comparative compound (1)-IgG | 1.0 (reference value) |
| c22 | Comparative compound (2)-IgG | F |
| c23 | Comparative compound (3)-IgG | E |

From the results in Table 2 above, the following points can be seen.

The comparative compound (2) is not a compound having the structure defined in the present invention in that the repetition number (m specified in the present invention) of PEG is 11. The fluorescence intensity in the solution of the labeled antibody using this comparative compound (2) is low (No. c22).

The comparative compound (3) is not a compound having the structure defined in the present invention in that the ring $Z^1$ and the ring $Z^2$ are a benzene ring having no substituent at the ortho position with respect to the nitrogen atom to which $L^1$ or $L^2$ is bonded. The fluorescence intensity in the solution of the labeled antibody using this comparative compound (3) is also low (No. c23).

On the other hand, all the labeled antibodies of the compounds (1) to (8), regulated by the present invention have a fluorescence intensity of 1.4 times or more with respect to the fluorescence intensity of the comparative labeled antibody (1) and exhibit an excellent fluorescence intensity (Nos. 201 to 208 with respect to No. c21).

In particular, in the compound (3) having the same chemical structure as the comparative compound (3) except for the fact that the ring $Z^1$ and the ring $Z^2$ are benzene rings having a methyl group at the ortho position with respect to the nitrogen atom to which $L^1$ or $L^2$ is bonded, the evaluation of the fluorescence intensity is B, whereas in the comparative compound (3) having no substituent at the ortho position with respect to the nitrogen atom, the evaluation of the fluorescence intensity is E. From this, it can be seen that in a case of adopting a benzene ring having a substituent at the ortho position, as $Z^1$ and $Z^2$, in which the repetition number of PEG is 10 or less, excellent fluorescence intensity is exhibited in a solution state.

[3] Evaluation of Solution Fluorescence Intensity 2

A solution of each labeled antibody, prepared by adding 10 equivalents of the dye in the above-described evaluation of the fluorescence labeling rate, was adjusted to a protein concentration of 0.1 mg/ml, and the integrated value of the fluorescence intensity in the fluorescence wavelength range of 710 to 730 nm was calculated by using a spectroscopic fluorescence intensity meter (product name: RF-5300, manufactured by Shimadzu Corporation) with excitation light of 685 nm and unified the exposure conditions. Using the integrated value of the fluorescence intensity of the comparative compound (4)-IgG in the fluorescence wavelength range of 710 nm to 730 nm as the reference value, the ratio to this reference value (the integrated value of the fluorescence intensity of the labeled antibody in the fluorescence wavelength range of 710 nm to 730 nm/the reference value) was calculated, and then, the evaluation was made based on the same evaluation standards as in the evaluation of solution fluorescence intensity 1. The results are summarized in Table 3.

In the present test, it is determined that a compound has passed the evaluation of the fluorescence intensity in a case where the compound has a rank "D" or higher.

TABLE 3

| No. | Labeled antibody | Fluorescence intensity (solution) |
|---|---|---|
| 301 | Compound (9)-IgG | A |
| 302 | Compound (10)-IgG | B |
| 303 | Compound (11)-IgG | C |
| c31 | Comparative compound (4)-IgG | 1.0 (reference value) |
| c32 | Comparative compound (5)-IgG | F |
| c33 | Comparative compound (6)-IgG | E |

From the results in Table 3 above, the following can be seen.

The comparative compound (4) is not a compound having the structure defined in the present invention in that it does not have a structure (a structure represented by $-(CH_2-CH_2-O)_m-R^{21}$) containing PEG having the repetition number m, as at least one of $R^1$ to $R^4$, $L^1$, or $L^2$, The comparative compound (5) is not a compound having the structure defined in the present invention in that the repetition number of PEG (m defined in the present invention) is 11, and the comparative compound (6) is not a compound having the structure defined in the present invention in that the ring $Z^1$ and the ring $Z^2$ are a benzene ring having no substituent at the ortho position with respect to the nitrogen atom to which $L^1$ or $L^2$ is bonded. The fluorescence intensities in the solutions of the labeled antibodies using these comparative compounds (4) to (6) are all low (Nos. c31 to c33).

On the other hand, all the labeled antibodies of the compounds (9) to (11), regulated by the present invention have a fluorescence intensity of 1.6 times or more with respect to the fluorescence intensity of the comparative labeled antibody (4) and exhibit an excellent fluorescence intensity (Nos. 301 to 303 with respect to No. c31).

From the results of Tables 2 and 3, it can be seen that the labeled antibody biological substance that is obtained from the compound according to the embodiment of the present invention exhibits an excellent fluorescence intensity in the solution.

[4] Evaluation of Fluorescence Intensity on Membrane 1

An anti-rabbit IgG solution (a solution of each labeled antibody, prepared by adding 10 equivalents of the dye in the evaluation of the fluorescence labeling rate described above) was adjusted to a protein concentration of 5.0 ng/ml, and 2 μL was carefully spotted on a nitrocellulose membrane. The membrane was dried and then blocked in TBS-T with a Fish Gelatin blocking buffer solution. The membrane was incubated at room temperature for 1 hour with stirring. The blocking solution was removed, and the PBS solution of the labeled antibody was diluted 20,000 times with a TBS buffer solution. The membrane was immersed in the diluted solution and incubated for 1 hour with stirring. The membrane was washed 3 times with a TBS-T buffer solution for 10 minutes and finally washed with a TBS buffer solution for 10 minutes. The obtained membrane was dried on a hot plate at 40° C. for 1 hour and imaged using an Amersham Typhoon scanner (manufactured by GEHC) with excitation light of 785 nm under the uniform exposure conditions, thereby calculating the fluorescence intensity in a fluorescence wavelength range of 810 to 840 nm. Using the integrated value of the fluorescence intensity of the comparative compound (1)-IgG in the fluorescence wavelength range of 810 nm to 840 nm as the reference value, the ratio to this reference value (the integrated value of the fluorescence intensity of the labeled antibody in the fluorescence wavelength range of 810 nm to 840 nm/the reference value) was calculated, and then, the evaluation was made based on the following evaluation standards. The results are summarized in Table 4.

In the present test, it is determined that a compound has passed the evaluation of the fluorescence intensity in a case where the compound has a rank "D" or higher.

—Evaluation Standards for Fluorescence Intensity—

A: The ratio of fluorescence intensity to the reference value is more than 4.0 times or more.

B: The ratio of fluorescence intensity to the reference value is 3.0 times or more and less than 4.0 times.

C: The ratio of fluorescence intensity to the reference value is 2.5 times or more and less than 3.0 times.

D: The ratio of fluorescence intensity to the reference value is 2.0 times or more and less than 2.5 times.

E: The ratio of fluorescence intensity to the reference value is 1.5 times or more and less than 2.0 times.

F: The ratio of fluorescence intensity to the reference value is 0.9 times or more and less than 1.5 times.

G: The ratio of fluorescence intensity to the reference value is less than 0.9 times.

TABLE 4

| No. | Labeled antibody | Fluorescence intensity (membrane) |
|---|---|---|
| 401 | Compound (1)-IgG | D |
| 402 | Compound (2)-IgG | C |
| 403 | Compound (3)-IgG | B |
| 404 | Compound (4)-IgG | C |
| 405 | Compound (5)-IgG | A |
| 406 | Compound (6)-IgG | B |
| 407 | Compound (7)-IgG | B |
| 408 | Compound (8)-IgG | A |
| c41 | Comparative compound (1)-IgG | 1.0 (reference value) |
| c42 | Comparative compound (2)-IgG | G |
| c43 | Comparative compound (3)-IgG | E |

From the results in Table 4 above, the following points can be seen.

The comparative compound (2) is not a compound having the structure defined in the present invention in that the repetition number (m specified in the present invention) of PEG is 11. The fluorescence intensity of the labeled antibody using this comparative compound (2) on the membrane is low (No. c42).

The comparative compound (3) is not a compound having the structure defined in the present invention in that the ring $Z^1$ and the ring $Z^2$ are a benzene ring having no substituent at the ortho position with respect to the nitrogen atom to which $L^1$ or $L^2$ is bonded. The fluorescence intensity of the labeled antibody using this comparative compound (3) on the membrane is also low (No. c43).

On the other hand, all the labeled antibodies of the compounds (1) to (8), regulated by the present invention have a fluorescence intensity of 2.0 times or more with respect to the fluorescence intensity of the comparative labeled antibody (1) and exhibit an excellent fluorescence intensity (Nos. 401 to 408 with respect to No. c41).

In particular, in the compound (3) having the same chemical structure as the comparative compound (3) except for the fact that the ring $Z^1$ and the ring $Z^2$ are benzene rings having a methyl group at the ortho position with respect to the nitrogen atom to which $L^1$ or $L^2$ is bonded, the evaluation of the fluorescence intensity is B, whereas in the comparative compound (3) having no substituent at the ortho position with respect to the nitrogen atom, the evaluation of the fluorescence intensity is E. From this, it can be seen that in a case of adopting a benzene ring having a substituent at the ortho position, as $Z^1$ and $Z^2$, in which the repetition number of PEG is 10 or less, an excellent fluorescence intensity is exhibited on the membrane.

[5] Evaluation of Fluorescence Intensity on Membrane 2

An anti-rabbit IgG solution (a solution of each labeled antibody, prepared by adding 10 equivalents of the dye in the evaluation of the fluorescence labeling rate described above) was adjusted to a protein concentration of 5.0 ng/ml, and 2 μL was carefully spotted on a nitrocellulose membrane. The membrane was dried and then blocked in TBS-T with a Fish Gelatin blocking buffer solution. The membrane was incubated at room temperature for 1 hour with stirring. The blocking solution was removed, and the PBS solution of the labeled antibody was diluted 20,000 times with a TBS buffer solution. The membrane was immersed in the diluted solution and incubated for 1 hour with stirring. The membrane was washed 3 times with a TBS-T buffer solution for 10 minutes and finally washed with a TBS buffer solution for 10 minutes. The obtained membrane was dried on a hot plate at 40° C. for 1 hour and imaged using an Amersham Typhoon scanner (manufactured by GEHC) with excitation light of 685 nm under the uniform exposure conditions, thereby calculating the fluorescence intensity in a fluorescence wavelength range of 710 to 730 nm. Using the integrated value of the fluorescence intensity of the comparative compound (4)-IgG in the fluorescence wavelength range of 710 nm to 730 nm as the reference value, the ratio to this reference value (the integrated value of the fluorescence intensity of the labeled antibody in the fluorescence wavelength range of 710 nm to 730 nm/the reference value) was calculated, and then, the evaluation was made based on the same evaluation standards as in the evaluation of fluorescence intensity on membrane 1. The results are summarized in Table 5.

In the present test, it is determined that a compound has passed the evaluation of the fluorescence intensity in a case where the compound has a rank "D" or higher.

TABLE 5

| No. | Labeled antibody | Fluorescence intensity (membrane) |
|---|---|---|
| 501 | Compound (9)-IgG | A |
| 502 | Compound (10)-IgG | B |
| 503 | Compound (11)-IgG | C |
| c51 | Comparative compound (4)-IgG | 1.0 (reference value) |
| c52 | Comparative compound (5)-IgG | G |
| c53 | Comparative compound (6)-IgG | E |

From the results in Table 5 above, the following points can be seen.

The comparative compound (4) is not a compound having the structure defined in the present invention in that it does not have a structure (a structure represented by $-(CH_2-CH_2-O)_m-R^{21}$) containing PEG having the repetition number m, as at least one of $R^1$ to $R^4$, $L^1$, or $L^2$, The comparative compound (5) is not a compound having the structure defined in the present invention in that the repetition number of PEG (m defined in the present invention) is 11, and the comparative compound (6) is not a compound having the structure defined in the present invention in that the ring $Z^1$ and the ring $Z^2$ are a benzene ring having no substituent at the ortho position with respect to the nitrogen atom to which $L^1$ or $L^2$ is bonded. The fluorescence intensities of the labeled antibodies using these comparative compounds (4) to (6) on the membrane are all low (Nos. c51 to c53).

On the other hand, all the labeled antibodies of the compounds (9) to (11), regulated by the present invention have a fluorescence intensity of 2.5 times or more with respect to the fluorescence intensity of the comparative labeled antibody (4) and exhibit an excellent fluorescence intensity (Nos. 501 to 503 with respect to No. c51).

From the results of Tables 4 and 5, it can be seen that the labeled antibody biological substance that is obtained from the compound according to the embodiment of the present invention exhibits an excellent fluorescence intensity on the membrane.

As described above, the compound according to the embodiment of the present invention has a good binding property to the antibody, and furthermore, the labeled biological substance using the compound of the present invention exhibits an excellent fluorescence intensity in both forms in the solution and on the membrane.

The present invention has been described together with the embodiments of the present invention. However, the inventors of the present invention do not intend to limit the present invention in any part of the details of the description unless otherwise specified, and it is conceived that the present invention should be broadly construed without departing from the spirit and scope of the invention shown in the attached "WHAT IS CLAIMED IS".

What is claimed is:

1. A compound represented by General Formula (1),

General Formula (1)

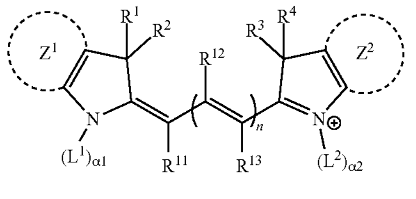

in the General Formula (1), $R^1$ to $R^4$ represent an alkyl group which may have a substituent, an aryl group, a heteroaryl group, or $-(CH_2-CH_2-O)_m-R^{21}$, where m is 1 to 10 and $R^{21}$ represents an alkyl group which may have a substituent, $R^{11}$ to $R^{13}$ represent a hydrogen atom, an alkyl group, an aryl group, a heteroaryl group, an alkoxy group, an aryloxy group, an alkylthio group, an arylthio group, an amino group, or a halogen atom, where at least one of $R^{11}$ to $R^{13}$ is an aryloxy group or an arylthio group, and adjacent groups may be bonded to each other to form a 5-membered or 6-membered ring, n is an integer of 1 to 3, $L^1$ and $L^2$ represent an alkyl group which may have a substituent or $-(CH_2-CH_2-O)_m-R^{21}$, where definitions of $R^{21}$ and m are respectively the same as those of $R^{21}$ and m in $R^1$ to $R^4$ of the General Formula (1), $\alpha 1$ and $\alpha 2$ are 0 or 1, a ring $Z^1$ and a ring $Z^2$ represent a 6-membered ring formed of a ring-constituting atom selected from a carbon atom and a nitrogen atom, may have a substituent, and may form a fused ring, provided that at least one of the ring $Z^1$ or the ring $Z^2$ is a benzene ring represented by General Formula (Zα) or a nitrogen-containing 6-membered ring satisfying the following definition (Zβ), General Formula (Zα)

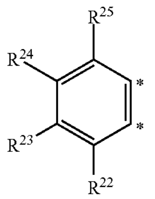

in the General Formula (Zα), $R^{22}$ represents an alkyl group, an alkoxy group, a sulfo group, a sulfonamide group, a nitro group, or a halogen atom, $R^{23}$ to $R^{25}$ represent a hydrogen atom, an alkyl group, an alkoxy group, an aryl group, a sulfo group, a sulfonamide group, a nitro group, or a halogen atom, where adjacent groups may be bonded to each other to form a fused ring, a structure represented by General Formula (Zα) is bonded, at a position of *, to a heterocyclic ring containing a nitrogen atom in General Formula (1) so that $R^{22}$ is at an ortho position with respect to the nitrogen atom to which $L^1$ or $L^2$ is bonded, the definition (Zβ): a nitrogen-containing 6-membered ring in which a ring-constituting atom located at an ortho position with respect to a nitrogen atom to which $L^1$ or $L^2$ is bonded is a nitrogen atom, the ring-constituting nitrogen atom located at the ortho position may be substituted with a substituent, at least one of $R^1$ to $R^4$, $L^1$, or $L^2$ contains a structure represented by $-(CH_2-CH_2-O)_m-R^{21}$, where definitions of $R^{21}$ and m are respectively the same as those of $R^{21}$ and m in $R^1$ to $R^4$ of the General Formula (1), at least one of the substituents contained in $L^1$ and $L^2$ and possessed by the ring-constituting nitrogen atom located at the ortho position in the definition (Zβ) includes a substituent capable of being bonded to a carboxy group or a biological substance, and in a case where at least one of $Z^1$ or $Z^2$ is the nitrogen-containing 6-membered ring satisfying the definition (Zβ), two of the substituents contained in $L^1$, $L^2$, and $R^1$ to $R^4$ and possessed by the ring-constituting nitrogen atom located at the ortho position may be bonded to each other to form a ring containing a methine chain having a repetition number of 2n+3, provided that the compound represented by the General Formula (1) is a neutral compound.

2. The compound according to claim 1, wherein the compound is represented by any one of General Formulae (2-1) to (2-3), General Formula (2-1)

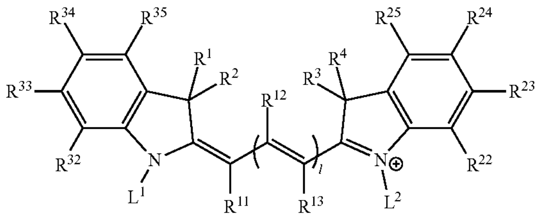

General Formula (2-2)

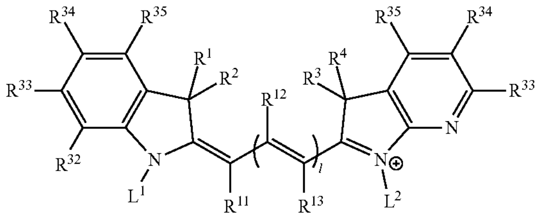

General Formula (2-3)

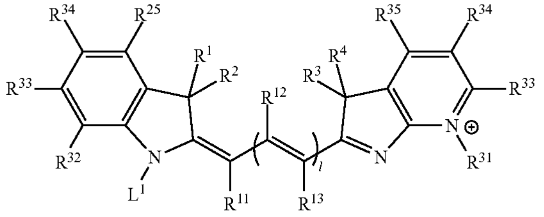

in the General Formula (2-3), $R^{31}$ represents an alkyl group which may have a substituent or —$(CH_2$—$CH_2$—$O)_m$—$R^{21}$, in the General Formula (2-1) to (2-3), $R^{32}$ to $R^{35}$ represent a hydrogen atom, an alkyl group, an alkoxy group, an aryl group, a sulfo group, a sulfonamide group, a nitro group, or a halogen atom, where adjacent groups may be bonded to each other to form a fused ring, definitions of $R^1$ to $R^4$, $R^{11}$ to $R^{13}$, $L^1$, $L^2$, $R^{21}$ to $R^{25}$, and m are respectively the same as those of $R^1$ to $R^4$, $R^{11}$ to $R^{13}$, $L^1$, $L^2$, $R^{21}$ and m in the General Formula (1), definitions of $R^{22}$ to $R^{25}$ are respectively the same as those of $R^{22}$ to $R^{25}$ in the General Formula (Zα), 1 represents 2 or 3, and at least one of $L^1$, $L^2$, or $R^{31}$ contains a substituent capable of being bonded to a carboxy group or a biological substance, provided that the compound represented by any one of Formulae (2-1) to (2-3) is a neutral compound.

3. The compound according to claim 2, wherein at least one of the substituents contained in $L^1$ and $L^2$ and possessed by the ring-constituting nitrogen atom located at the ortho position in the definition (Zβ) or $R^{31}$ includes a substituent capable of being bonded to a carboxy group or a biological substance, and a structure represented by —$(CH_2$—$CH_2$—$O)_m$, where m is 1 to 10.

4. The compound according to claim 1, wherein at least one of $R^1$ or $R^2$ and at least one of $R^3$ or $R^4$ includes a structure represented by —$(CH_2$—$CH_2$—$O)_m$—, where m is 1 to 10.

5. The compound according to claim 1, wherein the compound is represented by any one of General Formulae (5-1) to (5-4), General Formula (5-1)

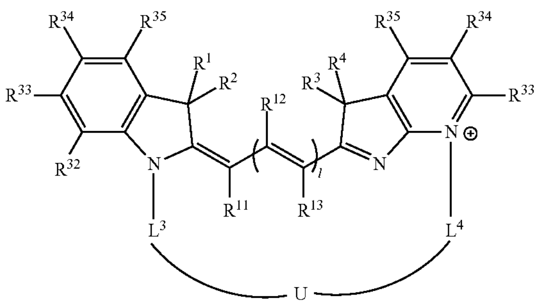

General Formula (5-2)

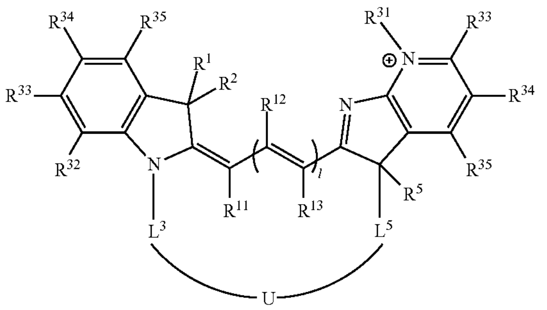

General Formula (5-3)

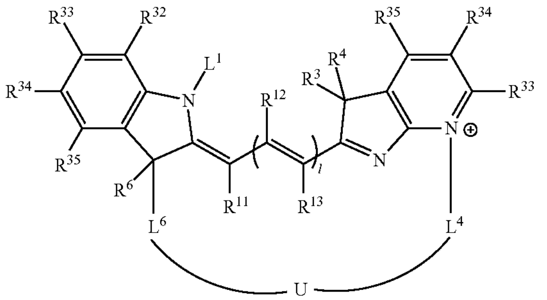

General Formula (5-4)

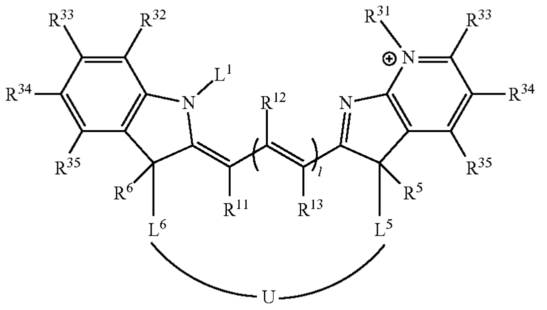

in the General Formula (5-1) to (5-4), $R^1$ to $R^6$ represent an alkyl group which may have a substituent, an aryl group, a heteroaryl group, or —$(CH_2$—$CH_2$—$O)_m$—$R^{21}$, $R^{31}$ represents an alkyl group which may have a substituent or —$(CH_2$—$CH_2$—$O)_m$—$R^{21}$, $R^{32}$ to $R^{35}$ represent a hydrogen atom, an alkyl group, an alkoxy group, an aryl group, a sulfo group, a sulfonamide group, a nitro group, or a halogen atom, where adjacent groups may be bonded to each other to form a fused ring, 1 represents 2 or 3, $L^3$ to $L^6$ represent an alkylene group or —($CH_2$—$CH_2$—O)$_m$-alkylene-*, where * represents a bonding position to U, a linking group U represents a divalent linking group having a total number of atoms of 1 to 100, definitions of $R^{11}$ to $R^{13}$, $R^{21}$, $L^1$, and m are respectively the same as those of $R^{11}$ to $R^{13}$, $R^{21}$, $L^1$, and m in the General Formula (1), at least one of $R^1$ to $R^6$, $L^1$, $R^{31}$, or $L^3$ to $L^6$ includes a structure represented by —($CH_2$—$CH_2$—O)$_m$—, where definition of m is the same as the m in the General Formula (1), and at least one of $L^1$, $R^{31}$, $L^3$ to $L^6$, or the linking group U contains a substituent capable of being bonded to a carboxy group or a biological substance, provided that the compound represented by any one of Formulae (5-1) to (5-4) is a neutral compound.

6. The compound according to claim 5, wherein in the linking group U, a connecting portion to $L^3$ to $L^6$ is an —O— group, an —$NR^{50}$— group, a —COO— group, a —$CONR^{50}$— group, or an —$SO_2NR^{50}$— group, provided that $R^{50}$ is a hydrogen atom or an alkyl group.

7. The compound according to claim 5, wherein at least one of $R^1$ or $R^2$ and at least one of $R^3$ or $R^4$ includes a structure represented by —($CH_2$—$CH_2$—O)$_m$—, where m is 1 to 10.

8. The compound according to claim 5, wherein all of $L^3$ to $L^6$ contains a structure represented by —($CH_2$—$CH_2$—O)$_m$—, where m is 1 to 10.

9. The compound according to claim 5, wherein the linking group U is a divalent linking group having a substituent capable of being bonded to a carboxy group or a biological substance.

10. A labeled biological substance that is obtained by bonding the compound according to claim 1 to a biological substance.

11. The labeled biological substance according to claim 10, wherein the biological substance is any one of a protein, an amino acid, a nucleic acid, a sugar chain, or a phospholipid.

* * * * *